(12) United States Patent
McClurken et al.

(10) Patent No.: US 7,651,494 B2
(45) Date of Patent: Jan. 26, 2010

(54) FLUID-ASSISTED MEDICAL DEVICE

(75) Inventors: Michael E. McClurken, Durham, NH (US); Robert Luzzi, Exeter, NH (US)

(73) Assignee: Salient Surgical Technologies, Inc., Portsmouth, NH (US)

( * ) Notice: Subject to any disclaimer, the term of this patent is extended or adjusted under 35 U.S.C. 154(b) by 0 days.

(21) Appl. No.: 10/354,643

(22) Filed: Jan. 29, 2003

(65) Prior Publication Data
US 2003/0114850 A1 Jun. 19, 2003

Related U.S. Application Data

(63) Continuation of application No. 09/668,403, filed on Sep. 22, 2000, now Pat. No. 6,558,385.

(51) Int. Cl.
*A61B 18/18* (2006.01)
(52) U.S. Cl. .......................... 606/50; 606/49
(58) Field of Classification Search ............ 606/40, 606/42, 41, 46, 45–52
See application file for complete search history.

(56) References Cited

U.S. PATENT DOCUMENTS

| 623,022 | A | 4/1899 | Johnson |
|---|---|---|---|
| 1,735,271 | A | 11/1929 | Groff |
| 1,814,791 | A | 7/1931 | Ende |
| 2,002,594 | A | 5/1935 | Wappler et al. |
| 2,031,682 | A | 2/1936 | Wappler et al. |
| 2,102,270 | A | 12/1937 | Hyams |
| 2,275,167 | A | 3/1942 | Bierman |
| 2,888,928 | A | 6/1959 | Seiger |
| 3,163,166 | A | 12/1964 | Brant et al. |
| 3,682,130 | A | 8/1972 | Jeffers |
| 3,750,650 | A | 8/1973 | Ruttgers |
| 3,901,241 | A | 8/1975 | Allen, Jr. |
| 4,037,590 | A | 7/1977 | Dohring et al. |
| 4,060,088 | A | 11/1977 | Morrison, Jr. et al. |
| 4,116,198 | A | 9/1978 | Roos |
| 4,244,371 | A | 1/1981 | Farin |
| 4,276,874 | A | 7/1981 | Wolvek et al. |

(Continued)

FOREIGN PATENT DOCUMENTS

DE 1 007 960 5/1957

(Continued)

*Primary Examiner*—Roy D Gibson
(74) *Attorney, Agent, or Firm*—Grossman, Tucker, Perreault & Pfleger, PLLC

(57) ABSTRACT

The invention provides a medical device that includes a housing, a tubular member extending from the distal end of the housing, a first arm extending from the distal end of the tubular member, the first arm including a first electrode, a second arm extending from the distal end of the tubular member, the second arm including a second electrode and being disposed coaxially with the first arm, at least one solution infusion opening on each electrode, and a solution delivery channel for delivery of a conductive solution to the solution infusion openings. According to the invention, at least one of the first arm or the second arm is translationally moveable, and at least one of the first arm or the second arm is adapted to be coupled to a source of radiofrequency energy. The invention also provides a corresponding method for treating blood vessels or other tissues of the body.

17 Claims, 24 Drawing Sheets

U.S. PATENT DOCUMENTS

| | | |
|---|---|---|
| 4,301,802 A | 11/1981 | Poler |
| 4,307,720 A | 12/1981 | Weber, Jr. |
| 4,321,931 A | 3/1982 | Hon |
| 4,326,529 A | 4/1982 | Doss et al. |
| 4,355,642 A | 10/1982 | Alferness |
| 4,381,007 A | 4/1983 | Doss |
| 4,532,924 A | 8/1985 | Auth et al. |
| 4,548,207 A | 10/1985 | Reimels |
| 4,567,890 A | 2/1986 | Ohta et al. |
| 4,602,628 A | 7/1986 | Allen, Jr. |
| 4,671,274 A | 6/1987 | Sorochenko |
| 4,674,499 A | 6/1987 | Pao |
| 4,920,982 A | 5/1990 | Goldstein |
| 4,931,047 A | 6/1990 | Broadwin et al. |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,976,711 A | 12/1990 | Parins et al. |
| 4,985,030 A | 1/1991 | Melzer et al. |
| 4,998,933 A | 3/1991 | Eggers et al. |
| 5,009,656 A | 4/1991 | Reimels |
| 5,013,312 A | 5/1991 | Parins et al. |
| 5,035,696 A | 7/1991 | Rydell |
| 5,071,419 A | 12/1991 | Rydell et al. |
| 5,080,660 A | 1/1992 | Buelna |
| 5,122,138 A | 6/1992 | Manwaring |
| 5,125,928 A | 6/1992 | Parins et al. |
| 5,147,357 A | 9/1992 | Rose et al. |
| 5,151,102 A | 9/1992 | Kamiyama et al. |
| 5,156,613 A | 10/1992 | Sawyer |
| 5,167,659 A | 12/1992 | Ohtomo et al. |
| 5,171,311 A | 12/1992 | Rydell et al. |
| 5,190,541 A | 3/1993 | Abele et al. |
| 5,195,959 A | 3/1993 | Smith |
| 5,197,963 A | 3/1993 | Parins |
| 5,197,964 A | 3/1993 | Parins |
| 5,217,460 A | 6/1993 | Knoepfler |
| 5,234,428 A | 8/1993 | Kaufman |
| 5,242,441 A | 9/1993 | Avitall |
| 5,242,442 A | 9/1993 | Hirschfeld |
| 5,269,780 A | 12/1993 | Roos |
| 5,269,781 A | 12/1993 | Hewell, III |
| 5,277,696 A | 1/1994 | Hagen |
| 5,281,215 A | 1/1994 | Milder |
| 5,281,216 A | 1/1994 | Klicek |
| 5,282,799 A | 2/1994 | Rydell |
| 5,290,286 A | 3/1994 | Parins |
| 5,300,087 A | 4/1994 | Knoepfler |
| 5,313,943 A | 5/1994 | Houser et al. |
| 5,318,589 A | 6/1994 | Lichtman |
| 5,322,503 A | 6/1994 | Desai |
| 5,330,521 A | 7/1994 | Cohen |
| 5,334,193 A | 8/1994 | Nardella |
| 5,342,357 A | 8/1994 | Nardella |
| 5,342,359 A | 8/1994 | Rydell |
| 5,348,554 A | 9/1994 | Imran et al. |
| 5,364,394 A | 11/1994 | Mehl |
| 5,383,874 A | 1/1995 | Jackson et al. |
| 5,383,876 A | 1/1995 | Nardella |
| 5,395,312 A | 3/1995 | Desai |
| 5,395,363 A | 3/1995 | Billings et al. |
| 5,401,272 A | 3/1995 | Perkins |
| 5,403,311 A | 4/1995 | Abele et al. |
| 5,403,312 A | 4/1995 | Yates et al. |
| 5,405,344 A | 4/1995 | Williamson et al. |
| 5,405,376 A | 4/1995 | Mulier et al. |
| 5,417,672 A | 5/1995 | Nita et al. |
| 5,417,709 A | 5/1995 | Slater |
| 5,431,649 A | 7/1995 | Mulier et al. |
| 5,433,708 A | 7/1995 | Nichols et al. |
| 5,437,662 A | 8/1995 | Nardella |
| 5,437,664 A | 8/1995 | Cohen et al. |
| 5,441,498 A | 8/1995 | Perkins |
| 5,441,503 A | 8/1995 | Considine et al. |
| 5,445,638 A | 8/1995 | Rydell et al. |
| 5,456,682 A | 10/1995 | Edwards et al. |
| 5,456,684 A | 10/1995 | Schmidt et al. |
| 5,458,596 A | 10/1995 | Lax et al. |
| 5,458,597 A | 10/1995 | Edwards et al. |
| 5,458,598 A | 10/1995 | Feinberg et al. |
| 5,460,629 A | 10/1995 | Shlain et al. |
| 5,462,521 A | 10/1995 | Brucker et al. |
| 5,472,441 A | 12/1995 | Edwards et al. |
| 5,472,443 A | 12/1995 | Cordis et al. |
| 5,487,385 A | 1/1996 | Avitall |
| 5,490,819 A | 2/1996 | Nicholas et al. |
| 5,500,012 A | 3/1996 | Brucker et al. |
| 5,514,130 A | 5/1996 | Baker |
| 5,522,815 A | 6/1996 | Durgin, Jr. et al. |
| 5,536,267 A | 7/1996 | Edwards et al. |
| 5,540,562 A | 7/1996 | Giter |
| 5,542,928 A | 8/1996 | Evans et al. |
| 5,558,671 A | 9/1996 | Yates |
| 5,562,503 A | 10/1996 | Ellman et al. |
| 5,562,703 A | 10/1996 | Desai |
| 5,564,440 A | 10/1996 | Swartz et al. |
| 5,569,242 A | 10/1996 | Lax et al. |
| 5,569,243 A | 10/1996 | Kortenbach et al. |
| 5,573,424 A | 11/1996 | Poppe |
| 5,573,533 A | 11/1996 | Strul |
| 5,575,810 A | 11/1996 | Swanson et al. |
| 5,584,872 A | 12/1996 | LaFontaine et al. |
| 5,599,346 A | 2/1997 | Edwards et al. |
| 5,599,350 A | 2/1997 | Schulze et al. |
| 5,605,539 A | 2/1997 | Buelna et al. |
| 5,609,151 A | 3/1997 | Mulier et al. |
| 5,633,578 A | 5/1997 | Eggers et al. |
| 5,637,110 A | 6/1997 | Pennybacker et al. |
| 5,640,955 A | 6/1997 | Ockuly et al. |
| 5,643,197 A | 7/1997 | Brucker et al. |
| 5,647,869 A | 7/1997 | Goble et al. |
| 5,647,871 A | 7/1997 | Levine et al. |
| 5,653,692 A | 8/1997 | Masterson et al. |
| 5,660,836 A | 8/1997 | Knowlton |
| 5,676,662 A | 10/1997 | Fleischhacker et al. |
| 5,676,693 A | 10/1997 | LaFontaine |
| 5,681,282 A | 10/1997 | Eggers et al. |
| 5,683,366 A | 11/1997 | Eggers et al. |
| 5,683,384 A | 11/1997 | Gough et al. |
| 5,687,723 A | 11/1997 | Avitall |
| 5,688,270 A | 11/1997 | Yates et al. |
| 5,693,045 A | 12/1997 | Eggers |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,927 A | 12/1997 | Imran et al. |
| 5,702,386 A | 12/1997 | Stern et al. |
| 5,709,680 A | 1/1998 | Yates et al. |
| 5,713,896 A | 2/1998 | Nardella |
| 5,718,241 A | 2/1998 | Ben-Haim et al. |
| 5,718,701 A | 2/1998 | Shai et al. |
| 5,718,703 A | 2/1998 | Chin |
| 5,722,400 A | 3/1998 | Ockuly et al. |
| 5,725,524 A | 3/1998 | Mulier et al. |
| 5,730,127 A | 3/1998 | Avitall |
| 5,735,846 A | 4/1998 | Panescu et al. |
| 5,743,903 A | 4/1998 | Stern et al. |
| 5,746,739 A | 5/1998 | Sutter |
| 5,749,869 A | 5/1998 | Lindenmeier et al. |
| 5,755,717 A | 5/1998 | Yates et al. |
| 5,755,753 A | 5/1998 | Knowlton |
| 5,766,153 A | 6/1998 | Eggers et al. |
| 5,766,167 A | 6/1998 | Eggers et al. |

| | | | | | | |
|---|---|---|---|---|---|---|
| 5,785,705 | A | 7/1998 | Baker | 6,019,757 | A | 2/2000 | Scheldrup |
| 5,785,706 | A | 7/1998 | Bednarek | 6,024,733 | A | 2/2000 | Eggers et al. |
| 5,792,140 | A | 8/1998 | Tu et al. | 6,027,501 | A | 2/2000 | Goble et al. |
| 5,797,905 | A | 8/1998 | Fleischman et al. | 6,030,379 | A | 2/2000 | Panescu et al. |
| 5,797,960 | A | 8/1998 | Stevens et al. | 6,032,077 | A | 2/2000 | Pomeranz |
| 5,800,413 | A | 9/1998 | Swartz et al. | 6,032,674 | A | 3/2000 | Eggers et al. |
| 5,800,482 | A | 9/1998 | Pomeranz et al. | 6,033,398 | A | 3/2000 | Farley et al. |
| 5,807,393 | A | 9/1998 | Williamson et al. | 6,035,238 | A | 3/2000 | Ingle et al. |
| 5,807,395 | A | 9/1998 | Mulier et al. | 6,036,687 | A | 3/2000 | Laufer et al. |
| 5,810,764 | A | 9/1998 | Eggers et al. | 6,045,532 | A | 4/2000 | Eggers et al. |
| 5,810,805 | A | 9/1998 | Sutcu et al. | 6,047,700 | A | 4/2000 | Eggers et al. |
| 5,810,811 | A | 9/1998 | Yates et al. | 6,048,333 | A | 4/2000 | Lennox et al. |
| 5,817,093 | A | 10/1998 | Williamson et al. | 6,053,172 | A | 4/2000 | Hovda et al. |
| 5,823,956 | A | 10/1998 | Roth et al. | 6,053,912 | A | 4/2000 | Panescu et al. |
| 5,827,271 | A | 10/1998 | Buysse et al. | 6,056,744 | A | 5/2000 | Edwards |
| 5,827,281 | A | 10/1998 | Levin | 6,056,745 | A | 5/2000 | Panescu et al. |
| 5,833,703 | A | 11/1998 | Manushakian | 6,056,747 | A | 5/2000 | Saadat et al. |
| 5,843,019 | A | 12/1998 | Eggers et al. | 6,059,781 | A | 5/2000 | Yamanashi et al. |
| 5,843,021 | A | 12/1998 | Edwards et al. | 6,063,079 | A | 5/2000 | Hovda et al. |
| 5,843,078 | A | 12/1998 | Sharkey | 6,063,081 | A | 5/2000 | Mulier et al. |
| 5,843,152 | A | 12/1998 | Tu et al. | 6,066,134 | A | 5/2000 | Eggers et al. |
| 5,855,614 | A | 1/1999 | Stevens et al. | 6,066,139 | A | 5/2000 | Ryan et al. |
| 5,860,951 | A | 1/1999 | Eggers et al. | 6,068,627 | A | 5/2000 | Orszulak et al. |
| 5,860,974 | A | 1/1999 | Abele | 6,068,653 | A | 5/2000 | LaFontaine |
| 5,861,002 | A | 1/1999 | Desai | 6,071,280 | A | 6/2000 | Edwards et al. |
| 5,861,021 | A | 1/1999 | Thome et al. | 6,073,051 | A | 6/2000 | Sharkey et al. |
| 5,868,739 | A | 2/1999 | Lindenmeier et al. | 6,074,389 | A | 6/2000 | Levine et al. |
| 5,871,469 | A | 2/1999 | Eggers et al. | 6,080,151 | A | 6/2000 | Swartz et al. |
| 5,871,524 | A | 2/1999 | Knowlton | 6,081,749 | A | 6/2000 | Ingle et al. |
| 5,873,855 | A | 2/1999 | Eggers et al. | 6,083,237 | A | 7/2000 | Huitema et al. |
| 5,876,398 | A | 3/1999 | Mulier et al. | 6,086,585 | A | 7/2000 | Hovda et al. |
| 5,888,198 | A | 3/1999 | Eggers et al. | 6,086,586 | A | 7/2000 | Hooven |
| 5,891,095 | A | 4/1999 | Eggers et al. | 6,091,995 | A | 7/2000 | Ingle et al. |
| 5,891,141 | A | 4/1999 | Rydell | 6,093,186 | A | 7/2000 | Goble |
| 5,891,142 | A | 4/1999 | Eggers et al. | 6,095,149 | A | 8/2000 | Sharkey et al. |
| 5,893,848 | A | 4/1999 | Negus et al. | 6,096,037 | A | 8/2000 | Mulier et al. |
| 5,895,355 | A | 4/1999 | Schaer | 6,099,514 | A | 8/2000 | Sharkey et al. |
| 5,895,417 | A | 4/1999 | Pomeranz et al. | 6,102,046 | A | 8/2000 | Weinstein et al. |
| 5,897,553 | A | 4/1999 | Mulier et al. | 6,105,581 | A | 8/2000 | Eggers et al. |
| 5,902,272 | A | 5/1999 | Eggers et al. | 6,109,268 | A | 8/2000 | Thapliyal et al. |
| 5,902,328 | A | 5/1999 | LaFontaine et al. | 6,113,596 | A | 9/2000 | Hooven et al. |
| 5,904,711 | A | 5/1999 | Flom et al. | 6,113,597 | A | 9/2000 | Eggers et al. |
| 5,906,613 | A | 5/1999 | Mulier et al. | 6,117,109 | A | 9/2000 | Eggers et al. |
| 5,913,854 | A | 6/1999 | Maguire et al. | 6,122,549 | A | 9/2000 | Sharkey et al. |
| 5,913,856 | A | 6/1999 | Chia et al. | H1904 | H | 10/2000 | Yates et al. |
| 5,919,191 | A | 7/1999 | Lennox et al. | 6,126,682 | A | 10/2000 | Sharkey et al. |
| 5,919,219 | A | 7/1999 | Knowlton | 6,135,999 | A | 10/2000 | Fanton et al. |
| 5,921,982 | A | 7/1999 | Lesh et al. | 6,141,576 | A | 10/2000 | Littmann et al. |
| 5,921,983 | A | 7/1999 | Shannon, Jr. | 6,142,992 | A | 11/2000 | Cheng et al. |
| 5,925,045 | A | 7/1999 | Reimels et al. | 6,149,620 | A | 11/2000 | Baker et al. |
| 5,935,123 | A | 8/1999 | Edwards et al. | 6,159,194 | A | 12/2000 | Eggers et al. |
| 5,948,011 | A | 9/1999 | Knowlton | 6,159,208 | A | 12/2000 | Hovda et al. |
| 5,951,549 | A | 9/1999 | Richardson et al. | 6,165,169 | A | 12/2000 | Panescu et al. |
| 5,954,716 | A | 9/1999 | Sharkey et al. | 6,165,175 | A | 12/2000 | Wampler et al. |
| 5,957,919 | A | 9/1999 | Laufer | 6,168,594 | B1 | 1/2001 | LaFontaine et al. |
| 5,964,755 | A | 10/1999 | Edwards | 6,171,275 | B1 | 1/2001 | Webster, Jr. |
| 5,971,983 | A | 10/1999 | Lesh | 6,174,308 | B1 | 1/2001 | Goble et al. |
| 5,976,128 | A | 11/1999 | Schilling et al. | 6,174,309 | B1 | 1/2001 | Wrubleski et al. |
| 5,980,504 | A | 11/1999 | Sharkey et al. | 6,176,857 | B1 | 1/2001 | Ashley |
| 5,980,516 | A | 11/1999 | Mulier et al. | 6,179,824 | B1 | 1/2001 | Eggers et al. |
| 5,989,248 | A | 11/1999 | Tu et al. | 6,179,836 | B1 | 1/2001 | Eggers et al. |
| 5,992,418 | A | 11/1999 | de la Rama et al. | 6,183,469 | B1 | 2/2001 | Thapliyal et al. |
| 5,993,412 | A | 11/1999 | Deily et al. | 6,190,381 | B1 | 2/2001 | Olsen et al. |
| 6,003,517 | A | 12/1999 | Sheffield et al. | 6,190,384 | B1 | 2/2001 | Ouchi |
| 6,004,316 | A | 12/1999 | Laufer | 6,193,715 | B1 | 2/2001 | Wrubleski et al. |
| 6,004,319 | A | 12/1999 | Goble et al. | 6,193,716 | B1 | 2/2001 | Shannon, Jr. |
| 6,007,570 | A | 12/1999 | Sharkey et al. | 6,203,542 | B1 | 3/2001 | Ellsberry et al. |
| 6,010,500 | A | 1/2000 | Sherman et al. | 6,210,402 | B1 | 4/2001 | Olsen et al. |
| 6,015,391 | A | 1/2000 | Rishton et al. | 6,210,410 | B1 | 4/2001 | Farin et al. |
| 6,015,407 | A | 1/2000 | Rieb et al. | 6,210,411 | B1 | 4/2001 | Hofmann et al. |
| 6,016,809 | A | 1/2000 | Mulier et al. | 6,212,426 | B1 | 4/2001 | Swanson |
| 6,017,338 | A | 1/2000 | Brucker et al. | 6,216,704 | B1 | 4/2001 | Ingle et al. |
| 6,018,676 | A | 1/2000 | Davis et al. | 6,217,576 | B1 | 4/2001 | Tu et al. |

| Patent No. | Date | Inventor |
|---|---|---|
| 6,221,039 B1 | 4/2001 | Durgin et al. |
| 6,221,069 B1 | 4/2001 | Daikuzono |
| 6,224,592 B1 | 5/2001 | Eggers et al. |
| 6,224,593 B1 | 5/2001 | Ryan et al. |
| 6,226,554 B1 | 5/2001 | Tu et al. |
| 6,228,078 B1 | 5/2001 | Eggers et al. |
| 6,228,082 B1 | 5/2001 | Baker et al. |
| 6,231,591 B1 | 5/2001 | Desai |
| 6,235,020 B1 | 5/2001 | Cheng et al. |
| 6,236,891 B1 | 5/2001 | Ingle et al. |
| 6,238,387 B1 | 5/2001 | Miller, III |
| 6,238,391 B1 | 5/2001 | Olsen et al. |
| 6,238,393 B1 | 5/2001 | Mulier et al. |
| 6,241,753 B1 | 6/2001 | Knowlton |
| 6,241,754 B1 | 6/2001 | Swanson et al. |
| 6,251,110 B1 | 6/2001 | Wampler |
| 6,254,600 B1 | 7/2001 | Willink et al. |
| 6,258,086 B1 | 7/2001 | Ashley et al. |
| 6,258,087 B1 | 7/2001 | Edwards et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,654 B1 | 7/2001 | Swartz et al. |
| 6,266,551 B1 | 7/2001 | Osadchy et al. |
| 6,277,112 B1 | 8/2001 | Underwood et al. |
| 6,280,440 B1 | 8/2001 | Gocho |
| 6,283,961 B1 | 9/2001 | Underwood et al. |
| 6,283,988 B1 | 9/2001 | Laufer et al. |
| 6,283,989 B1 | 9/2001 | Laufer et al. |
| 6,290,715 B1 | 9/2001 | Sharkey et al. |
| 6,293,942 B1 | 9/2001 | Goble et al. |
| 6,293,945 B1 | 9/2001 | Parins et al. |
| 6,296,636 B1 | 10/2001 | Cheng et al. |
| 6,296,638 B1 | 10/2001 | Davison et al. |
| 6,296,640 B1 | 10/2001 | Wampler et al. |
| 6,299,633 B1 | 10/2001 | Laufer |
| 6,302,903 B1 | 10/2001 | Mulier et al. |
| 6,306,134 B1 | 10/2001 | Goble et al. |
| 6,309,387 B1 | 10/2001 | Eggers et al. |
| 6,311,090 B1 | 10/2001 | Knowlton |
| 6,312,408 B1 | 11/2001 | Eggers et al. |
| 6,312,430 B1 | 11/2001 | Wilson et al. |
| 6,315,777 B1 | 11/2001 | Comben |
| 6,322,549 B1 | 11/2001 | Eggers et al. |
| 6,322,559 B1 | 11/2001 | Daulton et al. |
| 6,327,505 B1 | 12/2001 | Medhkour et al. |
| 6,328,735 B1 | 12/2001 | Curley et al. |
| 6,328,736 B1 | 12/2001 | Mulier et al. |
| 6,336,926 B1 | 1/2002 | Goble |
| 6,350,262 B1 | 2/2002 | Ashley |
| 6,350,276 B1 | 2/2002 | Knowlton |
| 6,352,533 B1 | 3/2002 | Ellman et al. |
| 6,355,032 B1 | 3/2002 | Hovda et al. |
| 6,358,245 B1 | 3/2002 | Edwards et al. |
| 6,358,248 B1 | 3/2002 | Mulier et al. |
| 6,363,937 B1 | 4/2002 | Hovda et al. |
| 6,371,956 B1 | 4/2002 | Wilson et al. |
| 6,379,350 B1 | 4/2002 | Sharkey et al. |
| 6,379,351 B1 | 4/2002 | Thapliyal et al. |
| 6,391,025 B1 | 5/2002 | Weinstein et al. |
| 6,391,028 B1 | 5/2002 | Fanton et al. |
| 6,402,742 B1 | 6/2002 | Blewett et al. |
| 6,409,722 B1 | 6/2002 | Hoey et al. |
| 6,409,723 B1 | 6/2002 | Edwards |
| H2037 H | 7/2002 | Yates et al. |
| 6,416,507 B1 | 7/2002 | Eggers et al. |
| 6,416,508 B1 | 7/2002 | Eggers et al. |
| 6,416,509 B1 | 7/2002 | Goble et al. |
| 6,425,877 B1 | 7/2002 | Edwards |
| 6,432,103 B1 | 8/2002 | Ellsberry et al. |
| 6,440,130 B1 | 8/2002 | Mulier et al. |
| 6,443,952 B1 | 9/2002 | Mulier et al. |
| 6,451,017 B1 | 9/2002 | Moutafis et al. |
| 6,458,123 B1 | 10/2002 | Brucker et al. |
| 6,458,130 B1 | 10/2002 | Frazier et al. |
| 6,461,350 B1 | 10/2002 | Underwood et al. |
| 6,461,354 B1 | 10/2002 | Olsen et al. |
| 6,461,357 B1 | 10/2002 | Sharkey et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,275 B1 | 10/2002 | Wampler et al. |
| 6,471,698 B1 | 10/2002 | Edwards et al. |
| 6,475,216 B2 | 11/2002 | Mulier et al. |
| 6,478,793 B1 | 11/2002 | Cosman et al. |
| 6,482,202 B1 | 11/2002 | Goble et al. |
| 6,485,490 B2 | 11/2002 | Wampler et al. |
| 6,488,680 B1 | 12/2002 | Francischelli et al. |
| 6,493,589 B1 | 12/2002 | Medhkour et al. |
| 6,494,902 B2 | 12/2002 | Hoey et al. |
| 6,497,705 B2 | 12/2002 | Comben |
| 6,506,189 B1 | 1/2003 | Rittman, III et al. |
| 6,508,815 B1 | 1/2003 | Strul et al. |
| 6,517,536 B2 * | 2/2003 | Hooven et al. ............... 606/41 |
| 6,526,320 B2 | 2/2003 | Mitchell |
| 6,537,248 B2 | 3/2003 | Mulier et al. |
| 6,537,272 B2 | 3/2003 | Christopherson et al. |
| 6,539,265 B2 | 3/2003 | Medhkour et al. |
| 6,558,379 B1 | 5/2003 | Batchelor et al. |
| 6,558,385 B1 | 5/2003 | McClurken et al. |
| 6,575,969 B1 | 6/2003 | Rittman, III et al. |
| 6,577,902 B1 | 6/2003 | Laufer et al. |
| 6,579,288 B1 | 6/2003 | Swanson et al. |
| 6,585,732 B2 | 7/2003 | Mulier et al. |
| 6,602,248 B1 | 8/2003 | Sharps et al. |
| 6,603,988 B2 | 8/2003 | Dowlatshahi |
| 6,610,060 B2 * | 8/2003 | Mulier et al. ............... 606/49 |
| 6,613,048 B2 | 9/2003 | Mulier et al. |
| 6,623,515 B2 | 9/2003 | Mulier et al. |
| 6,626,899 B2 | 9/2003 | Houser et al. |
| 6,645,202 B1 | 11/2003 | Pless et al. |
| 6,666,862 B2 | 12/2003 | Jain et al. |
| 6,669,692 B1 | 12/2003 | Nelson et al. |
| 6,676,660 B2 | 1/2004 | Wampler |
| 6,679,882 B1 | 1/2004 | Kornerup |
| 6,682,501 B1 | 1/2004 | Nelson et al. |
| 6,682,527 B2 | 1/2004 | Strul |
| 6,682,528 B2 | 1/2004 | Fraizer et al. |
| 6,685,700 B2 | 2/2004 | Behl et al. |
| 6,685,701 B2 | 2/2004 | Orszulak et al. |
| 6,685,704 B2 | 2/2004 | Greep |
| 6,689,129 B2 | 2/2004 | Baker |
| 6,689,131 B2 | 2/2004 | McClurken |
| 6,692,489 B1 | 2/2004 | Heim et al. |
| 6,694,984 B2 | 2/2004 | Habib |
| 6,695,837 B2 | 2/2004 | Howell |
| 6,695,840 B2 | 2/2004 | Schulze |
| 6,699,240 B2 | 3/2004 | Francischelli |
| 6,699,242 B2 | 3/2004 | Heggeness |
| 6,699,244 B2 | 3/2004 | Carranza et al. |
| 6,699,268 B2 | 3/2004 | Kordis et al. |
| 6,702,810 B2 | 3/2004 | McClurken et al. |
| 6,702,812 B2 | 3/2004 | Cosmescu |
| 6,706,039 B2 | 3/2004 | Mulier et al. |
| 6,712,074 B2 | 3/2004 | Edwards et al. |
| 6,712,811 B2 | 3/2004 | Underwood et al. |
| 6,712,813 B2 | 3/2004 | Ellman et al. |
| 6,712,816 B2 | 3/2004 | Hung et al. |
| 6,716,211 B2 | 4/2004 | Mulier et al. |
| 6,719,754 B2 | 4/2004 | Underwood et al. |
| 6,723,094 B1 | 4/2004 | Desinger |
| 6,726,683 B1 | 4/2004 | Shaw |
| 6,726,684 B1 | 4/2004 | Woloszko et al. |
| 6,726,686 B2 | 4/2004 | Buysse et al. |
| 6,730,081 B1 | 5/2004 | Desai |

| Patent | Type | Date | Inventor |
|---|---|---|---|
| 6,733,496 | B2 | 5/2004 | Sharkey et al. |
| 6,733,498 | B2 | 5/2004 | Paton et al. |
| 6,733,501 | B2 | 5/2004 | Levine |
| 6,736,810 | B2 | 5/2004 | Hoey et al. |
| 6,740,058 | B2 | 5/2004 | Lal et al. |
| 6,740,079 | B1 | 5/2004 | Eggers et al. |
| 6,740,082 | B2 | 5/2004 | Shadduck |
| 6,740,084 | B2 | 5/2004 | Ryan |
| 6,740,102 | B2 | 5/2004 | Hess et al. |
| 6,743,197 | B1 | 6/2004 | Edwards |
| 6,743,229 | B2 | 6/2004 | Buysse et al. |
| 6,743,230 | B2 | 6/2004 | Lutze et al. |
| 6,746,447 | B2 | 6/2004 | Davison et al. |
| 6,755,825 | B2 | 6/2004 | Shoenman et al. |
| 6,755,827 | B2 | 6/2004 | Mulier et al. |
| 6,757,565 | B2 | 6/2004 | Sharkey et al. |
| 6,758,846 | B2 | 7/2004 | Goble et al. |
| 6,761,718 | B2 | 7/2004 | Madsen |
| 6,764,487 | B2 | 7/2004 | Mulier et al. |
| 6,770,070 | B1 | 8/2004 | Balbierz |
| 6,770,071 | B2 | 8/2004 | Woloszko et al. |
| 6,770,072 | B1 | 8/2004 | Truckai et al. |
| 6,772,012 | B2 | 8/2004 | Ricart et al. |
| 6,772,013 | B1 | 8/2004 | Ingle et al. |
| 6,775,575 | B2 | 8/2004 | Bommannan et al. |
| 6,776,780 | B2 | 8/2004 | Mulier et al. |
| 6,780,177 | B2 | 8/2004 | Shafirstein et al. |
| 6,780,180 | B1 | 8/2004 | Goble et al. |
| 6,786,906 | B1 | 9/2004 | Cobb |
| 6,796,981 | B2 | 9/2004 | Wham et al. |
| 6,800,077 | B1 | 10/2004 | Mucko et al. |
| 6,802,842 | B2 | 10/2004 | Ellman et al. |
| 6,802,843 | B2 | 10/2004 | Truckai et al. |
| 6,808,525 | B2 | 10/2004 | Latterell et al. |
| 6,813,520 | B2 | 11/2004 | Truckai et al. |
| 6,814,714 | B1 | 11/2004 | Novak et al. |
| 6,814,731 | B2 | 11/2004 | Swanson |
| 6,821,273 | B2 | 11/2004 | Mollenauer |
| 6,827,713 | B2 | 12/2004 | Bek et al. |
| 6,827,725 | B2 | 12/2004 | Batchelor et al. |
| 6,832,997 | B2 | 12/2004 | Uchida et al. |
| 6,835,195 | B2 | 12/2004 | Schulze et al. |
| 6,836,688 | B2 | 12/2004 | Ingle et al. |
| 6,843,789 | B2 | 1/2005 | Goble |
| 6,845,264 | B1 | 1/2005 | Skladnev et al. |
| 6,849,073 | B2 | 2/2005 | Hoey et al. |
| 6,855,145 | B2 | 2/2005 | Ciarrocca |
| 6,858,028 | B2 | 2/2005 | Mulier et al. |
| 6,860,882 | B2 | 3/2005 | Battles et al. |
| 6,863,669 | B2 | 3/2005 | Spitzer |
| 6,864,686 | B2 | 3/2005 | Novak et al. |
| 6,881,214 | B2 | 4/2005 | Cosman et al. |
| 6,882,885 | B2 | 4/2005 | Levy, Jr. et al. |
| 6,887,237 | B2 | 5/2005 | McGaffigan |
| 6,887,240 | B1 | 5/2005 | Lands et al. |
| 6,893,435 | B2 | 5/2005 | Goble |
| 6,893,440 | B2 | 5/2005 | Durgin et al. |
| 6,896,672 | B1 | 5/2005 | Eggers et al. |
| 6,896,674 | B1 | 5/2005 | Woloszko et al. |
| 6,899,712 | B2 | 5/2005 | Moutafis et al. |
| 6,905,497 | B2 | 6/2005 | Truckai et al. |
| 6,905,499 | B1 | 6/2005 | Mucko et al. |
| 6,911,019 | B2 | 6/2005 | Mulier et al. |
| 6,915,806 | B2 | 7/2005 | Pacek et al. |
| 6,921,398 | B2 | 7/2005 | Carmel et al. |
| 6,921,399 | B2 | 7/2005 | Carmel et al. |
| 6,923,803 | B2 | 8/2005 | Goble |
| 6,923,805 | B1 | 8/2005 | LaFontaine et al. |
| 6,926,706 | B1 | 8/2005 | Sealfon |
| 6,926,716 | B2 | 8/2005 | Baker et al. |
| 6,926,717 | B1 | 8/2005 | Garito et al. |
| 6,929,640 | B1 | 8/2005 | Underwood et al. |
| 6,929,641 | B2 | 8/2005 | Goble et al. |
| 6,929,642 | B2 | 8/2005 | Xiao et al. |
| 6,929,644 | B2 | 8/2005 | Truckai et al. |
| 6,929,645 | B2 | 8/2005 | Battles et al. |
| 6,932,810 | B2 | 8/2005 | Ryan |
| 6,932,815 | B2 | 8/2005 | Sutter |
| 6,942,661 | B2 | 9/2005 | Swanson |
| 6,949,096 | B2 | 9/2005 | Davison et al. |
| 6,949,098 | B2 | 9/2005 | Mulier et al. |
| 6,951,559 | B1 | 10/2005 | Greep |
| 6,953,461 | B2 | 10/2005 | McClurken et al. |
| 6,960,204 | B2 | 11/2005 | Eggers et al. |
| 6,960,207 | B2 | 11/2005 | Vanney et al. |
| 6,960,210 | B2 | 11/2005 | Lands et al. |
| 6,962,589 | B2 | 11/2005 | Mulier et al. |
| 6,964,274 | B1 | 11/2005 | Ryan et al. |
| 6,964,661 | B2 | 11/2005 | Rioux et al. |
| 6,966,907 | B2 | 11/2005 | Goble |
| 6,966,909 | B2 | 11/2005 | Marshall et al. |
| 6,971,394 | B2 | 12/2005 | Sliwa, Jr. et al. |
| 6,974,452 | B1 | 12/2005 | Gille et al. |
| 6,974,453 | B2 | 12/2005 | Woloszko et al. |
| 6,979,332 | B2 | 12/2005 | Adams |
| 6,984,231 | B2 | 1/2006 | Goble et al. |
| 6,986,769 | B2 | 1/2006 | Nelson et al. |
| 6,991,631 | B2 | 1/2006 | Woloszko et al. |
| 7,001,380 | B2 | 2/2006 | Goble |
| 7,001,382 | B2 | 2/2006 | Gallo, Sr. |
| 7,004,941 | B2 | 2/2006 | Tvinnereim et al. |
| 7,004,942 | B2 | 2/2006 | Laird et al. |
| 7,008,419 | B2 | 3/2006 | Shadduck |
| 7,008,421 | B2 | 3/2006 | Daniel et al. |
| 7,033,348 | B2 | 4/2006 | Alfano et al. |
| 7,033,356 | B2 | 4/2006 | Latterell et al. |
| 7,041,096 | B2 | 5/2006 | Malis et al. |
| 7,041,101 | B2 | 5/2006 | Eggers |
| 7,041,102 | B2 | 5/2006 | Truckai et al. |
| 7,052,494 | B2 | 5/2006 | Goble et al. |
| 7,060,064 | B2 | 6/2006 | Allen et al. |
| 7,063,670 | B2 | 6/2006 | Sampson et al. |
| 7,066,932 | B1 | 6/2006 | Morgan et al. |
| 7,066,936 | B2 | 6/2006 | Ryan |
| 7,070,596 | B1 | 7/2006 | Woloszko et al. |
| 7,070,604 | B1 | 7/2006 | Garito et al. |
| 7,074,217 | B2 | 7/2006 | Strul et al. |
| 7,074,219 | B2 | 7/2006 | Levine et al. |
| 7,083,601 | B1 | 8/2006 | Cosmescu |
| 7,087,051 | B2 | 8/2006 | Bourne et al. |
| 7,087,053 | B2 | 8/2006 | Vanney |
| 7,094,215 | B2 | 8/2006 | Davison et al. |
| 7,101,387 | B2 | 9/2006 | Garabedian et al. |
| 7,104,986 | B2 | 9/2006 | Hovda et al. |
| 7,112,199 | B2 | 9/2006 | Cosmescu |
| 7,115,139 | B2 | 10/2006 | McClurken et al. |
| 7,125,406 | B2 | 10/2006 | Given |
| 7,147,634 | B2 | 12/2006 | Nesbitt |
| 7,147,635 | B2 | 12/2006 | Ciarrocca |
| 7,147,637 | B2 | 12/2006 | Goble |
| 7,147,638 | B2 | 12/2006 | Chapman et al. |
| 7,150,746 | B2 | 12/2006 | DeCesare et al. |
| 7,150,747 | B1 | 12/2006 | McDonald et al. |
| 7,150,748 | B2 | 12/2006 | Ebbutt et al. |
| 7,153,300 | B2 | 12/2006 | Goble |
| 7,156,845 | B2 | 1/2007 | Mulier et al. |
| 7,166,105 | B2 | 1/2007 | Mulier et al. |
| 7,166,106 | B2 | 1/2007 | Bartel et al. |
| 7,169,143 | B2 | 1/2007 | Eggers et al. |
| 7,169,144 | B2 | 1/2007 | Hoey et al. |
| 7,207,471 | B2 | 4/2007 | Heinrich et al. |
| 7,232,440 | B2 | 6/2007 | Dumbauld et al. |
| 7,247,155 | B2 | 7/2007 | Hoey et al. |
| 7,261,711 | B2 | 8/2007 | Mulier et al. |
| 7,309,325 | B2 | 12/2007 | Mulier et al. |
| 7,311,708 | B2 | 12/2007 | McClurken |

| | | |
|---|---|---|
| 7,322,974 B2 | 1/2008 | Swoyer et al. |
| 7,361,175 B2 | 4/2008 | Suslov |
| 7,364,579 B2 | 4/2008 | Mulier et al. |
| 2001/0014819 A1 | 8/2001 | Ingle et al. |
| 2001/0020167 A1 | 9/2001 | Woloszko et al. |
| 2001/0023365 A1 | 9/2001 | Medhkour et al. |
| 2001/0025178 A1 | 9/2001 | Mulier et al. |
| 2001/0032002 A1 | 10/2001 | McClurken et al. |
| 2001/0039419 A1 | 11/2001 | Francischelli et al. |
| 2001/0041921 A1 | 11/2001 | Mulier et al. |
| 2001/0051802 A1 | 12/2001 | Woloszko et al. |
| 2001/0051804 A1 | 12/2001 | Mulier et al. |
| 2002/0002393 A1 | 1/2002 | Mitchell |
| 2002/0010463 A1 | 1/2002 | Mulier et al. |
| 2002/0013582 A1 | 1/2002 | Mulier et al. |
| 2002/0016589 A1 | 2/2002 | Swartz et al. |
| 2002/0019628 A1 | 2/2002 | Comben |
| 2002/0022870 A1 | 2/2002 | Truckai et al. |
| 2002/0026186 A1 | 2/2002 | Woloszko et al. |
| 2002/0026187 A1 | 2/2002 | Swanson |
| 2002/0029036 A1 | 3/2002 | Goble et al. |
| 2002/0035361 A1 | 3/2002 | Houser et al. |
| 2002/0035387 A1 | 3/2002 | Mulier et al. |
| 2002/0049438 A1 | 4/2002 | Sharkey et al. |
| 2002/0049439 A1 | 4/2002 | Mulier et al. |
| 2002/0049483 A1 | 4/2002 | Knowlton |
| 2002/0058933 A1 | 5/2002 | Christopherson et al. |
| 2002/0058935 A1 | 5/2002 | Hoey et al. |
| 2002/0062123 A1 | 5/2002 | McClurken et al. |
| 2002/0095150 A1 | 7/2002 | Goble |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0115991 A1 | 8/2002 | Edwards |
| 2002/0115992 A1 | 8/2002 | Utley et al. |
| 2002/0120259 A1 | 8/2002 | Lettice et al. |
| 2002/0120260 A1 | 8/2002 | Morris et al. |
| 2002/0120261 A1 | 8/2002 | Morris et al. |
| 2002/0128650 A1 | 9/2002 | McClurken |
| 2002/0133148 A1 | 9/2002 | Daniel et al. |
| 2002/0151884 A1 | 10/2002 | Hoey et al. |
| 2002/0156511 A1 | 10/2002 | Habib |
| 2002/0161364 A1 | 10/2002 | Mulier et al. |
| 2002/0169446 A1 | 11/2002 | Mulier et al. |
| 2002/0177846 A1 | 11/2002 | Mulier et al. |
| 2002/0183733 A1 | 12/2002 | Mulier et al. |
| 2002/0188284 A1 | 12/2002 | To et al. |
| 2002/0193851 A1 | 12/2002 | Silverman et al. |
| 2002/0198524 A1 | 12/2002 | Mulier et al. |
| 2003/0004510 A1 | 1/2003 | Wham et al. |
| 2003/0032955 A1 | 2/2003 | Mulier et al. |
| 2003/0073989 A1 | 4/2003 | Hoey et al. |
| 2003/0114850 A1 | 6/2003 | McClurken et al. |
| 2003/0181902 A1 | 9/2003 | Mulier et al. |
| 2003/0204185 A1 | 10/2003 | Sherman et al. |
| 2003/0216733 A1 | 11/2003 | McClurken et al. |
| 2004/0015162 A1 | 1/2004 | McGaffigan |
| 2004/0015163 A1 | 1/2004 | Buysse et al. |
| 2004/0015215 A1 | 1/2004 | Fredricks et al. |
| 2004/0015216 A1 | 1/2004 | DeSisto |
| 2004/0015218 A1 | 1/2004 | Finch et al. |
| 2004/0019350 A1 | 1/2004 | O'Brien et al. |
| 2004/0024395 A1 | 2/2004 | Ellman et al. |
| 2004/0024396 A1 | 2/2004 | Eggers |
| 2004/0024398 A1 | 2/2004 | Hovda et al. |
| 2004/0024399 A1 | 2/2004 | Sharps et al. |
| 2004/0030327 A1 | 2/2004 | Golan |
| 2004/0030328 A1 | 2/2004 | Eggers et al. |
| 2004/0030330 A1 | 2/2004 | Brassell et al. |
| 2004/0030332 A1 | 2/2004 | Knowlton et al. |
| 2004/0030333 A1 | 2/2004 | Goble |
| 2004/0034340 A1 | 2/2004 | Biscup |
| 2004/0034346 A1 | 2/2004 | Stern et al. |
| 2004/0034349 A1 | 2/2004 | Kirwan, Jr. et al. |
| 2004/0034400 A1 | 2/2004 | Ingle et al. |
| 2004/0039429 A1 | 2/2004 | Daniel et al. |
| 2004/0044341 A1 | 3/2004 | Truckai et al. |
| 2004/0054363 A1 | 3/2004 | Vaska et al. |
| 2004/0054365 A1 | 3/2004 | Goble |
| 2004/0054366 A1 | 3/2004 | Davison et al. |
| 2004/0054369 A1 | 3/2004 | Nelson et al. |
| 2004/0054370 A1 | 3/2004 | Given |
| 2004/0059328 A1 | 3/2004 | Daniel et al. |
| 2004/0059363 A1 | 3/2004 | Alvarez et al. |
| 2004/0064023 A1 | 4/2004 | Ryan et al. |
| 2004/0064137 A1 | 4/2004 | Pellegrino et al. |
| 2004/0068306 A1 | 4/2004 | Shadduck |
| 2004/0068307 A1 | 4/2004 | Goble |
| 2004/0073205 A1 | 4/2004 | Treat et al. |
| 2004/0073208 A1 | 4/2004 | Sutter |
| 2004/0078034 A1 | 4/2004 | Acker et al. |
| 2004/0078037 A1 | 4/2004 | Batchelor et al. |
| 2004/0078038 A1 | 4/2004 | Desinger et al. |
| 2004/0082946 A1 | 4/2004 | Malis et al. |
| 2004/0082952 A1 | 4/2004 | Dycus et al. |
| 2004/0087937 A1 | 5/2004 | Eggers et al. |
| 2004/0087939 A1 | 5/2004 | Eggers et al. |
| 2004/0087940 A1 | 5/2004 | Jahns et al. |
| 2004/0087943 A1 | 5/2004 | Dycus et al. |
| 2004/0088029 A1 | 5/2004 | Yamamoto |
| 2004/0092925 A1 | 5/2004 | Rizoiu et al. |
| 2004/0092926 A1 | 5/2004 | Hoey et al. |
| 2004/0097919 A1 | 5/2004 | Wellman et al. |
| 2004/0102770 A1 | 5/2004 | Goble |
| 2004/0102824 A1 | 5/2004 | Sharkey et al. |
| 2004/0116923 A1 | 6/2004 | Desinger |
| 2004/0122420 A1 | 6/2004 | Amoah |
| 2004/0122423 A1 | 6/2004 | Dycus et al. |
| 2004/0122494 A1 | 6/2004 | Eggers et al. |
| 2004/0138654 A1 | 7/2004 | Goble |
| 2004/0138655 A1 | 7/2004 | McClurken et al. |
| 2004/0138657 A1 | 7/2004 | Bourne et al. |
| 2004/0143257 A1 | 7/2004 | Fuimaono |
| 2004/0143258 A1 | 7/2004 | Fuimaono |
| 2004/0143259 A1 | 7/2004 | Mulier et al. |
| 2004/0143263 A1 | 7/2004 | Schechter et al. |
| 2004/0147902 A1 | 7/2004 | McGuckin, Jr. et al. |
| 2004/0147916 A1 | 7/2004 | Baker |
| 2004/0147922 A1 | 7/2004 | Keppel |
| 2004/0147925 A1 | 7/2004 | Buysse et al. |
| 2004/0162552 A1 | 8/2004 | McClurken |
| 2004/0162554 A1 | 8/2004 | Lee et al. |
| 2004/0162557 A1 | 8/2004 | Tetzlaff et al. |
| 2004/0162572 A1 | 8/2004 | Sauer |
| 2004/0167508 A1 | 8/2004 | Wham et al. |
| 2004/0172111 A1 | 9/2004 | Hijii et al. |
| 2004/0176760 A1 | 9/2004 | Qiu |
| 2004/0176761 A1 | 9/2004 | Desinger |
| 2004/0176762 A1 | 9/2004 | Lawes et al. |
| 2004/0181219 A1 | 9/2004 | Goble et al. |
| 2004/0181250 A1 | 9/2004 | Adams et al. |
| 2004/0186469 A1 | 9/2004 | Woloszko et al. |
| 2004/0186470 A1 | 9/2004 | Goble et al. |
| 2004/0186535 A1 | 9/2004 | Knowlton |
| 2004/0193148 A1 | 9/2004 | Wham et al. |
| 2004/0193150 A1 | 9/2004 | Sharkey et al. |
| 2004/0193152 A1 | 9/2004 | Sutton et al. |
| 2004/0193211 A1 | 9/2004 | Voegele et al. |
| 2004/0199156 A1 | 10/2004 | Rioux et al. |
| 2004/0199160 A1 | 10/2004 | Slater |
| 2004/0206365 A1 | 10/2004 | Knowlton |
| 2004/0210213 A1 | 10/2004 | Fuimaono et al. |
| 2004/0210214 A1 | 10/2004 | Knowlton |
| 2004/0215181 A1 | 10/2004 | Christopherson et al. |
| 2004/0215182 A1 | 10/2004 | Lee |
| 2004/0215183 A1 | 10/2004 | Hoey et al. |

| Publication No. | Date | Inventor |
|---|---|---|
| 2004/0215184 A1 | 10/2004 | Eggers et al. |
| 2004/0215185 A1 | 10/2004 | Truckai et al. |
| 2004/0215188 A1 | 10/2004 | Mulier et al. |
| 2004/0215235 A1 | 10/2004 | Jackson et al. |
| 2004/0215296 A1 | 10/2004 | Ganz et al. |
| 2004/0220561 A1 | 11/2004 | Kirwan, Jr. et al. |
| 2004/0220562 A1 | 11/2004 | Garabedian et al. |
| 2004/0225288 A1 | 11/2004 | Buysse et al. |
| 2004/0230190 A1 | 11/2004 | Dahla et al. |
| 2004/0236322 A1 | 11/2004 | Mulier et al. |
| 2004/0236324 A1 | 11/2004 | Muller et al. |
| 2004/0243125 A1 | 12/2004 | Dycus et al. |
| 2004/0243163 A1 | 12/2004 | Casiano et al. |
| 2004/0249371 A1 | 12/2004 | Dycus et al. |
| 2004/0249374 A1 | 12/2004 | Tetzlaff et al. |
| 2004/0249425 A1 | 12/2004 | Roy et al. |
| 2004/0260279 A1 | 12/2004 | Goble et al. |
| 2004/0260280 A1 | 12/2004 | Sartor |
| 2004/0260368 A1 | 12/2004 | Ingle et al. |
| 2005/0010205 A1 | 1/2005 | Hovda et al. |
| 2005/0010212 A1 | 1/2005 | McClurken et al. |
| 2005/0015085 A1 | 1/2005 | McClurken et al. |
| 2005/0015086 A1 | 1/2005 | Platt |
| 2005/0015130 A1 | 1/2005 | Gill |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0033292 A1 | 2/2005 | Teitelbaum et al. |
| 2005/0038471 A1 | 2/2005 | Chan et al. |
| 2005/0043728 A1 | 2/2005 | Ciarrocca |
| 2005/0049583 A1 | 3/2005 | Swanson |
| 2005/0049586 A1 | 3/2005 | Daniel et al. |
| 2005/0055019 A1 | 3/2005 | Skarda |
| 2005/0055020 A1 | 3/2005 | Skarda |
| 2005/0059966 A1 | 3/2005 | McClurken et al. |
| 2005/0070888 A1 | 3/2005 | Dimatteo et al. |
| 2005/0070891 A1 | 3/2005 | DeSisto |
| 2005/0070894 A1 | 3/2005 | McClurken |
| 2005/0070896 A1 | 3/2005 | Daniel et al. |
| 2005/0080410 A1 | 4/2005 | Rioux et al. |
| 2005/0080413 A1 | 4/2005 | Canady |
| 2005/0085804 A1 | 4/2005 | McGaffigan |
| 2005/0085809 A1 | 4/2005 | Mucko et al. |
| 2005/0085880 A1 | 4/2005 | Truckai et al. |
| 2005/0090816 A1 | 4/2005 | McClurken et al. |
| 2005/0090819 A1 | 4/2005 | Goble |
| 2005/0096649 A1 | 5/2005 | Adams |
| 2005/0096651 A1 | 5/2005 | Truckai et al. |
| 2005/0101951 A1 | 5/2005 | Wham et al. |
| 2005/0101952 A1 | 5/2005 | Lands et al. |
| 2005/0101965 A1 | 5/2005 | Ryan |
| 2005/0107778 A1 | 5/2005 | Rioux et al. |
| 2005/0107779 A1 | 5/2005 | Ellman et al. |
| 2005/0107784 A1 | 5/2005 | Moses et al. |
| 2005/0107786 A1 | 5/2005 | Canady |
| 2005/0113820 A1 | 5/2005 | Goble et al. |
| 2005/0113825 A1 | 5/2005 | Cosmescu |
| 2005/0124987 A1 | 6/2005 | Goble |
| 2005/0130929 A1 | 6/2005 | Boyd |
| 2005/0131402 A1 | 6/2005 | Ciarrocca et al. |
| 2005/0137590 A1 | 6/2005 | Lawes et al. |
| 2005/0137662 A1 | 6/2005 | Morris et al. |
| 2005/0143729 A1 | 6/2005 | Francischelli et al. |
| 2005/0154385 A1 | 7/2005 | Heim et al. |
| 2005/0154433 A1 | 7/2005 | Levy, Jr. et al. |
| 2005/0159739 A1 | 7/2005 | Paul et al. |
| 2005/0159740 A1 | 7/2005 | Paul et al. |
| 2005/0159778 A1 | 7/2005 | Heinrich et al. |
| 2005/0159797 A1 | 7/2005 | Chandran et al. |
| 2005/0165444 A1 | 7/2005 | Hart et al. |
| 2005/0171524 A1 | 8/2005 | Stern et al. |
| 2005/0171526 A1 | 8/2005 | Rioux et al. |
| 2005/0171532 A1 | 8/2005 | Ciarrocca |
| 2005/0171533 A1 | 8/2005 | Latterell et al. |
| 2005/0171534 A1 | 8/2005 | Habib |
| 2005/0171583 A1 | 8/2005 | Mosher et al. |
| 2005/0177150 A1 | 8/2005 | Amoah et al. |
| 2005/0177209 A1 | 8/2005 | Leung et al. |
| 2005/0187543 A1 | 8/2005 | Underwood et al. |
| 2005/0187599 A1 | 8/2005 | Sharkey et al. |
| 2005/0203503 A1 | 9/2005 | Edwards et al. |
| 2005/0203504 A1 | 9/2005 | Wham et al. |
| 2005/0209591 A1 | 9/2005 | Sutter |
| 2005/0209621 A1 | 9/2005 | Gordon et al. |
| 2005/0222602 A1 | 10/2005 | Sutter et al. |
| 2005/0222611 A1 | 10/2005 | WeitKamp |
| 2005/0228372 A1 | 10/2005 | Truckai et al. |
| 2005/0245918 A1 | 11/2005 | Sliwa, Jr. et al. |
| 2005/0245921 A1 | 11/2005 | Strul et al. |
| 2005/0245922 A1 | 11/2005 | Goble |
| 2005/0245923 A1 | 11/2005 | Christopherson et al. |
| 2005/0250477 A1 | 11/2005 | Eastwood et al. |
| 2005/0251128 A1 | 11/2005 | Amoah |
| 2005/0251134 A1 | 11/2005 | Woloszko et al. |
| 2005/0256519 A1 | 11/2005 | Goble et al. |
| 2005/0261676 A1 | 11/2005 | Hall et al. |
| 2005/0261677 A1 | 11/2005 | Hall et al. |
| 2005/0267465 A1 | 12/2005 | Hillier et al. |
| 2005/0267467 A1 | 12/2005 | Paul et al. |
| 2005/0267468 A1 | 12/2005 | Truckai et al. |
| 2005/0267469 A1 | 12/2005 | Blocher |
| 2005/0273092 A1 | 12/2005 | G. et al. |
| 2005/0273097 A1 | 12/2005 | Ryan |
| 2005/0277915 A1 | 12/2005 | DeCesare et al. |
| 2005/0277916 A1 | 12/2005 | DeCesare et al. |
| 2005/0277917 A1 | 12/2005 | Garito et al. |
| 2005/0283147 A1 | 12/2005 | Yachi |
| 2005/0283148 A1 | 12/2005 | Janssen et al. |
| 2005/0283149 A1 | 12/2005 | Thorne et al. |
| 2005/0283150 A1 | 12/2005 | Moutafis et al. |
| 2005/0283151 A1 | 12/2005 | Ebbutt et al. |
| 2005/0288661 A1 | 12/2005 | Sauvageau et al. |
| 2005/0288665 A1 | 12/2005 | Woloszko |
| 2006/0004356 A1 | 1/2006 | Bilski et al. |
| 2006/0009760 A1 | 1/2006 | Mulier et al. |
| 2006/0009762 A1 | 1/2006 | Whayne |
| 2006/0015097 A1 | 1/2006 | Mulier et al. |
| 2006/0020265 A1 | 1/2006 | Ryan |
| 2006/0025765 A1 | 2/2006 | Landman et al. |
| 2006/0025766 A1 | 2/2006 | Heinrich et al. |
| 2006/0030912 A1 | 2/2006 | Eggers et al. |
| 2006/0036235 A1 | 2/2006 | Swoyer et al. |
| 2006/0036237 A1 | 2/2006 | Davison et al. |
| 2006/0036239 A1 | 2/2006 | Canady |
| 2006/0041254 A1 | 2/2006 | Francischelli et al. |
| 2006/0041255 A1 | 2/2006 | Eggers et al. |
| 2006/0047275 A1 | 3/2006 | Goble |
| 2006/0047280 A1 | 3/2006 | Goble et al. |
| 2006/0047331 A1 | 3/2006 | Lax et al. |
| 2006/0052770 A1 | 3/2006 | Mulier et al. |
| 2006/0064085 A1 | 3/2006 | Schechter et al. |
| 2006/0064101 A1 | 3/2006 | Arramon |
| 2006/0074411 A1 | 4/2006 | Carmel et al. |
| 2006/0074414 A1 | 4/2006 | Mulier et al. |
| 2006/0079872 A1 | 4/2006 | Eggleston |
| 2006/0079888 A1 | 4/2006 | Mulier et al. |
| 2006/0084968 A1 | 4/2006 | Truckai et al. |
| 2006/0095026 A1 | 5/2006 | Ricart et al. |
| 2006/0095031 A1 | 5/2006 | Ormsby |
| 2006/0095034 A1 | 5/2006 | Garito et al. |
| 2006/0095075 A1 | 5/2006 | Burkinshaw et al. |
| 2006/0095103 A1 | 5/2006 | Eggers et al. |
| 2006/0100619 A1 | 5/2006 | McClurken et al. |
| 2006/0106376 A1 | 5/2006 | Godara et al. |
| 2006/0106379 A1 | 5/2006 | O'Brien et al. |

| | | |
|---|---|---|
| 2006/0111705 A1 | 5/2006 | Janzen et al. |
| 2006/0111709 A1 | 5/2006 | Goble et al. |
| 2006/0111710 A1 | 5/2006 | Goble et al. |
| 2006/0111711 A1 | 5/2006 | Goble |
| 2006/0111741 A1 | 5/2006 | Nardella |
| 2006/0116675 A1 | 6/2006 | McClurken et al. |
| 2006/0122593 A1 | 6/2006 | Jun et al. |
| 2006/0129145 A1 | 6/2006 | Woloszko et al. |
| 2006/0129185 A1 | 6/2006 | Paternuosto |
| 2006/0142757 A1 | 6/2006 | Daniel et al. |
| 2006/0149225 A1 | 7/2006 | McClurken |
| 2006/0167446 A1 | 7/2006 | Pozzato |
| 2006/0167449 A1 | 7/2006 | Mulier et al. |
| 2006/0167451 A1 | 7/2006 | Cropper |
| 2006/0178667 A1 | 8/2006 | Sartor et al. |
| 2006/0178668 A1 | 8/2006 | Albritton, IV |
| 2006/0178670 A1 | 8/2006 | Woloszko et al. |
| 2006/0178699 A1 | 8/2006 | Surti |
| 2006/0184164 A1 | 8/2006 | Malis et al. |
| 2006/0184167 A1 | 8/2006 | Vaska et al. |
| 2006/0189977 A1 | 8/2006 | Allen et al. |
| 2006/0189979 A1 | 8/2006 | Esch et al. |
| 2006/0195079 A1 | 8/2006 | Eberl |
| 2006/0200123 A1 | 9/2006 | Ryan |
| 2006/0217700 A1 | 9/2006 | Garito et al. |
| 2006/0217701 A1 | 9/2006 | Young et al. |
| 2006/0217707 A1 | 9/2006 | Daniel et al. |
| 2006/0224154 A1 | 10/2006 | Shadduck et al. |
| 2006/0235286 A1 | 10/2006 | Stone et al. |
| 2006/0235377 A1 | 10/2006 | Earley et al. |
| 2006/0235379 A1 | 10/2006 | McClurken et al. |
| 2006/0241577 A1 | 10/2006 | Balbierz et al. |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0247614 A1 | 11/2006 | Sampson et al. |
| 2006/0259025 A1 | 11/2006 | Dahla |
| 2006/0259031 A1 | 11/2006 | Carmel et al. |
| 2006/0259070 A1 | 11/2006 | Livneh |
| 2006/0264927 A1 | 11/2006 | Ryan |
| 2006/0264929 A1 | 11/2006 | Goble et al. |
| 2006/0264931 A1 | 11/2006 | Chapman et al. |
| 2006/0271033 A1 | 11/2006 | Ein-Gal |
| 2006/0271036 A1 | 11/2006 | Garabedian et al. |
| 2006/0271042 A1 | 11/2006 | Latterell et al. |
| 2006/0276783 A1 | 12/2006 | Cosmescu |
| 2006/0276785 A1 | 12/2006 | Asahara et al. |
| 2007/0000501 A1 | 1/2007 | Wert et al. |
| 2007/0010812 A1 | 1/2007 | Mittelstein et al. |
| 2007/0016182 A1 | 1/2007 | Lipson et al. |
| 2007/0049920 A1 | 3/2007 | McClurken et al. |
| 2007/0093808 A1 | 4/2007 | Mulier et al. |
| 2007/0118114 A1 | 5/2007 | Miller et al. |
| 2007/0208332 A1 | 9/2007 | Mulier et al. |
| 2008/0015563 A1 | 1/2008 | Hoey et al. |
| 2008/0071270 A1 | 3/2008 | Desinger et al. |

FOREIGN PATENT DOCUMENTS

| | | |
|---|---|---|
| EP | 0 175 595 | 3/1986 |
| EP | 0 956 826 A2 | 11/1999 |
| EP | 1 095 627 A1 | 5/2001 |
| FR | 2 235 669 | 1/1975 |
| JP | 57-117843 | 7/1982 |
| JP | 5-092009 | 4/1993 |
| JP | 7-124245 | 5/1995 |
| WO | WO 94/26228 A1 | 11/1994 |
| WO | WO 97/05829 A1 | 2/1997 |
| WO | WO 98/19613 | 5/1998 |
| WO | WO 98/38932 A1 | 9/1998 |
| WO | WO 99/20213 A1 | 4/1999 |
| WO | WO 99/66850 | 12/1999 |
| WO | WO 00/78240 A1 | 12/2000 |
| WO | WO 01/00099 A1 | 1/2001 |
| WO | WO 01/28444 A1 | 4/2001 |
| WO | WO 01/60273 A1 | 8/2001 |
| WO | WO 01/80757 A2 | 11/2001 |
| WO | WO 01/82812 A1 | 11/2001 |
| WO | WO 02/11635 A1 | 2/2002 |
| WO | WO 02/17804 A2 | 3/2002 |
| WO | WO 03/096880 A2 | 11/2003 |
| WO | WO 2005/122938 A1 | 12/2005 |
| WO | WO 2006/062916 A2 | 6/2006 |
| WO | WO 2006/062939 A2 | 6/2006 |

* cited by examiner

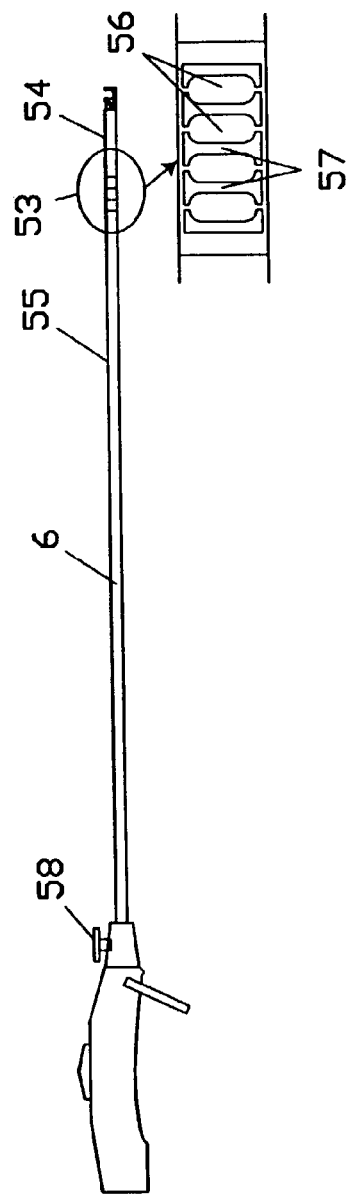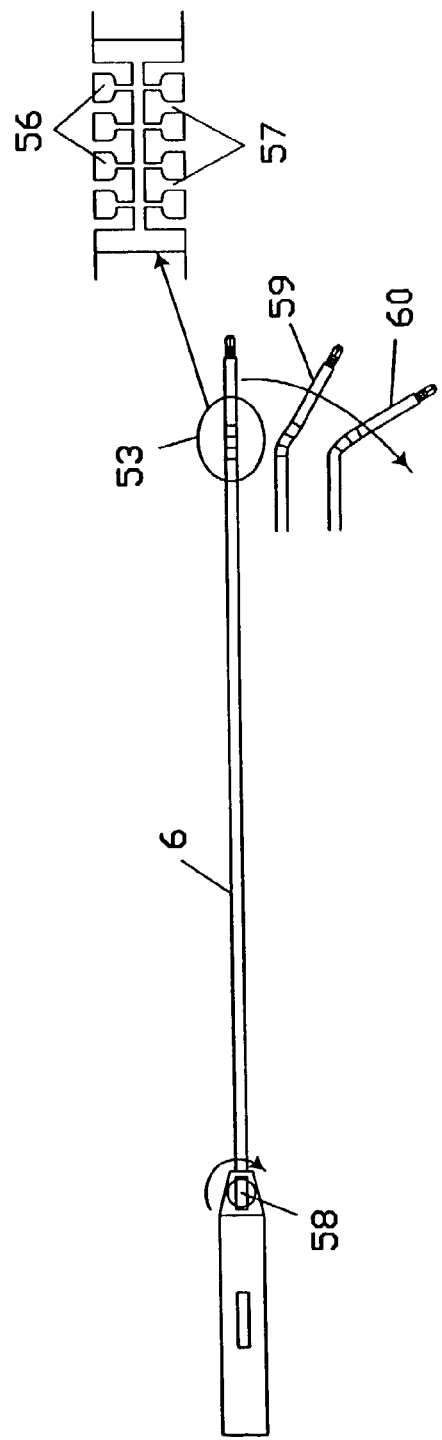

FLUID-ASSISTED MEDICAL DEVICE

This application is a continuation of application Ser. No. 09/668,403, filed Sep. 22, 2000 now U.S. Pat. No. 6,558,385, which application(s) are incorporated herein by reference.

FIELD OF THE INVENTION

This invention relates generally to the field of devices for use in surgery upon tissues of the body. More particularly, the invention relates to an electrosurgical device and methods of treatment of body tissues.

BACKGROUND OF THE INVENTION

Electrosurgical devices use electrical energy, most commonly radiofrequency (RF) energy, to cut tissue and/or cauterize blood vessels. During use, a voltage gradient is created at the tip of the device, thereby inducing current flow and related heat generation in the tissue. With sufficiently high levels of electrical energy, the heat generated is sufficient to cut the tissue and, advantageously, to cauterize severed blood vessels.

Current electrosurgical devices can cause the temperature of tissue being treated to rise significantly higher than 100° C., resulting in tissue desiccation, tissue sticking to the electrodes, tissue perforation, char formation and smoke generation. Peak tissue temperatures as a result of RF treatment of target tissue can be as high as 350° C., and such high temperatures may be transmitted to adjacent tissue via thermal diffusion. Undesirable results of such transmission to adjacent tissue include unintended thermal damage to the tissue.

One limitation of current electrosurgical devices arises from size constraints and dimensions. It is difficult to reach or gain access to some tissue and vessels due to anatomy and size constraints. Electrosurgical devices often have movable hinged scissors-like jaws at their tip that must open widely to be placed around the target tissue to be treated. Hinged jaws reduce visibility of the tip and often limit grasping capability of vessels due to force constraints. Further, devices currently used also often have long rigid shafts that cannot bend to maneuver around anatomical "tight" spots.

Laparoscopic or minimally-invasive surgery often involves multiple instrument passes through a trocar to achieve the desired tissue effect. Separate instruments are often required for coagulation and for cutting. Separate instruments may also be required to achieve surface hemostasis, such as when there is bleeding from the surface of an organ such as the liver. Multiple instrument passes are undesirable because they (1) waste valuable operating room time, (2) sometimes make it difficult to precisely relocate the target treatment site, (3) increase the risk of infection, and (4) increase the cost by increasing the number of different surgical instruments that are needed to complete the surgical procedure.

Accordingly, there is a need for a surgical device that reduces undesirable effects such as tissue desiccation and resulting tissue damage, char formation, smoke generation, and risk of infection, while at the same time providing improved accessibility to tissues and efficiency.

SUMMARY OF THE INVENTION

The invention provides an improved electrosurgical device for coagulating and cutting tissues of the body, utilizing the simultaneous infusion of a conductive solution and application of RF energy. This is accomplished with a device that includes a first electrode positioned on a first arm, and a second electrode positioned on a second arm, wherein at least one of the first arm or the second arm is translationally movable, and at least one of the first electrode or the second electrode is adapted to be coupled to a source of radiofrequency energy. The first arm and the second arm are coaxially arranged. In a preferred embodiment, the device comprises a housing having a proximal and a distal end; a tubular member having a proximal and a distal end, the tubular member extending from the distal end of the housing; a first, translationally movable arm extending from the distal end of the tubular member, the first arm including a first electrode; a second arm extending from the distal end of the tubular member, the second arm including a second electrode and being disposed coaxially with the first arm; at least one solution infusion opening on each electrode; and a solution delivery channel for delivery of a conductive solution to the solution infusion openings, wherein at least one of the first electrode or the second electrode is adapted to be coupled to a source of RF energy.

In a preferred embodiment, the first arm and second arm include at least one groove that surrounds the at least one solution infusion opening. Preferably, the groove(s) include spaced exit slots to allow conductive solution to exit the groove during use (e.g., when pressure is applied to tissues). The grooved arm serves to isolate the metal electrode from direct contact with bodily tissues being treated. Additionally, the grooved configuration provides constant spacing between the electrode and tissue to be treated. Further, the groove assists in preventing tissue pressure against the solution infusion openings during squeezing of the arms of the device, which could inhibit or reduce the flow of electrically conductive fluid locally.

Preferably, the device further comprises a translationally movable cutting mechanism to transect tissue after it has been coagulated. The device can also be used to achieve surface hemostasis with no special adjustments or removal of the instrument from the patient.

In a preferred embodiment, the device further includes a locking mechanism, to selectively lock one or both of the arms of the device in a desired position.

The invention also provides a corresponding method for treating tissues of the body, including, for example, blood vessels. The invention is useful for ligating and dividing a dorsal vein or other blood vessels that are located in deep cavities of the body, as well as for procedures involving polyp removal and laparoscopic tubal ligations.

The invention provides a combination of advantages. For example, the device provides conductive solution, such as saline, at the electrode-tissue interface to limit the peak tissue temperature, preferably to 100° C. or less. The provision of saline at the interface prevents tissue desiccation and the various effects of desiccation, such as tissue sticking to the electrodes, perforation of adjacent organs or tissue structures, char formation on electrodes and adjacent tissue, and smoke formation. The saline at the interface preferably maintains peak tissue temperature at or below 100° C. by (1) providing coupling of the electrode to the tissue with a wetted contact area that is much larger than that of a dry electrode, thus reducing current density and local RF heating near the electrode-tissue interface, (2) providing a convective cooling effect, such that the flowing liquid saline is heated by the warmer surface of RF-heated tissue, and (3) providing an evaporative cooling effect, such that excess RF power that cannot be conducted or convected away from the target tissue will be used to boil some fraction of the saline provided to the treatment surface.

The invention also provides an instrument that has a lower profile than standard coagulating forceps with hinged jaws. In a preferred embodiment, the device includes a tubular member that has an articulating or bending feature to enable the distal end effector region of the device, including first and second arms, to pass around anatomical features. According to the invention, the device is capable of being made with an outside diameter that is 25 mm or less. Preferably, the device is capable of being made with an outside diameter that is 15 mm or less, more preferably 5 mm or less. As used herein, the outside diameter is the maximum size that the tubular member or first and second arms achieve as a result of device operation.

The invention further provides a multi-purpose instrument that can be used to provide both coagulation and cutting of tissue without having to be removed from the patient's body. In one embodiment, the instrument is fabricated so that it is capable of sealing and cutting a vessel, as well as causing surface hemostasis on tissue such as bleeding liver.

BRIEF DESCRIPTION OF THE DRAWINGS

FIG. 29 is a side view of one embodiment of the invention, including an articulating tubular member.

FIG. 30 is a top view of the embodiment of FIG. 29.

DETAILED DESCRIPTION

The invention provides a medical device that comprises a first electrode and a second electrode, wherein the electrodes are disposed coaxially to each other, and at least one of the electrodes is translationally movable. Preferably, the first electrode is provided on a first arm, and the second electrode is provided on a second arm of the device. According to the invention, the device comprises at least one translationally movable arm that can be selectively movable to a fixed position. Preferably, the device includes a locking mechanism, to allow the operator to move at least one arm of the device to a desired position and lock the arm in that position. Each electrode is provided with conductive solution. In a preferred embodiment, the electrodes include at least one groove to assist in delivery of the conductive solution to tissue.

In a preferred embodiment, the invention provides a medical device comprising a housing having a proximal and a distal end; a tubular member having a proximal and a distal end, the tubular member extending from the distal end of the housing; a first, translationally movable arm extending from the distal end of the tubular member, the first arm including a first electrode; a second arm extending from the distal end of the tubular member, the second arm including a second electrode and being disposed coaxially with the first arm; at least one solution infusion opening on each electrode; and a solution delivery channel for delivery of solution to the solution infusion openings. The device is configured such at least one of the first and second arms is adapted to be coupled to a source of radiofrequency energy. The invention can be used to treat tissues of the body, including blood vessels and surfaces of organs, such as the liver. Although the invention will be described herein in relation to these mentioned applications, it is understood that the device has other applications as well, and these are considered within the scope of the invention.

In the present description, elements in common between the embodiments of the figures are numbered identically, and such elements need not be separately discussed.

Figure 1:
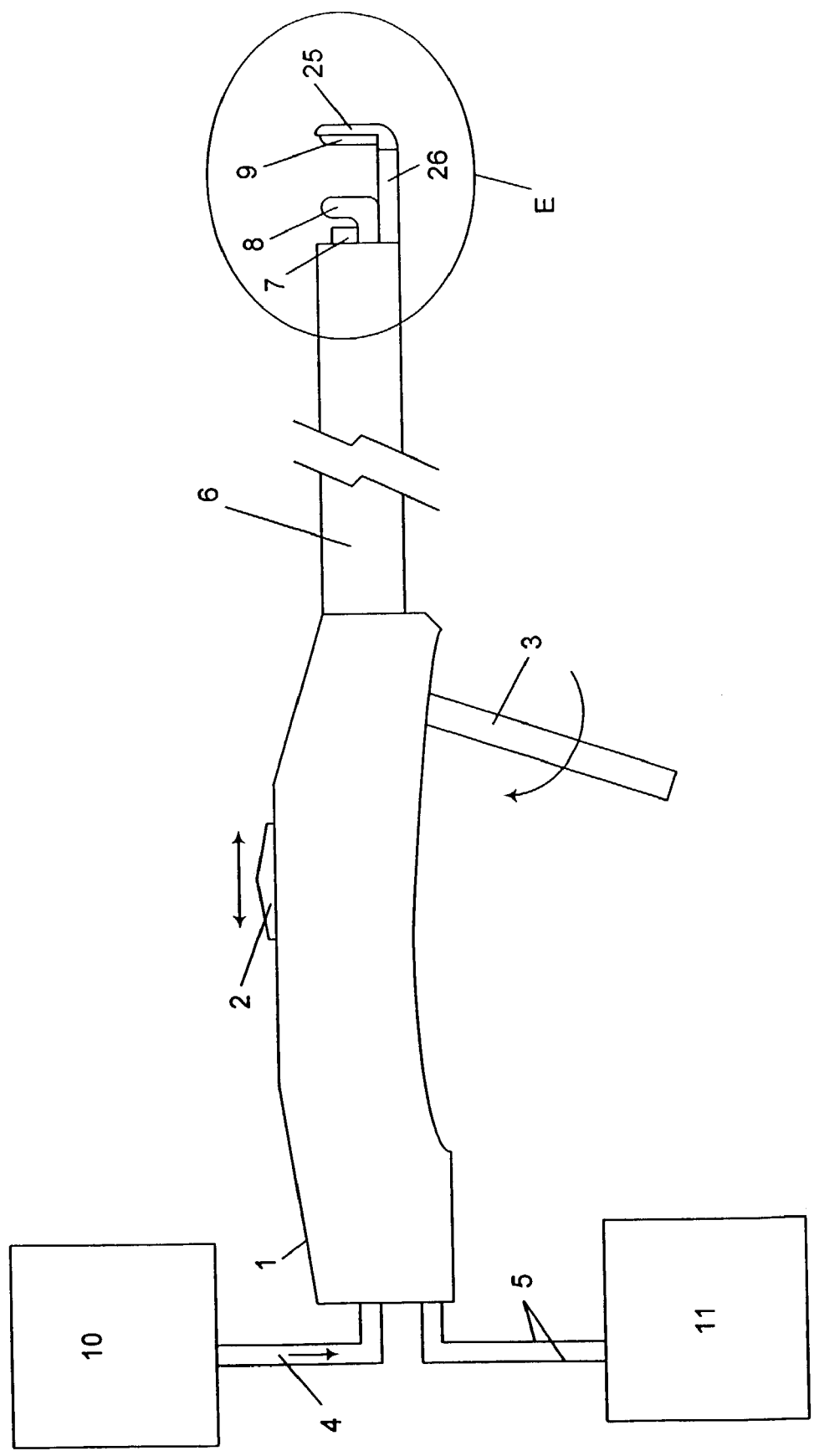
FIG. 1 is a side view of a device according to one embodiment of the invention.

One preferred embodiment of the device is illustrated in FIG. 1. As shown in FIG. 1, housing 1 of the device includes an actuation member 2 and a trigger 3. Extending from the distal end of the housing is tubular member 6. Extending from the distal end of the tubular member 6 are the first arm containing first electrode 8 and the second arm including second electrode 9, end portion 25, and platform portion 26. The first arm, second arm, and cutting mechanism 7 together comprise the end effector region E of the device. In a preferred embodiment, the cutting mechanism 7 is translationally movable, preferably independently from movement of the first and second arms. At the proximal end of the housing is located a solution supply tube 4, which delivers saline or other electrically conductive solution under pressure from a solution supply 10 to solution infusion openings located on the electrodes 8 and 9. Also at the proximal end of the housing are two conductors 5 that conduct RF from an RF generator 11 to the electrodes 8 and 9 of the device. Each component of the device will now be described in detail.

Referring to FIG. 1, a housing 1 includes two actuators, an actuation member 2 that controls the translational movement of at least one of the arms, and a trigger 3 that controls the translational movement of the cutting mechanism 7. As illustrated, in a typical operation, the actuation member 2 can be actuated by the thumb of the operator, whereas the trigger 3 can be actuated by the index finger of the operator. However, the precise configuration of the actuation member 2 and trigger 3 is not critical to the invention, and other configurations can be used to achieve translational movement of the cutting mechanism and arms, respectively. Preferably, the first and second arms are independently movable from the cutting mechanism, such that the operator can selectively move one or more arms of the device, the cutting mechanism, or all of these components, as desired.

Attached to the distal portion of the housing is the tubular member 6. The tubular member 6 includes a lumen through which the actuation rods for the arms and cutting mechanism, the solution delivery channel, and the conductors pass. Although the dimensions of the tubular member 6 can be adapted for a desired purpose, the tubular member is preferably long (approximately 10 to approximately 50 cm, preferably approximately 20 cm to approximately 40 cm, more preferably approximately 25 cm to approximately 35 cm), with a diameter of about 2 mm to about 20 mm, preferably about 3 mm to about 10 mm. In one embodiment, the tubular member 6 is circular in outer shape and rigid, so as to pass easily through a trocar. Alternatively, the tubular member 6 is malleable. In yet another embodiment, the tubular member includes a deflectable tip that can be controlled by the surgeon during use, e.g., by using a wire connected to the tip that can be pulled to deflect the tip to one side.

At the most distal end of the tubular member 6 is located the end effector region E, comprising a collection of components that function together to cause the desired tissue effects to occur. This end effector region E of components consists of the cutting mechanism 7, the first arm with first electrode 8 and the second arm with second electrode 9, and is shown circled in FIG. 1.

At the proximal portion of the housing is located the fluid supply tube 4, which contains saline or other electrically conductive solution such that the fluid flows into the solution supply channel in the housing from a source 10 such as an intravenous bag of solution hung from an intravenous (IV) pole, a pressurized elastomeric canister, a syringe pump, an intravenous volumetric infusion pump, or a peristaltic pump. Other configurations of supply sources can be provided, to achieve the purposes described herein. Also at the proximal portion of the housing are two wires 5, which are connected to a radiofrequency generator 11 such that electrical power is supplied to the device. It is contemplated that the device can include one cable that connects the radiofrequency generator to the electrodes of the device. The electrical connection can be made to be switched with a foot switch, a hand switch or both.

In one embodiment, the solution supply source 10 comprises a pressurized canister that can be adapted to be received within the housing 1, or it can be provided externally. When the solution supply source is received within the housing 1, the portion of the fluid supply tube that extends from the proximal portion of the housing can preferably be eliminated. In a further embodiment, the solution supply source can be attached to the exterior of the housing. The provision of the solution supply source as an internal component of the device, or as a component attachable to the exterior of the housing, thus preferably eliminates the "tethering" effect of a solution supply tube that runs from the proximal portion of the housing to an external supply source that is separate from the housing.

In yet another embodiment, the housing 1 may contain an electrical switch to turn the solution supply source on or off.

In still another embodiment, the housing 1 can contain a mechanical valve or flow control device, such that moving a linear or rotating piece from one position to another increases or decreases the flow resistance, and hence the flow rate of solution. Such a valve can be continuously adjustable or can be arranged to provide a series of pre-set levels of flow resistance such that the flow rate can be adjusted in fixed increments.

Additionally, the solution could be provided at a much higher "flush" rate that can be selected using an electrical switch located on the housing 1, or via a foot switch. Similarly, an additional tube can be provided to the distal region of the device to provide suction to rapidly remove accumulated blood, saline or other fluid in the operative site. In one embodiment, suction at the tip is activated by occluding a small circular opening located on the housing 1 (e.g., by virtue of the operator using a finger to cover the hole when suction is desired). With the suction always turned on, occluding the hole enables the suction "intake" to move from the hole in the housing to the tip of the device.

Figure 2:
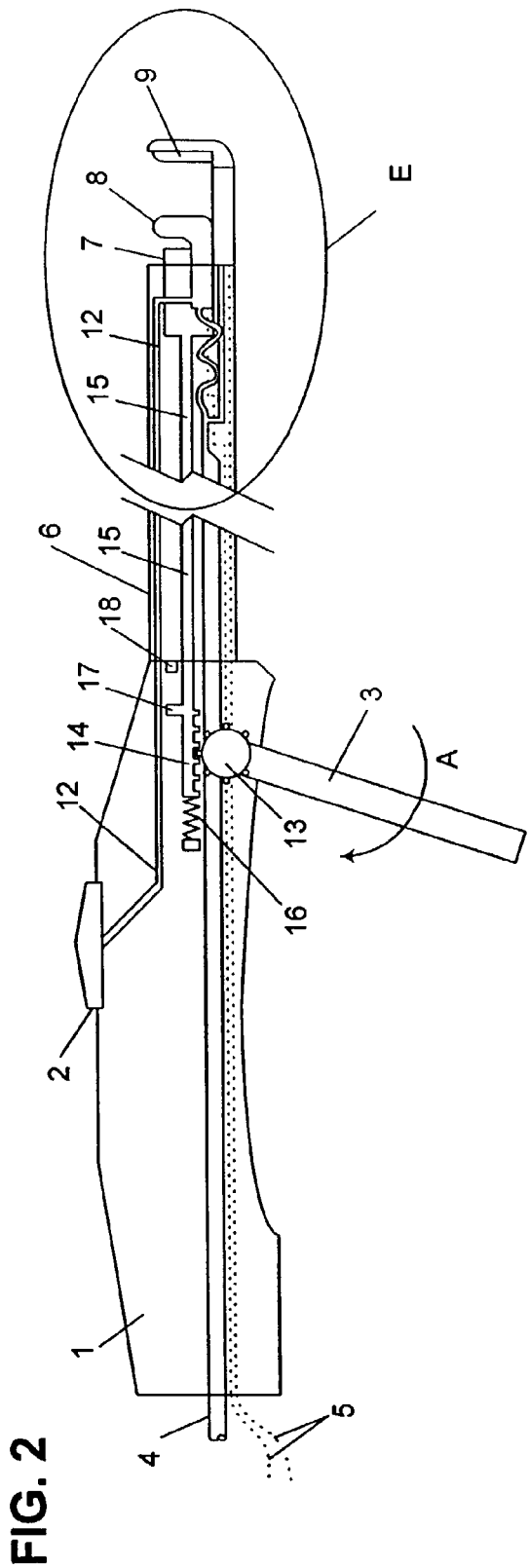
FIG. 2 is an open side view of the device of FIG. 1.

FIG. 2 shows an "open" side view of the device. "Open" in this context means that this is not precisely a cross-sectional view with cut-away faces of internal components. FIG. 2 illustrates one embodiment of how the actuators connect to components in the end effector of the device. Actuation member 2 is slidably disposed within a slot formed in the housing 1. Within the housing 1, the actuation member 2 is connected to a proximal end of an arm actuation rod 12, which runs from the actuation member within the housing and through the entire length of the tubular member 6.

In the embodiment shown in FIG. 2, at its distal end, the arm actuation rod 12 is connected to the first arm, which includes first electrode 8. Arm actuation rod 12 is connected to the first arm through crimping or other conventional connectors, or may be integrally formed with the first arm. Movement of the actuation member 2 in the distal direction causes corresponding distal movement of the arm actuation rod 12 within tubular member 6, which results in corresponding distal movement of the first arm; conversely, movement of the actuation member 2 in the proximal direction causes corresponding proximal movement of the arm actuation rod 12, which results in corresponding proximal movement of the first arm. As the first arm moves distally, it decreases the distance between the first arm and second arm, thereby compressing a blood vessel or other piece of tissue between the first arm and the second arm. In the embodiment shown, the second arm 9 is stationary.

With continuing reference to FIG. 2, cutting mechanism 7 is connected at is proximal end to cutting actuation rod 15 through crimping or other conventional connectors. The distal end of cutting actuation rod 15 is attached to cutting mechanism 7 by, for example, crimping, soldering, pinning, and the like, and the proximal end of the cutting actuation rod 15 is located within housing 1. At or near its proximal end, cutting actuation rod 15 includes gear rack 14. Trigger 3 is provided with pinion 13 that includes gear teeth which engage the gear rack 14. When trigger 3 is moved in the direction of arrow A, pinion 13 rotates and engages gear rack 14. The meshing of the gear teeth of pinion 13 and the gear rack 14 causes the cutting actuation rod 15 to move distally within tubular member 6. This, in turn, causes distal movement of cutting actuation rod 15, extending the cutting mechanism 7 distally from the device.

At its proximal end, gear rack 14 is operably connected to spring 16. Spring 16 is secured within housing 1 to anchor it in a desired location. Spring 16 serves to bias (e.g., push or force) cutting mechanism 7 proximally, thus returning the cutting mechanism 7 to a retracted position when trigger 3 is released, as shown in FIG. 2. Preferably, gear rack 14 further includes ridge 17, which serves as a limiter of distal cutting mechanism movement when it comes into contact with stop 18. Stop 18 is located within housing 1 at a position that is distal relative to gear rack 14. Thus, when trigger 3 is moved in the direction of arrow A, thereby rotating pinion 13 which engages gear rack 14, the gear rack 14, along with cutting actuation rod 15, moves in the distal direction. Distal movement of the gear rack 14 and cutting actuation rod 15 is stopped by contact of ridge 17 with stop 18. The purpose of the limiting mechanism described is to limit distal movement of the cutting mechanism 7, such that it does not come into contact with the second arm or second electrode, or extend distally beyond the second arm, thereby cutting tissue that may not be treated with the electrodes and thereby coagulated. It is to be understood that modifications to the limiter mechanism described herein can be made without departing from the invention. It is apparent that the gear ratio, not shown to scale, is described to close the electrodes with less than a 180° travel.

Tubular member 6 extends from the distal end of the housing 1. Tubular member 6 is preferably made from a non-conductive polymer material such as polycarbonate, LCP (liquid crystal polymer) or other extrudable material that has moderate to high temperature resistance. Alternatively, tubular member 6 is fabricated from a metal, such as stainless steel or the like, and coated with a polymer material mentioned above. Tubular member 6 includes a lumen, though which the cutting actuation rod 15, arm actuation rod 12, solution delivery channel 4 and conductors 5 pass. The outside diameter of tubular member 6 is preferably of a size for passing through a cannula and the length is sufficient to reach an internal blood vessel to be cauterized or tissue to be treated when the tubular member is slidably inserted through the cannula and into the body of a patient, as discussed above.

Tubular member 6 may be integrally formed with the housing 1, or it may be secured to housing 1 in a suitable manner, such as with adhesives, or using such techniques as press-fit, heat-staking or ultrasonic welding.

The device includes end effector region, as shown labeled in the figures as E, which will now be described in more detail. The device of the invention provides a first, translationally movable arm and a second arm that is disposed coaxially with the first arm. As used herein, "coaxially" means the first arm and second arm are configured in a side-by-side arrangement, so that the arms extend in a parallel manner from the distal end of the tubular member 6. As discussed herein, the first arm of the device includes first electrode 8, and the second arm includes a second electrode 9. Thus, as the first arm moves in the distal direction, it approaches the second arm of the device. As each arm includes its respective electrode, movement of the first arm, with its first electrode, towards the second arm, with its second electrode, allows the user to grasp tissue to be treated with the arms and apply RF energy to treat the tissue as desired.

Figure 3:
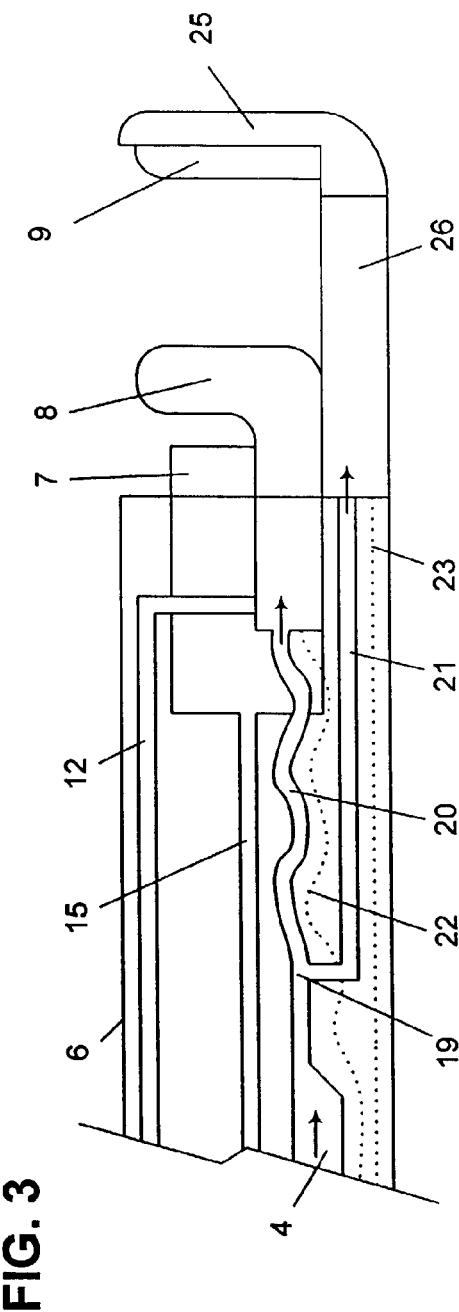
FIG. 3 is an enlarged side cross-sectional view of the distal end of the device of FIG. 1.

FIG. 3 illustrates an enlarged view of the end effector region E of one embodiment of the invention. The end effector region of the device includes the first arm including first electrode 8, the second arm including second electrode 9, and an optional cutting mechanism 7 (described in more detail below).

According to a preferred embodiment of the invention, each arm of the device is provided with its own solution delivery channel and conductor. As shown in FIG. 3, a solution delivery channel 4 is located within the tubular member 6. The solution delivery channel 4 extends from a solution source 10 at its proximal end, to the end effector region of the device at its distal end. In one embodiment, the device includes a separate solution delivery channel for each arm of the device. Alternatively, as shown in FIG. 3, the device includes a single solution delivery channel 4 that splits within the tube 6 toward the distal end of the tube. The "split" solution delivery channel thus forks to form first tube 20 that is in fluid communication with the first arm, and second tube 21 that is in fluid communication with the second arm. As shown in FIG. 3, first tube 20 is somewhat coiled and has slack in it so that when the first arm moves translationally, the first tube 20 can accommodate the motion without stretching or kinking. The precise configuration of solution delivery channel 4 is not critical, and it is understood that modifications can be made to the embodiment shown to supply conductive solution to the first arm and second arm of the device.

In addition to including a solution delivery channel, each arm of the device preferably includes a conductor for conducting RF energy from a source to the electrodes. As shown in FIG. 3, conductor 22 (shown in broken lines) is in communication with the first arm and thus first electrode 8, and conductor 23 (shown in broken lines) is in communication with the second arm and second electrode 9. The conductors 22, 23 are connected to a source of energy 11, such as RF energy, at their proximal ends. At their distal ends, each conductor is connected with an electrode of an arm of the end effector region E. Conductors 22 and 23 can be provided in the form of wires or other suitable conductive materials. As shown in FIG. 3, conductor 22 can be configured to include some coiling and slack to accommodate the translational movement of the first arm. Each of the conductors, 22 and 23, are preferably insulated by a sheath of non-conductive polymer such as Teflon™, with the insulation in place everywhere along the wires except where the wires are connected to other components, where the insulation is stripped to enable good crimps, solders or other connectors. Other suitable insulation can be applied to the conductors and their connections.

Figure 4:
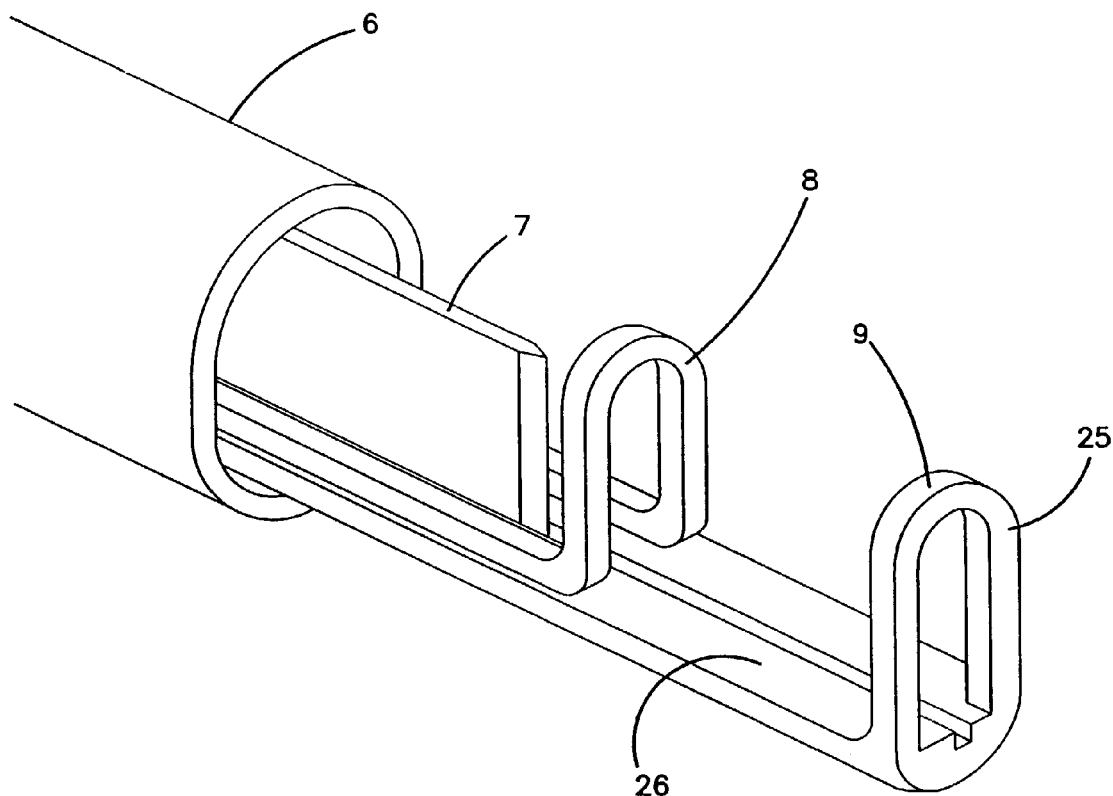
FIG. 4 is a perspective view of one embodiment of first and second electrodes of the invention.

FIG. 4 illustrates a perspective view of an embodiment of an end effector region of the device, including first and second electrodes, as well as a cutting mechanism. According to a preferred embodiment of the invention, the first and second electrodes, 8 and 9 respectively, are similar in shape and construction. Preferably, the first and second electrodes are substantially similar in size and dimensions. In one embodiment, for example, the first and second electrodes are provided in a 1:1 size ratio. In a preferred embodiment, each electrode has both an electrical connection and a solution connection, as discussed herein. One way to accomplish this is to use hollow stainless steel needle (e.g., hypodermic) tubing as the structural foundation of the electrode. As shown in FIG. 4, the electrode loop is similar to a rectangle which is bent up at one end. Preferably, when the electrode loop is bent, the angle formed by the bent loop is 90°. At the proximal end of the electrode, both the electrical and fluid connections are made. The electrical connection is made via a crimped or soldered connection of the inner braid of low resistance wire to the metal of the stainless steel tubing. The solution connection is such that the flow of electrically conductive fluid travels from a flexible polymer tubing (such as Tygon™ (PVC), Teflon™, and the like) to the stainless steel needle tubing. Once the electrical connection is made at the proximal end of the loop, electrical energy is conducted along the steel tubing without any significant loss in voltage or power. In the embodiment shown in FIG. 4, the conductive solution flows in both legs of the tubing, reaching the bent-up loop end where the solution leaves the metal tubing.

Figure 5:
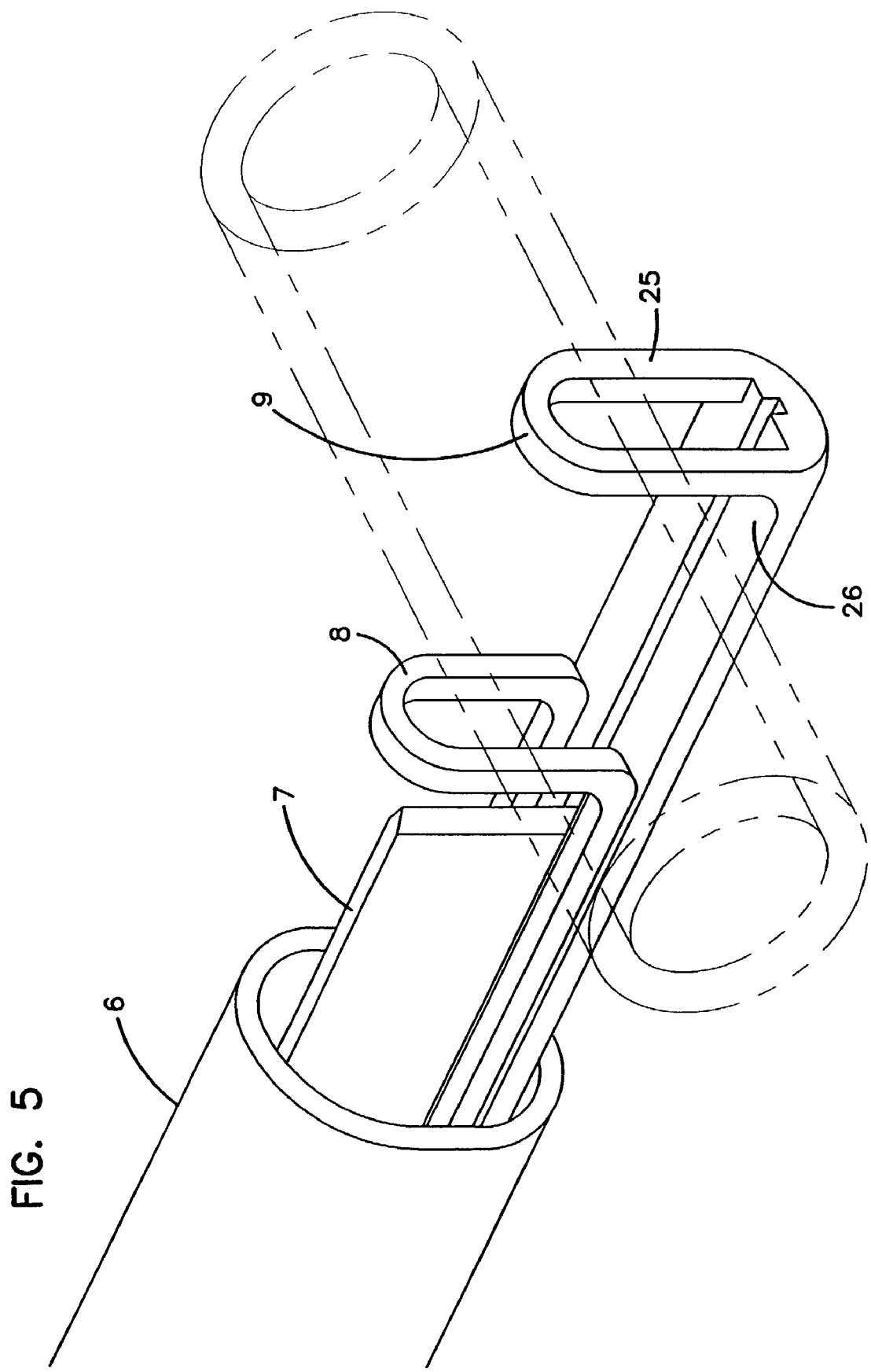
FIG. 5 is a perspective view showing the operation of the device of FIG. 4 at a surgical site.

FIG. 5 is another perspective view showing two electrodes along with a blood vessel to be treated, and a cutting mechanism 7. As shown, the first electrode 8 and second electrode 9 can be used to grasp a blood vessel, shown in broken lines (or other tissue), during treatment. As described herein, the cutting mechanism can move translationally, whereas either or both of the first arm containing the first electrode, and the second arm containing the second electrode, can be stationary or translationally movable, as desired. According to the invention, at least one arm of the device is translationally movable.

Figure 6:
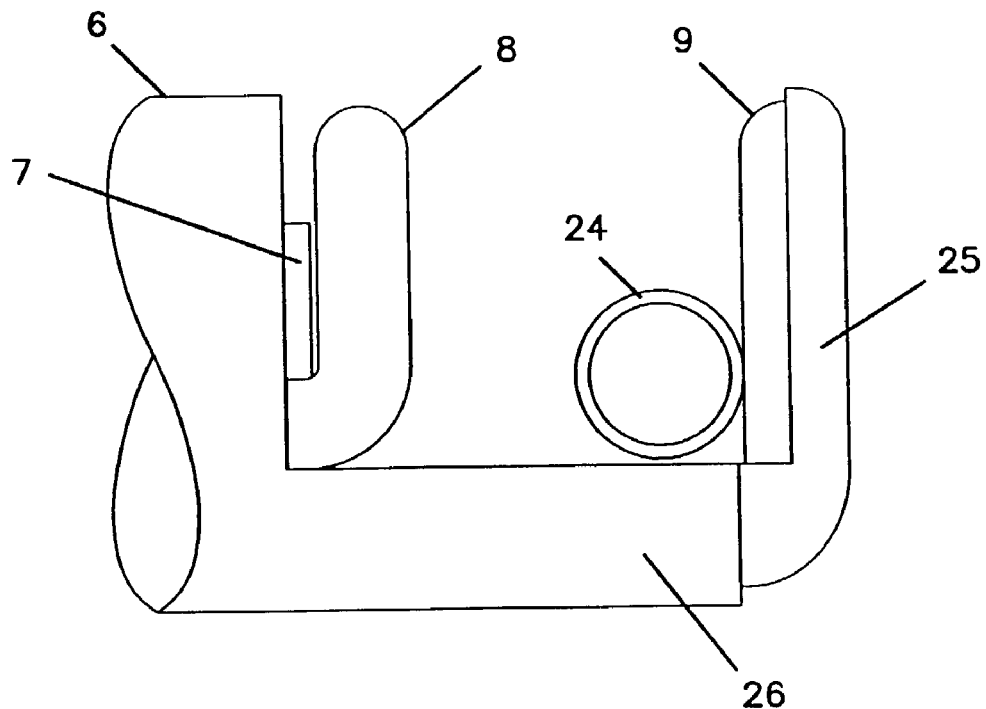
FIG. 6 is side view of the distal end of one embodiment of the invention.
Figure 7:
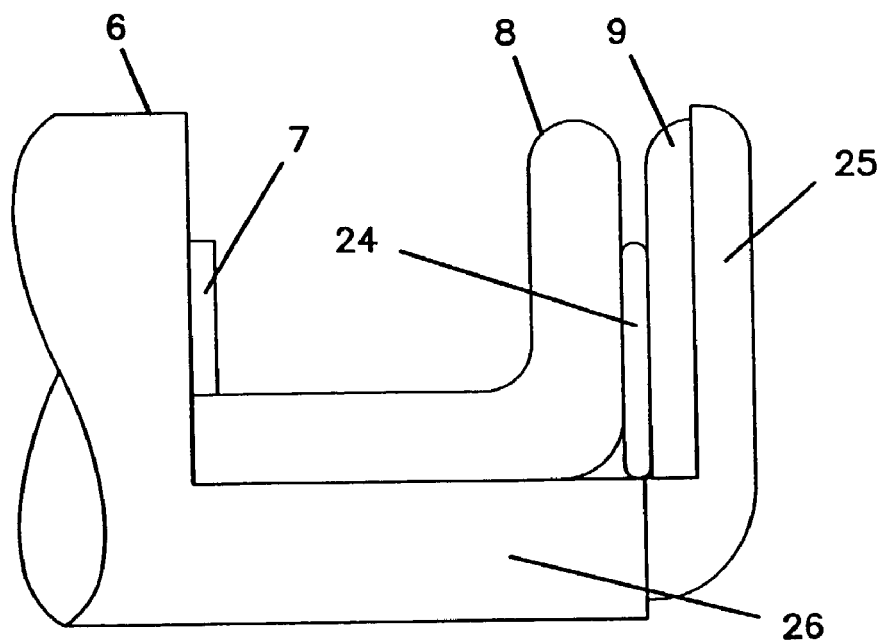
FIG. 7 is a side view of the embodiment shown in FIG. 6, demonstrating the operation of the device at a surgical site.

FIG. 6 shows a side view of the end effector region of the device, with the first arm and the cutting mechanism 7 both fully retracted (i.e., located at a proximal, unextended position). The second arm is shown including a portion of exposed metal 9, representing the second electrode, an end portion of the arm 25, and an underside, or platform portion 26. As shown in FIG. 6, the second electrode 9 is insulated and the end portion 25 and platform portion 26 of the second arm are both fabricated of non-electrically conductive polymer. End portion 25 and platform portion 26 together form a right angle in this embodiment. The tissue, such as a blood vessel, to be compressed and treated with RF is shown in cross-section as 24. FIG. 7 shows the embodiment of FIG. 6, wherein the first arm has been advanced distally to compress the vessel 24. FIGS. 6 and 7 show the cutting mechanism 7 in a retracted, or fully proximal, position.

Figure 8:
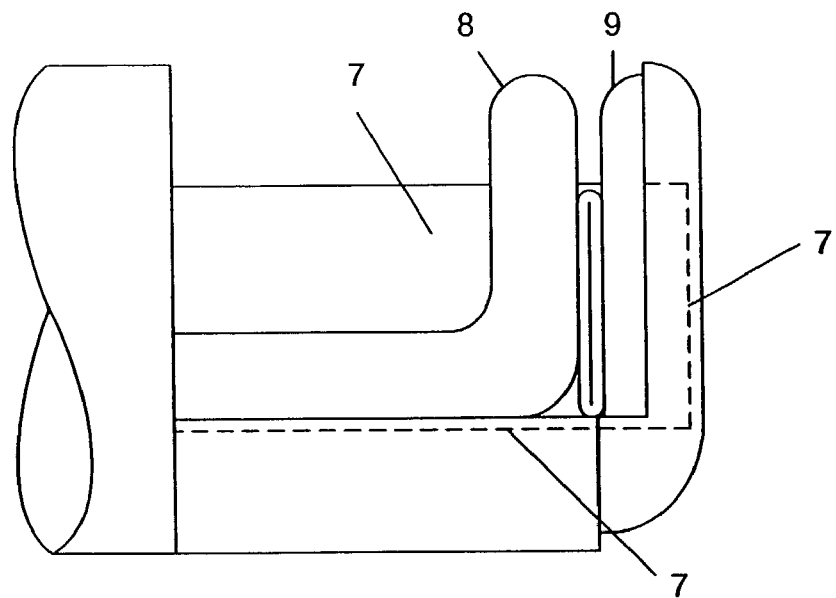
FIG. 8 is a side view of the embodiment shown in FIG. 6, demonstrating the operation of the device including a cutting mechanism at a surgical site.

FIG. 8 shows another side view of the end effector region of the device after the cutting mechanism 7 has been fully advanced distally to cut through the compressed vessel 24. The broken lines show the position of the cutting mechanism within the device. As discussed herein, a stop located inside the housing preferably limits the distal motion of the cutting mechanism so that it does not come into contact with, or extend beyond, the distal edge of the second arm. Preferably, the first and second arms of the device include a guide slot to allow translational movement of the cutting mechanism, as discussed in more detail below.

Figure 9:
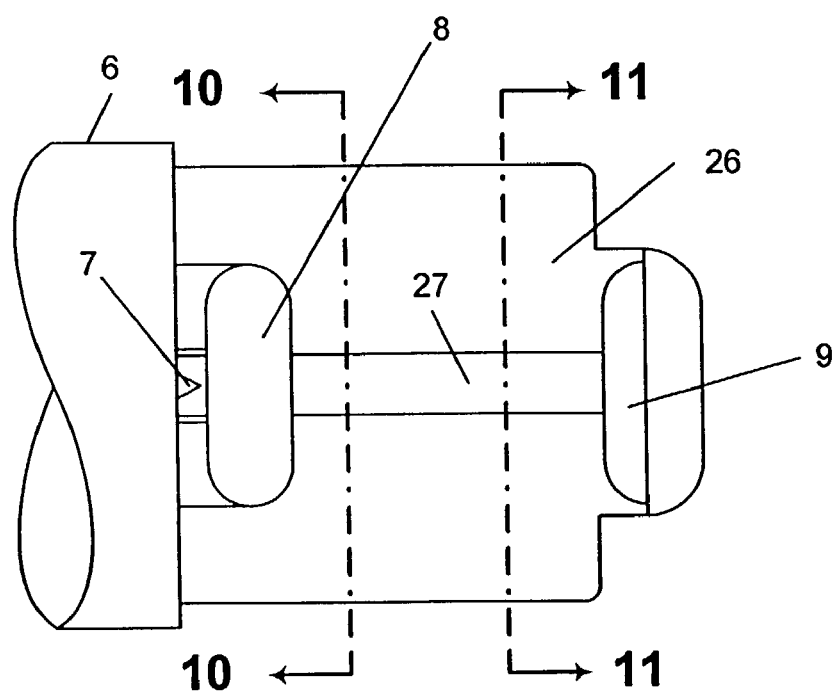
FIG. 9 is a top view of the embodiment shown in FIG. 6, wherein the first electrode and cutting mechanism are retracted.

FIG. 9 shows a top view of the end effector embodiment shown in FIG. 9. The cutting mechanism 7 and the first arm are shown in a retracted, or fully proximal, position. In one preferred embodiment, the second arm includes a platform portion 26 that comprises a generally flattened area located proximal the bent portion of the arm. The platform portion 26 is configured to accommodate tissue, such as a blood vessel, to be treated with the device. At the same time, the platform portion 26 is limited by the diameter of the tubular member 6, so that the second arm is capable of freely translating in the proximal and distal directions within the tubular member 6. The platform portion 26 can be used to hold a vessel or tissue to be treated in position prior to compression and RF treatment. Preferably, the platform portion 26 includes a guide slot 27, to allow translational movement of the cutting mechanism 7. When included in the device, guide slot 27 stabilizes and guides the cutting mechanism in a straight path when it is moved distally toward the second arm. In the embodiment shown in FIG. 9, the distal arm is preferably insulated to avoid treating tissue that is not positioned between the two arms of the device.

Figure 10:
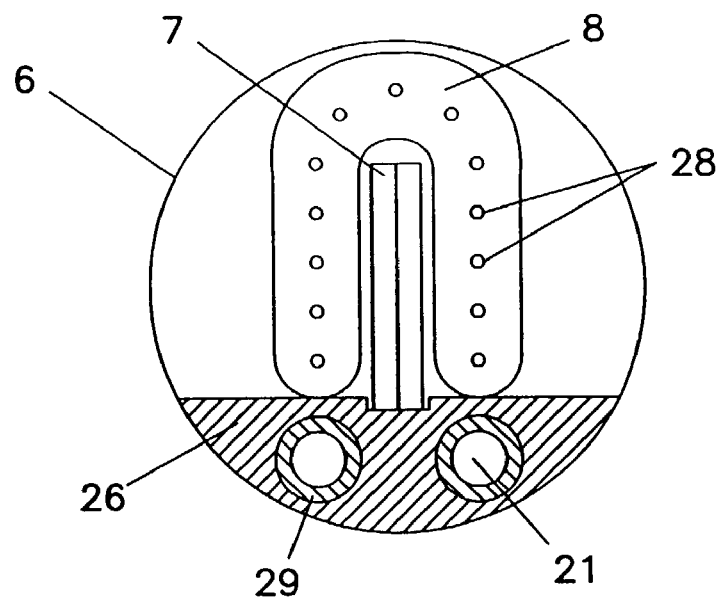
FIG. 10 is a cross-sectional view taken along line 10-10 of FIG. 9.

FIG. 10 shows a cross-sectional view along line 10-10 of FIG. 9. This view looks toward the proximal direction of the device, down the axis of the tubular member 6 toward the housing 1. In this embodiment, first arm is shown including a "U" shaped electrode 8 on its face. A series of small diameter holes that define solution infusion openings 28 are oriented around the surface of the first electrode 8. The entire surface of the first electrode 8 that is shown in this figure is exposed metal that may conduct electrical energy to tissue. Cutting mechanism 7 is seen with the sharp edge being the line down the middle of the centerline of the figure. The platform portion 26 that supports the second electrode is made of a non-conductive material such as a polymer or ceramic. Two legs of the second electrode loop tubing are buried in the platform portion 26, each shown with a thin wall 29 of stainless steel or other electrically conductive material, and a solution delivery tube 21 to convey saline or other electrically conductive fluid to the distal electrode. The solution delivery tube 21 comprises the distal portion of solution supply tube 4 of the device.

Figure 11:
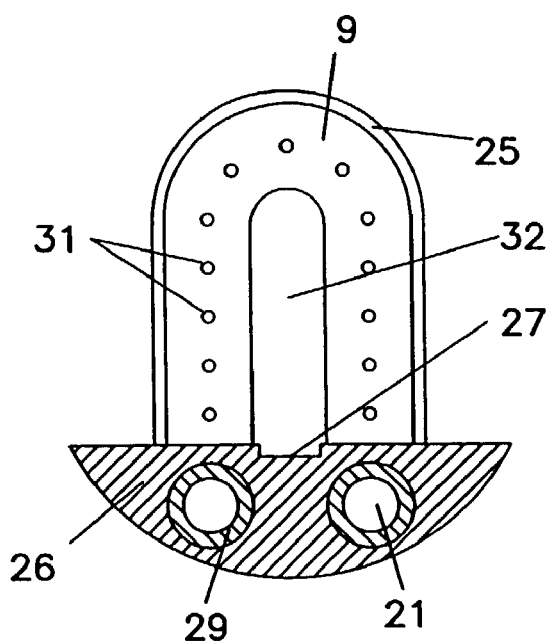
FIG. 11 is a cross-sectional view taken along line 11-11 of FIG. 9.

FIG. 11 shows a cross-sectional view along line 11-11 of FIG. 9. This view looks toward the distal end of the device, facing the exposed metal portion of the second, stationary electrode. In this embodiment, the shape of the distal electrode "bent-up" loop is "U" shaped, with a series of small diameter holes that define solution infusion openings 31 oriented around the surface of the electrode. Gap 32 indicates where the distal tip of the cutting mechanism (not shown) travels. The guide slot 27 that holds the lower part of the cutting mechanism is shown here in cross-section. In this embodiment, the platform portion 26 is shown as containing two tubing sections, each with a thin wall 29 and a solution delivery tube 21.

Solution infusion openings, in the form of a series of fine laser-drilled holes, each with a diameter of about 0.001 to about 0.010 inches, preferably about 0.005 to about 0.007 inches, allows the solution to exit the tubing. In an alternative embodiment, the solution infusion openings are formed by electrical discharge machining (EDM), chemical treatment, etching of the metal, or any suitable method for forming holes of the desired size in the tubing. Solution infusion openings are provided at sufficient intervals along the face of the electrode that will contact tissue to provide the desired effect. Preferably, the metal tubing is insulated everywhere except where it is desired that electrical energy be conducted to tissue. Preferably, at least one electrode is insulated.

The dimensions of the holes or openings and the spacing between holes, as well as the tubing inside diameter and tubing wall thickness are chosen so that the flow of saline is reasonably well distributed to all the openings. If the resistance to flow down the lumen of the tubing is small compared to the resistance to flow through an individual hole or opening, then all holes will provide sufficient flow for proper device operation. Generally, resistance to flow is inversely proportional to the fourth power of the diameter of the lumen or hole, so that doubling the size of the opening reduces resistance to flow to 1/16th of the initial value. Typically, the inside diameter of the tubing would range from 0.02 to 0.1 inches and wall thickness would range from 0.004 to 0.01 inches. However, it is understood that these measurements can be modified for a particular application as desired. In a preferred embodiment described in more detail below, solution infusion openings are included within a groove to achieve flow of conductive solution throughout the groove and across the surface of the electrode that is used to treat tissue as described herein.

Figure 12:
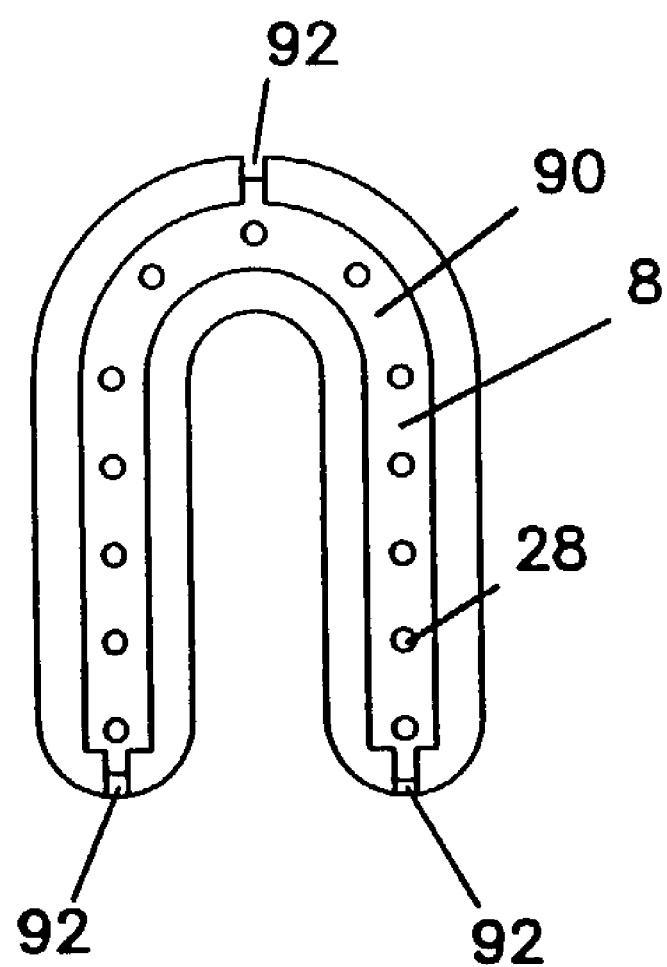
FIG. 12 is an end view of an embodiment of a grooved arm of the invention.

Referring to FIG. 12, an alternative embodiment of the electrode is shown. In this embodiment, the needle tubing contains one or more portions where the insulation has been removed, forming an arm having an exposed portion of the electrode 8 that is recessed from the insulated portions. This results in a electrode having solution infusion openings contained in a groove 90 of the arm. Preferably, this grooved configuration further includes exit slots 92 to allow electrically conductive fluid to exit the groove and flow freely away from the distal end of the device. In this embodiment, the groove 90 serves to isolate the metal electrode from direct contact with bodily tissues being treated. Additionally, the groove 90 provides constant spacing between the electrode 8 and tissue to be treated. This in turn provides wet electrical coupling of the electrode to tissue, through the electrically conductive solution, at a constant distance. Further, the groove assists in preventing tissue from pressing against and occluding the solution infusion openings 28 during squeezing of the arms of the device against tissue. Such tissue pressure against solution infusion openings 28 could inhibit or reduce electrically conductive fluid locally. If saline is not provided at the electrode/tissue interface the proper coupling or conducting of RF electrical energy may not occur.

Figure 13:
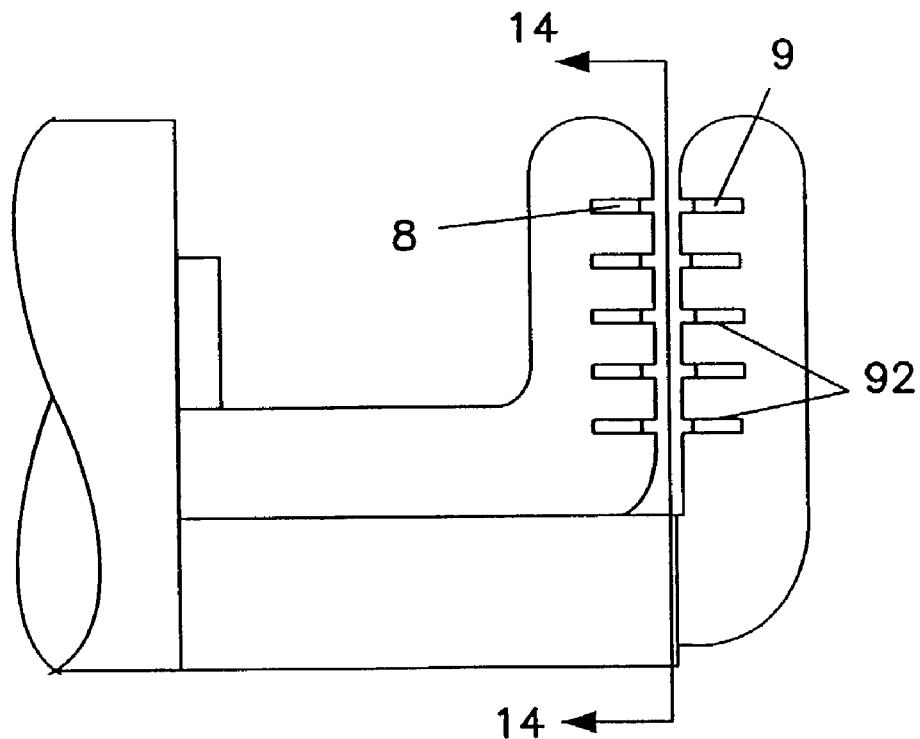
FIG. 13 is a side view of the embodiment shown in FIG. 12, showing an embodiment of the device with a plurality of exit slots from a groove.

FIG. 13 shows a side view of multiple exit slots 92 emanating from a grooved electrode configuration as described above and shown in FIG. 12. In this embodiment, the exit slots 92 extend about groove 90 around the insulated metal electrode tubing to assure that solution can exit from the groove 90 without being blocked by compressed tissue. The recessed metal of the two electrodes 8 and 9 are shown as exposed by these side exit slots 92.

Figure 14:
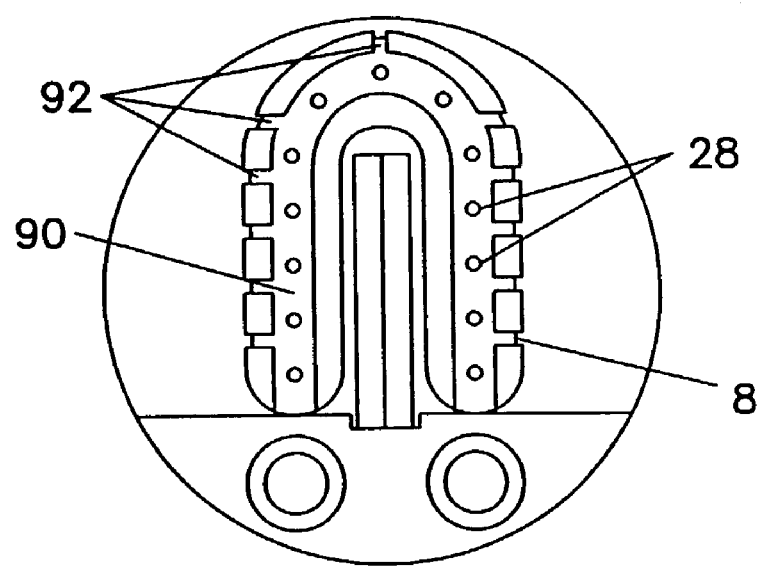
FIG. 14 is a cross-sectional view taken along line 14-14 of FIG. 13.

FIG. 14 shows how the face of the electrode from FIG. 13 appears when viewed along section 14-14 defined in FIG. 13. Exit slots 92 are provided in a spaced relation about groove 90 to provide outlet of the conductive solution, and the spacing of the exit slots 92 can be adjusted as desired.

In the embodiments shown in FIGS. 12-14, the exit slots 92 assist in preventing solution from being trapped in the groove 90. If there were a groove and no exit slots it would still be possible for tissue pressure to inhibit solution flow, since the groove would form a closed space between the electrode and the tissue. Solution pumped into such a closed space could exit by forcing open a gap between the tissue and the electrode insulation, for example, when the solution pressure in the space of the groove exceeded the pressure of the tissue pressing against the insulation. Though solution can ultimately leak out as tissue is coagulated and shrunk, the distribution of solution over the total electrode surface can be uneven and result in dry spots where RF energy is not conveyed to tissue as effectively. It is desirable to make the flow rate of solution independent of how hard the tissue is clamped between the two electrodes.

A preferred embodiment of the device includes a large number of relatively small exit slots, approximately 0.005 inches to approximately 0.020 inches wide and from approximately 0.005 inches to approximately 0.020 inches deep.

Alternatively, the groove is fabricated from electrically non-conductive porous polymer or ceramic, preferably polymer or ceramic composed of a material that is easily wetted by the electrically conductive solution. In this embodiment, the solution exits through the sides of the groove by passing through the porous polymer or ceramic material. Wettability is usually expressed in terms of the contact angle formed between a drop of liquid lying on a solid surface, with small angles representing better wettability than large angles. Using a porous material that is more wettable reduces the amount of pressure required to initially force solution through the fine pores. Teflon™ (polytetrafluoroethylene), for instance, is not as well wetted by saline as most ceramics, and thus would be less desirable as a material from which to from the groove.

Using a porous material for the groove creates a very large number of very small exit slots, and is one method of providing solution exits that provide for uniform flow distribution while also being simple to manufacture.

It should be understood that there can be more than a single groove on an electrode. If the electrode is more rectangular or square-shaped, it may be desirable to have a system of criss-crossing or cross-hatched grooves evenly distributed over the surface of the electrode. It will be appreciated that the precise pattern of such a plurality of grooves can be modified to any desired pattern, while maintaining a gap of conductive solution between metal electrode and tissue that is not subject to compression by tissue even when the electrodes are pressed firmly together.

In a preferred embodiment shown in FIGS. 12-14, the first electrode and second electrode each contain a groove 90, optionally further including exit slots 92. Preferably, the configuration of the groove 90 and exit slots 92 (when provided) are mirror images on the first and second electrodes.

Slightly prior to and during RF application, a flow rate of conductive fluid, such as physiologic saline ("normal" saline, or 0.9% NaCl solution) or lactated Ringer's™, is provided so that a total flow rate of about 0.1 to 10 cc/min is flowing from laser-drilled holes located on the proximal and distal electrodes. Preferably, a total flow rate of about 0.5 to 2 cc/min is flowing from the laser-drilled holes. Other suitable conductive solutions include hypertonic saline and Ringer's™ solution.

Figure 15:
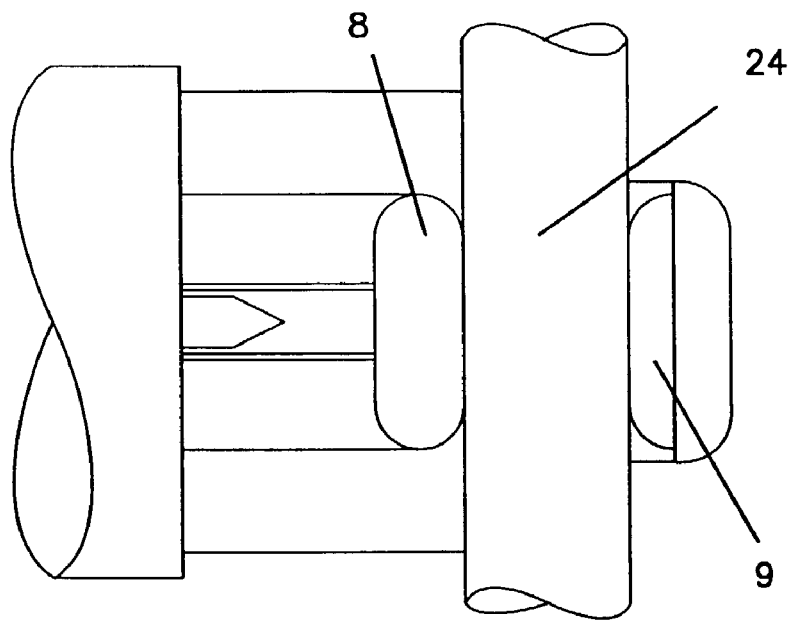
FIG. 15 is a top view of the distal end of the device, demonstrating operation of the device of FIG. 6.

In use, the first, translationally movable arm containing first electrode 8 is moved in a distal direction toward the second, stationary arm containing second electrode 9. FIG. 15 shows a top view of the end effector region of the device during use, showing the first electrode 8 and the second electrode 9 in position so that the blood vessel 24 is just in contact with each electrode. In this view, the blood vessel is captured between the arms of the device so that it is in contact with the electrodes of the device. The cutting mechanism 7 is shown as partially advanced from the tubular member.

Figure 16:
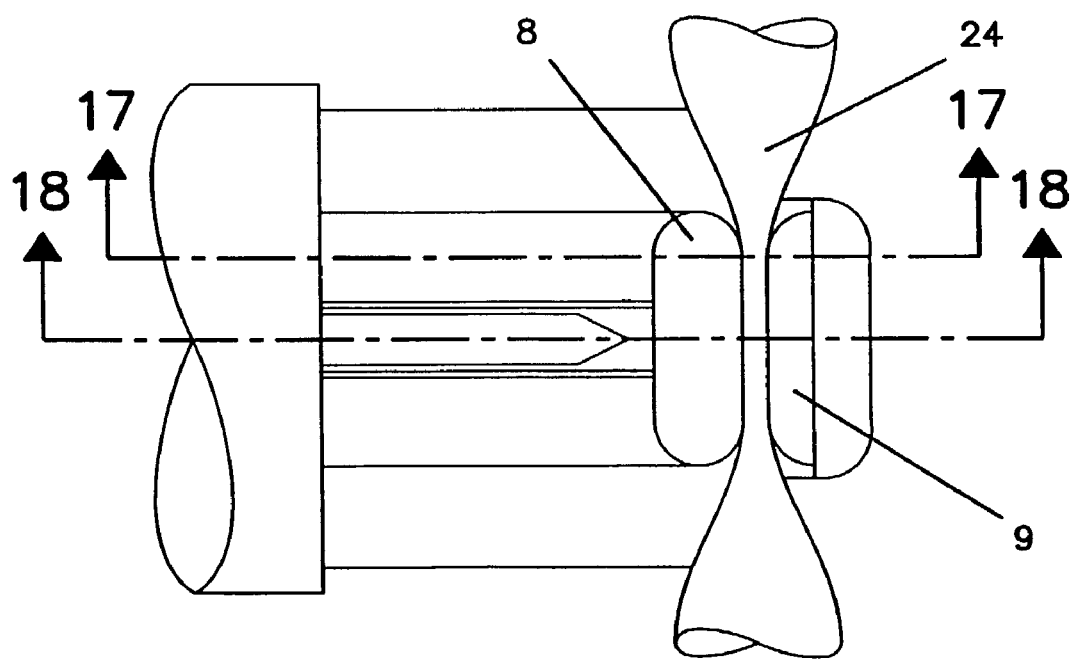
FIG. 16 is a top view of the distal end of the device, demonstrating operation of the device of FIG.6.

FIG. 16 shows another top view of the end effector region after the first arm has been advanced as far in the distal direction as it can go, resulting in the compression of the blood vessel 24 against the second arm.

Figure 17:
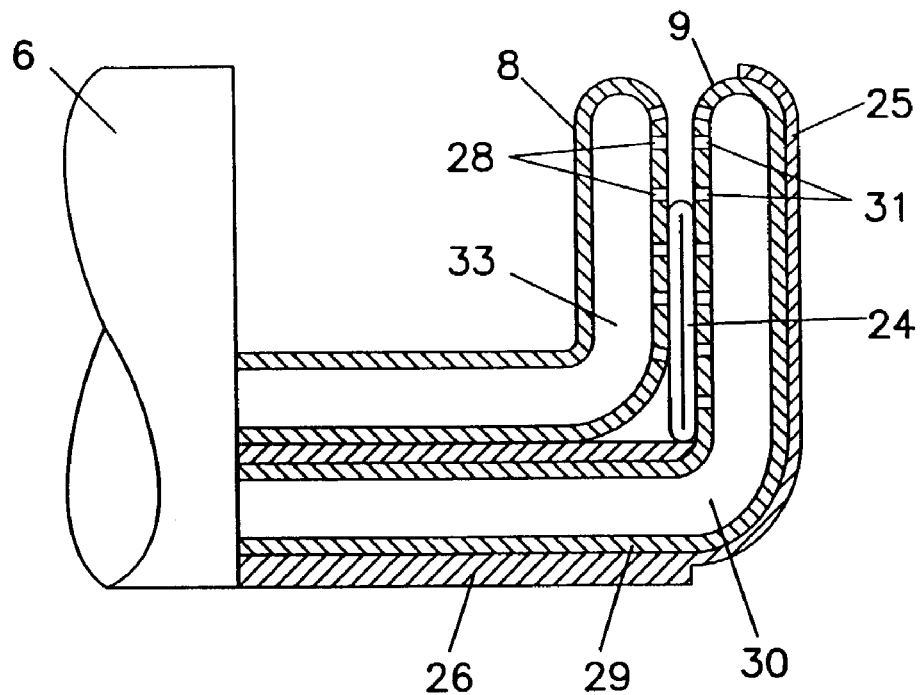
FIG. 17 is a cross-sectional view taken along line 17-17 of FIG. 16.
Figure 18:
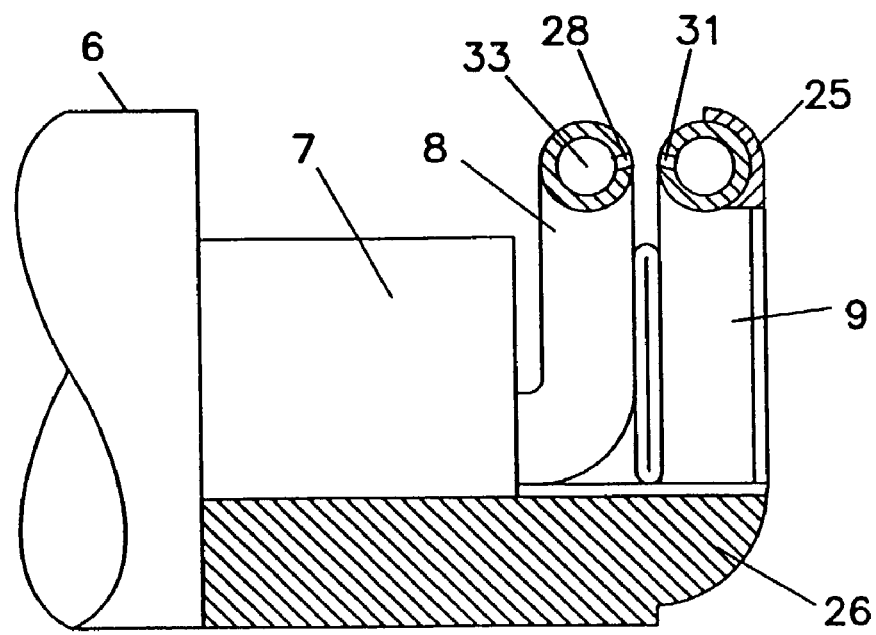
FIG. 18 is a cross-sectional view taken along line 18-18 of FIG. 16.

FIG. 17 shows a cross-sectional view along line 17-17 of FIG. 16. One lumen 33 of the first electrode 8 is shown, being very similar to one of the lumens 30 that supply the distal electrode 9. The small diameter holes (solution infusion openings 28 for the first electrode and 31 for the second electrode) are located so that saline or other conductive solution is supplied to the electrode-tissue interface. The insulation 25 that covers the distal end of the second arm is also shown in this section. FIG. 18 shows a cross-sectional view along line 18-18 of FIG. 16. As shown in FIGS. 17 and 18, lumens 33 and 30 are shown passing through the metal tubing of each of the first and second arms which, as indicated in the application above, may provide the structural foundation of electrode 8 and electrode 9.

Figure 19:
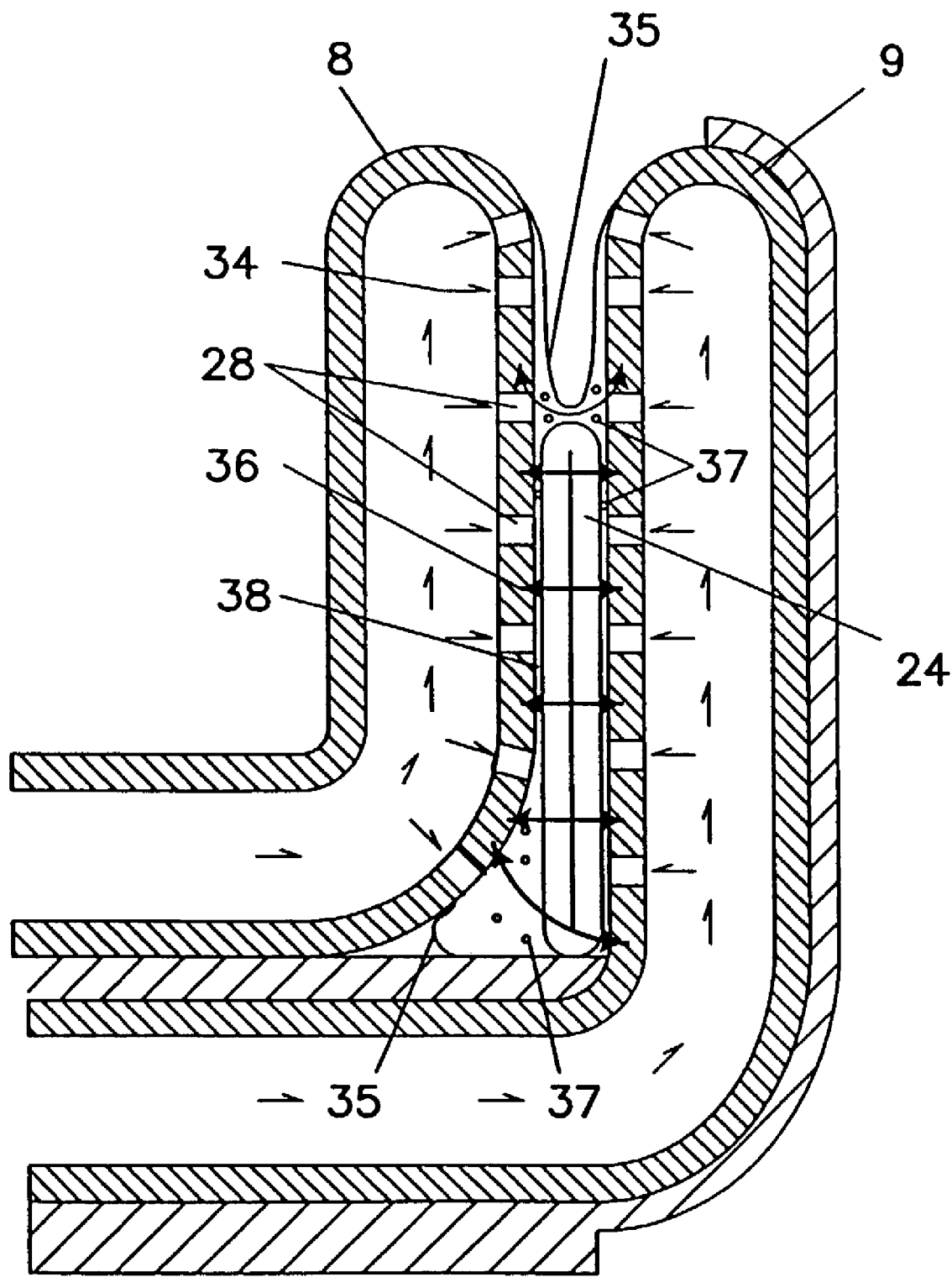
FIG. 19 is an enlarged cross-sectional view taken along line 17-17 of FIG. 16, demonstrating saline flow and current paths during RF application.

FIG. 19 shows an enlarged cross-sectional view along line 17-17 of FIG. 16, with conductive solution flowing and RF electrical energy being applied. Conductive solution is indicated by the small arrows 34 flowing through one of two lumens and then through a number of solution infusion openings 28. In this view, the blood vessel 24 is separated from both the first electrode 8 and second electrode 9 by a gap 38 that is filled with conductive solution. The conductive solution is therefore a coupling agent that is most often between the metal of the electrodes and the tissue. The free surface or interface of the conductive solution and the air is indicated at 35. When a differential high frequency voltage is applied across the electrodes (8 and 9) current flows as shown by the thicker arrows 36. It will be appreciated that the gap 38 need not exist everywhere between the tissue and metal electrodes.

Some of the current may flow between the two electrodes without passing through the blood vessel 24, by only passing through a film of conductive solution. This situation may occur at the edges of the blood vessel or tissue being treated. The majority of the current will preferably pass through conductive solution and then through the tissue being treated. Under some circumstances the tissue can become hot enough to have some of the conductive solution boil, as shown by the small vapor bubbles 37 in the conductive solution film. It will be understood that when the device is used as a monopolar device, the solution need not be delivered to the electrode not in use.

The solution infusion openings of the electrodes supply conductive solution to the treatment site. In an alternative embodiment, these solution infusion openings can be provided in the form of porous material such as metal. In this embodiment, the electrodes do not include discrete laser drilled solution infusion openings; rather, the electrode surface itself is porous to allow infusion of the conductive solution to the treatment site. Porous sintered metal is available in many materials (such as, for example, 316L stainless steel, titanium, Ni-Chrome, and the like) and shapes (such as cylinders, discs, plugs, and the like) from companies such as Porvair, located in Henderson, N.C.

Porous metal components can be formed by a sintered metal powder process or by injection molding a two-part combination of metal and a material that can be burned off later to form pores that connect (open cell) to each other. Such methods are known in the art. In this embodiment, conductive fluid will flow out of the electrode everywhere the pores are open. Preferably, the exterior (i.e., the portions of the components that do not comprise the portion of the device involved in tissue treatment) of such porous metal electrode components can be covered with a material that fills the pores and prevents both the flow of saline and the passing of electrical energy.

Figure 20:
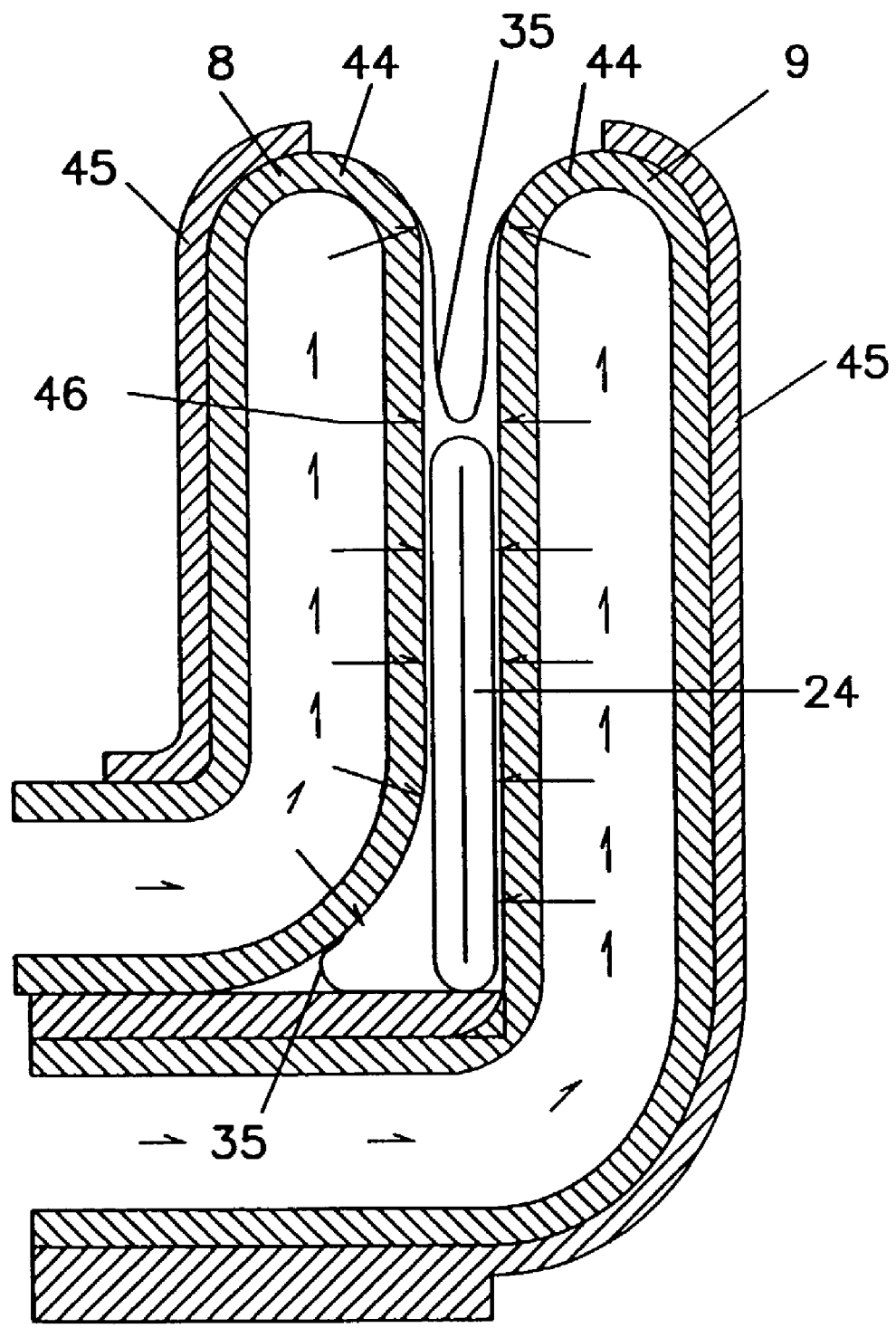
FIG. 20 is a side cross-sectional view of the one embodiment of the device, including porous metal electrodes.

FIG. 20 shows an enlarged cross-sectional view along line 17-17 of FIG. 16. In this embodiment, porous metal 44 comprises both first electrode 8 and second electrode 9. A portion of the outer surface of each electrode is insulated with a non-conductive polymer 45. In this embodiment, conductive solution flow 46 now travels through the porous metal 44 to wet the blood vessel 24. The surface of the conductive solution is shown as 35.

In yet another embodiment, a porous polymer is used in place of the porous metal. Although the polymer is non-conductive, the conductive solution provided will conduct the RF energy across the porous polymer wall and to the tissue to be treated. Suitable materials include high temperature open cell silicone foam and porous polycarbonates, among others. Porous ceramics would also fall into this category, since they could distribute flow, withstand high temperatures and be machinable or moldable for manufacturing purposes. Preferably, the material used transmits both fluid flow and electrical energy; thus, materials with properties midway between high-electrical conductivity metals and low electrical conductivity polymers are also contemplated, such as porous carbon-filled polymers.

Because the conductive solution, such as saline, is generally less electrically conductive than the previously described electrode metals (such as stainless steel), there are several steps that can optionally be taken to avoid dissipating an excess of electrical energy in the resistance of saline. Optionally, hypertonic saline is used instead of "normal" or physiologic saline. By adding more sodium chloride to the water it is possible to decrease the electrical resistivity of the solution by a factor of 3 to 5. Preferred hypertonic (i.e., saturated) saline includes 14.6% sodium chloride (NaCl) at 37° C. and has a resistivity of 5.9 ohm-cm. This is in contrast to "normal" saline, which is 0.90% NaCl, with resistivity of 50 ohm-cm at 37° C. (body temperature).

Figure 21:
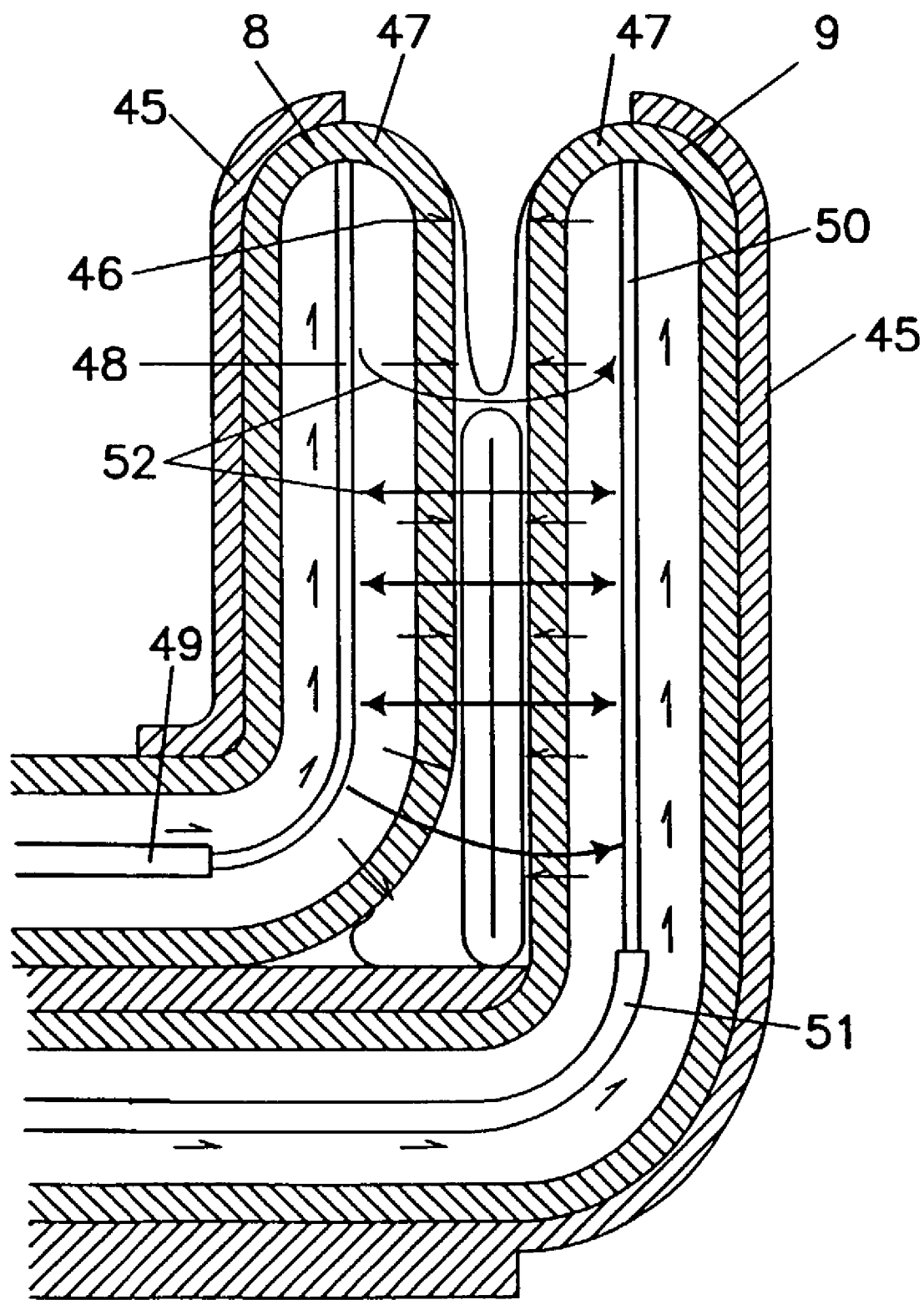
FIG. 21 is a side cross-sectional view of an alternative embodiment of the device, including porous polymer electrodes.

In yet another alternative embodiment, shown in FIG. 21, a wire electrode 48 is included in the first and second arms of the device. As shown in the figure, the wall of each of the hollow electrodes 8 and 9 comprises a porous polymer 47. Conductive solution 46 flows through the porous polymer wall. In previously described embodiments where the electrodes are fabricated from metal, the RF energy is conducted to the electrode-tissue interface by the metal in the wall of the electrode tubing. In the present embodiment, the metal is replaced by porous polymer, and a "replacement" electrical conductor can be used to provide RF energy to the inner wall of the porous polymer near the tissue to be treated. Electrical energy is supplied to the first electrode 8 from a wire electrode 48 that is preferably made of a metal such as platinum that resists corrosion. This wire is insulated by a sheath 49 of some non-conductive polymer such as Teflon™. The second electrode is supplied RF electrical energy by exposed electrode wire 50 which is insulated by sheath 51. Preferably, the outer surface of the porous polymer is insulated by another polymer coating 45, similar to the coating for porous metal electrodes, to keep conductive solution from flowing out of the first and second arms to locations where treatment is not desired. In this embodiment, the RF field lines 52 run from the exposed wire 48 through conductive solution, through the conductive solution in the porous polymer wall of the first electrode 8, through the solution gap and/or the blood vessel, to the corresponding elements of the device on the opposing side of the blood vessel to the second electrode's exposed wire 50. Alternatively, this porous polymer is fabricated from a solid polymer tube or hollow member that has mechanically or laser-drilled small diameter holes in it.

The frequency of the electrical energy is typically 500 kHz, and the power is typically in the range of about 10 to about 150, preferably in the range of about 30 to about 70 watts. A typical range of conductive solution flow rates is about 18-270 cc/hr. In a preferred embodiment, the total flow rate of conductive solution to both electrodes is approximately determined as 1.8 times the power in watts, with the result in cc/hr.

As discussed above, an RF source provides energy through the conductors, to the electrodes of the device. The RF source can be provided as a generator, as described. Alternatively, the source can be configured to be received within or attached to the housing of the device.

Optionally, the invention is provided with a cutting mechanism, indicated in the figures generally as 7. Preferably, the cutting mechanism 7 is independently movable from the first or second arm, or both. As described herein, the cutting mechanism serves to cut tissue preferably after application of RF energy, such that the tissue has been coagulated. Cutting tissue after coagulation reduces risk of bleeding from the tissues, especially with respect to highly vascularized tissue such as the liver, during treatment. However, it will be understood that the invention does not require tissue coagulation prior to cutting, for example in situations where bleeding is not a concern.

The cutting mechanism of the invention is preferably provided in the form of a sharp blade. However, it is apparent from the present description that the cutting mechanism need not be sharp, especially when the cutting mechanism is supplied with RF energy, as described below. In another embodiment, the cutting mechanism can be provided in the form of a wire. In yet another embodiment, the cutting mechanism is not itself sharp, but cuts tissue through the use of RF energy, as described herein.

Figure 22A:
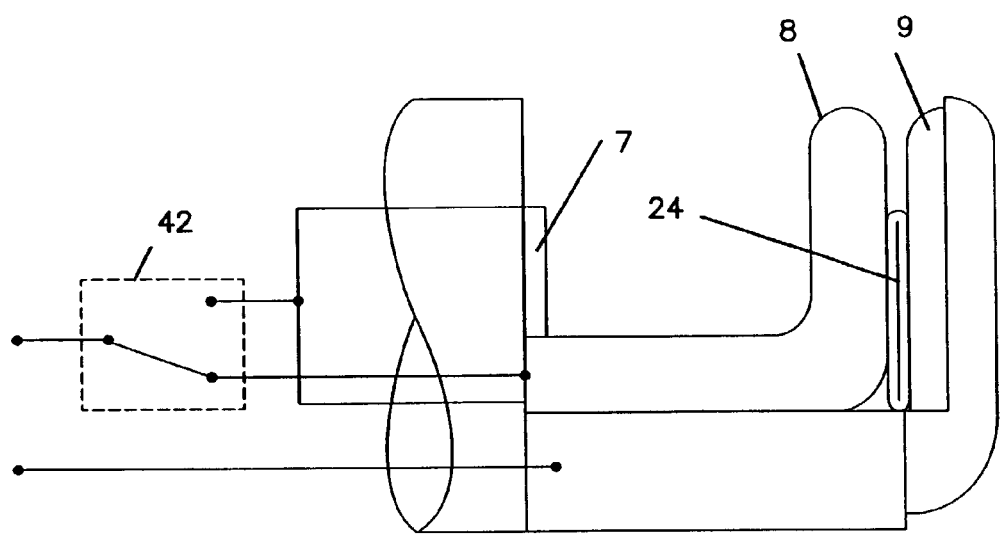
FIGS. 22a and 22b are schematic side views of two embodiments of the electrical connections to the arms and/or the cutting mechanism of the device.
Figure 22B:
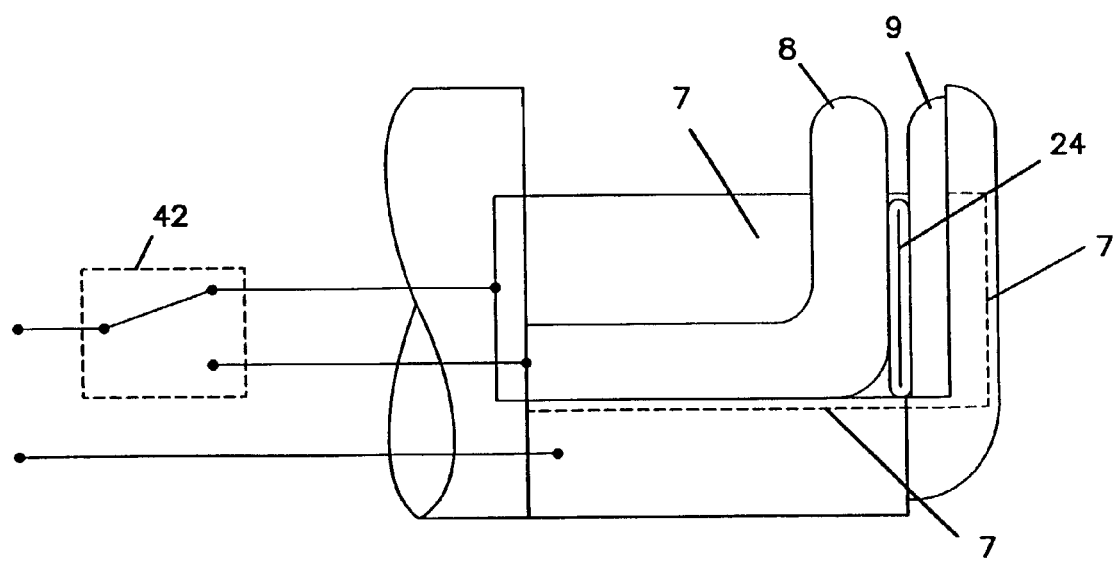

Optionally, the device is configured to supply the cutting mechanism 7 with RF energy. Moreover, the device can be configured to allow the device to be switched between a bipolar mode in which RF energy is supplied to the first electrode, and a second bipolar mode in which RF energy is supplied to the cutting mechanism 7. FIGS. 22a and 22b illustrate this embodiment of the invention. FIG. 22a shows the situation during treatment of blood vessel 24 (e.g., coagulation), with a switch 42 configured to provide RF energy to the first electrode 8. In this operating mode, one of the two electrical paths is connected to the first electrode 8, and the lower electrical connection is made to the second electrode 9. After the vessel has been coagulated and it is desired to cut the sealed vessel, FIG. 22b shows switch 42 to operate the device in a second mode, wherein the electrical connection that previously supplied first electrode 8 in FIG. 22a with RF energy is now connected to the cutting mechanism 7. In this mode, as cutting mechanism 7 moves into contact with the sealed vessel, the edge of the blade concentrates the RF field so that the RF energy aids in the cutting of the tissue. This feature is intended to provide improved cutting efficiency and minimize the effects of the blade becoming progressively more dull with use and less able to cut cleanly with minimal force.

Figure 23:
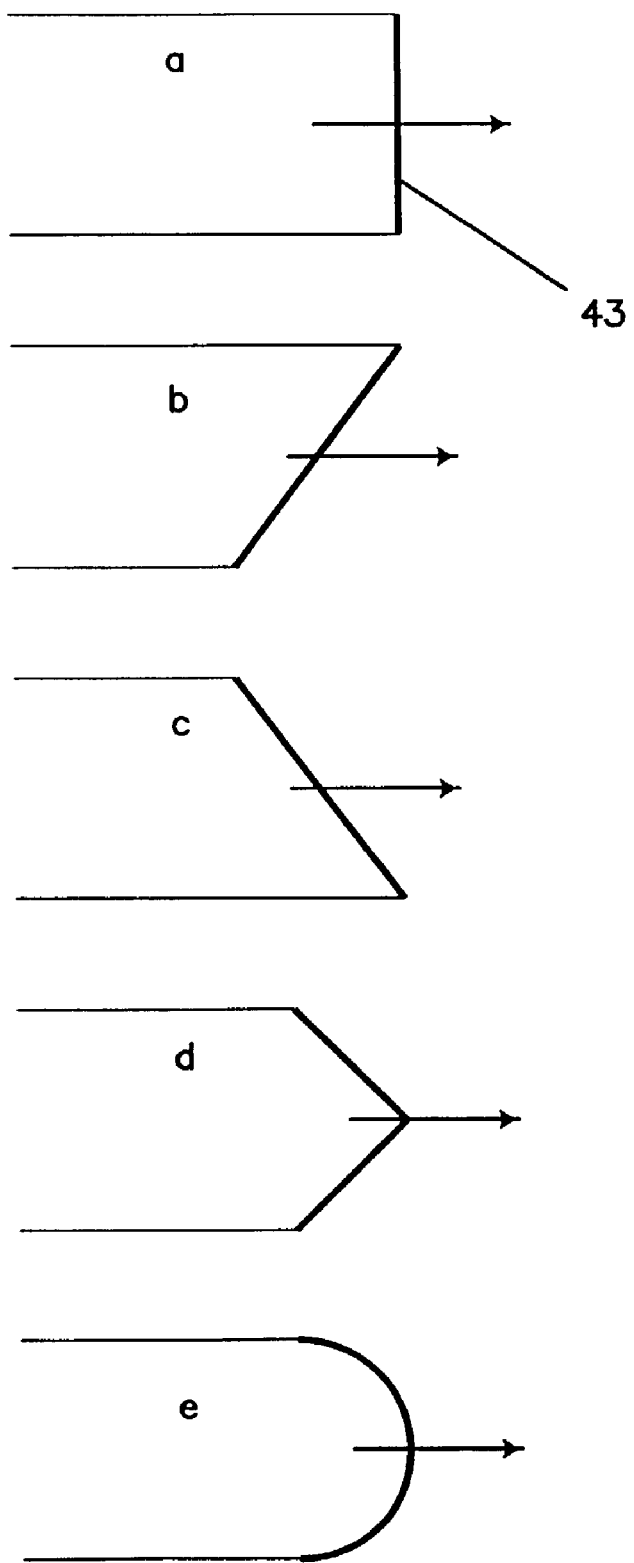
FIGS. 23a-23e show various shapes for the cutting mechanism of the invention.

The cutting mechanism of the invention can be provided in a variety of suitable configurations to achieve cutting of the tissue. FIGS. 23a through 23e illustrate a number of alternative shapes for the cutting mechanism, when provided in the form of a blade, with the arrow indicating the direction of cutting motion. As shown, the cutting mechanism can provide a right angle straight edge (FIG. 23a), an angled edge with a recessed edge downward toward the platform portion 26 of the second arm (FIG. 23b), an angled edge with a recessed edge upward (FIG. 23c), a two-faceted edge (FIG. 23d), or a rounded edge (FIG. 23e). The sharp edge 43 is shown as a bolder line for all five of the variations shown. While it is intended that none of the additional variations of cutting mechanism shape would protrude beyond the distal electrode (e.g., for safety reasons) the different shapes are all intended to provide potentially improved cutting by recessing some part of the leading sharp edge. Other suitable shapes can be utilized to achieve the desired cutting according to the invention, and the shapes shown are illustrative only and should not be considered limiting.

Figure 24:
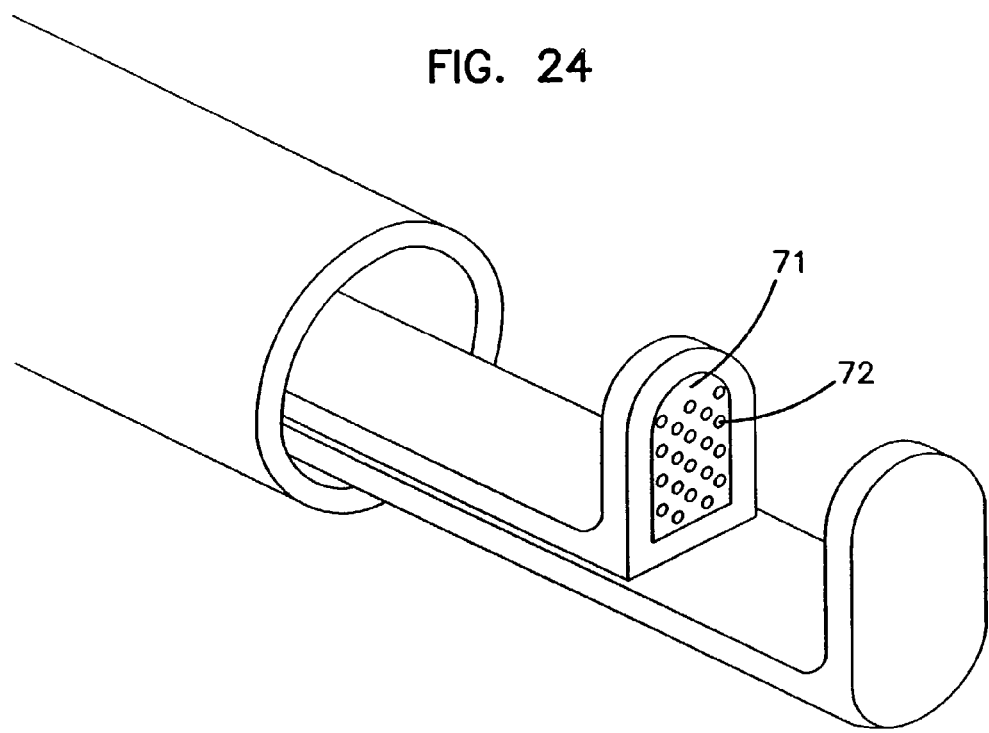
FIG. 24 is a perspective view of an alternative embodiment of the electrode of the invention.
Figure 25:
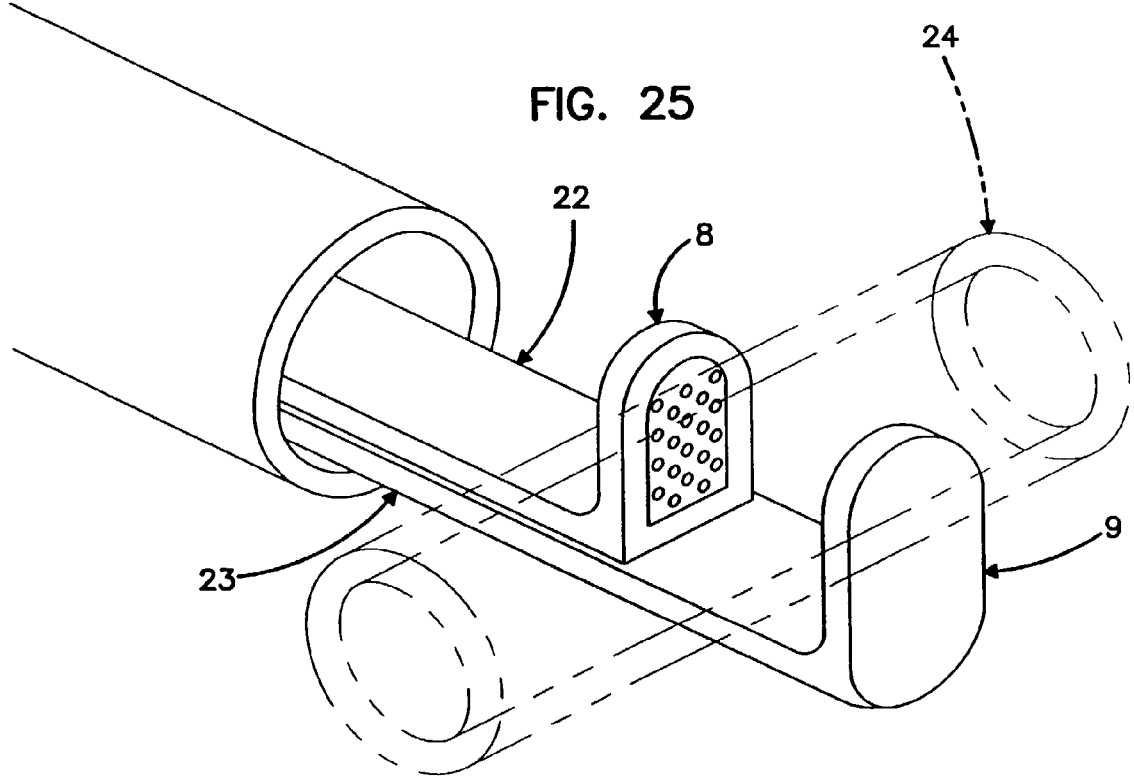
FIG. 25 is a perspective view of the embodiment of FIG. 24, showing treatment of a blood vessel.

As discussed herein, the cutting mechanism comprises an optional component of the device, to be used when the operator desires to cut a tissue or blood vessel during treatment. When the device is provided without a cutting mechanism, the first and second arms can be fabricated such that they do not include a slot to allow passage of the cutting mechanism through the arm and thereby through tissue. In this embodiment, the first and second arms are preferably provided in a "paddle-like" form, with varying amounts of roundness to the corners. This embodiment is depicted in FIGS. 24 and 25. FIG. 24 shows a schematic representation of a paddle-like electrode connected to a conductor for connection to a radiofrequency source. In this embodiment, the electrode surface 71 is provided with solution infusion openings 72 on its face. FIG. 25 shows a schematic representation of a paddle-like electrode configuration, showing the first and second electrodes, 8 and 9, positioned with a blood vessel 24 therebetween, and conductors 22 and 23. As shown, the electrodes are preferably substantially the same size.

Preferably, the electrodes of this embodiment are hollow, to allow the flow of conductive solution, and with thin walls to allow the passage of the solution through to tissue. The passage of conductive solution is through either (1) small holes in solid metal or solid polymer (e.g., as shown in FIG. 24) or (2) micro- or macroporosity in metal or polymer. If solid or porous polymer is used, then an internal "replacement" electrode wire can be used to provide RF close to the area where there is tissue (as previously described with respect to porous polymer electrodes). External portions of electrodes made with porous materials are preferably insulated electrically and made impervious to keep conductive solution from weeping out where not desired. One advantage of using paddle-like electrodes with otherwise larger surface areas is that the larger electrode areas can provide lower impedance to RF power and Thereby faster treatment times.

Use

The device of the invention can be used to coagulate and cut body tissues, such as a blood vessel, in a variety of applications. Exemplary applications are described herein, without intending to be limited thereto. Further, it is understood that the description herein can be used to treat a number of body tissues, and the invention is not limited to treatment of tissues provided as examples.

Figure 26A:
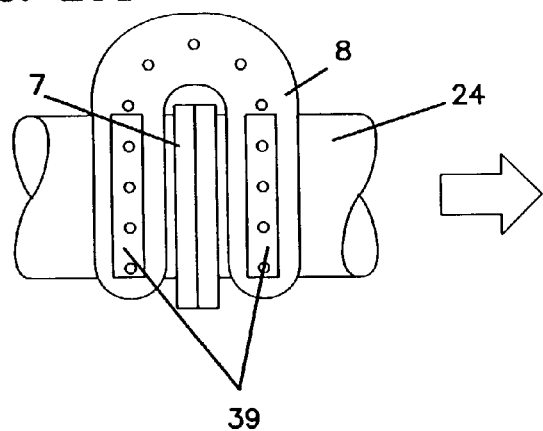
FIGS. 26a-26b show the coagulation and cutting pattern for a small vessel according to one embodiment of the invention.
Figure 26B:
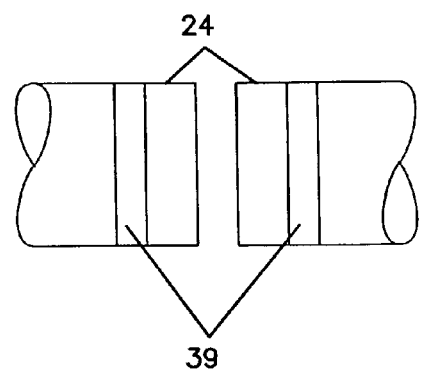
Figure 27A:
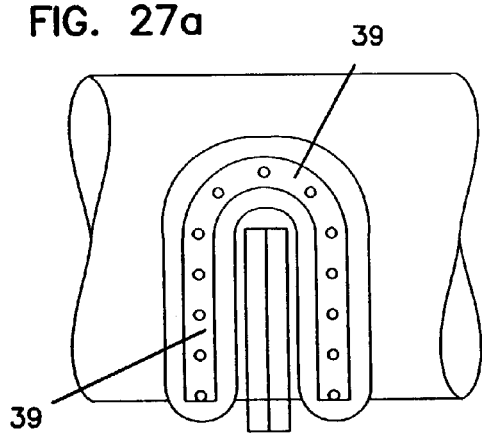
FIGS. 27a-27d show the coagulation and cutting pattern for a larger vessel according to one embodiment of the invention.
Figure 27B:
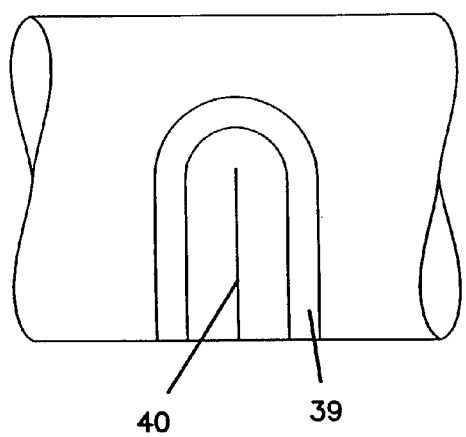
Figure 27C:
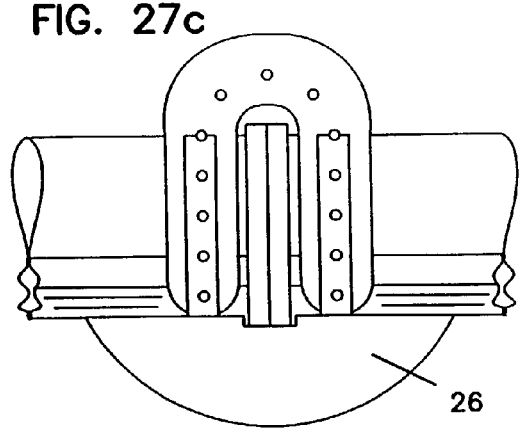
Figure 27D:
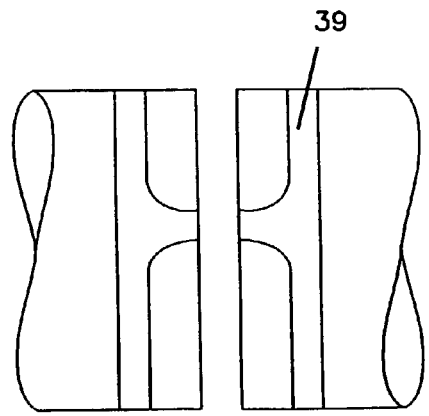

FIG. 26 shows the coagulation and cutting pattern when the device is used on a blood vessel of diameter small enough to be coagulated and cut with a single pass. FIG. 26a is oriented to view the blood vessel 24 and first electrode 8 when looking in a distal direction from the housing and down the tubular member 6. In this embodiment, the operator positions the device, the blood vessel is compressed, then RF is applied, resulting in the coagulation pattern shown in FIG. 26b as coagulation zone 39. The coagulation zone 39 is shown as smaller than the total exposed metal electrode surface area, though it could be larger than the metal area. This is not a critical aspect of the invention, since the size of the coagulation zone is under the direct control of the surgeon who will typically use visual feedback (e.g., color) to determine when tissue has been adequately treated. The size of the coagulation zone is determined by a number of factors, including the length of time that the RF energy is applied, the power level of the RF, the conductive solution flow rate, the type and composition of the tissue, and the tissue compression force.

After cutting the blood vessel with the cutting mechanism 7, the result is shown in FIG. 26b, as two separate pieces of the blood vessel 24. In the coagulation zones 39, the opposite walls of the blood vessel 24 are bonded together so that no blood flows from the edges of the cut.

FIG. 27 shows how the device can be used to coagulate and cut a larger blood vessel. As shown in the first of four figures, 18a, the device is positioned and a U-shaped coagulation zone 39 is generated. The result of this treatment is shown as 27b, the U-shaped coagulated zone 39, with a cut 40 in between. In order to coagulate and cut again to complete the vessel transection, FIG. 27c shows how the device is positioned up into the cut 40 which has been spread apart by the platform portion 26 of the second arm. After compression and application of RF energy, followed by another cutting action, the transected vessel appears approximately as shown in FIG. 27d, with the final coagulation zone shown as 39. The coagulation zone 39 shown for the two-step procedure is only schematic and not intended to be a precise rendering. A larger vessel could also be sealed by approaching the vessel from the opposite side for the second seal, instead of from the same side, as just described.

Figure 28:
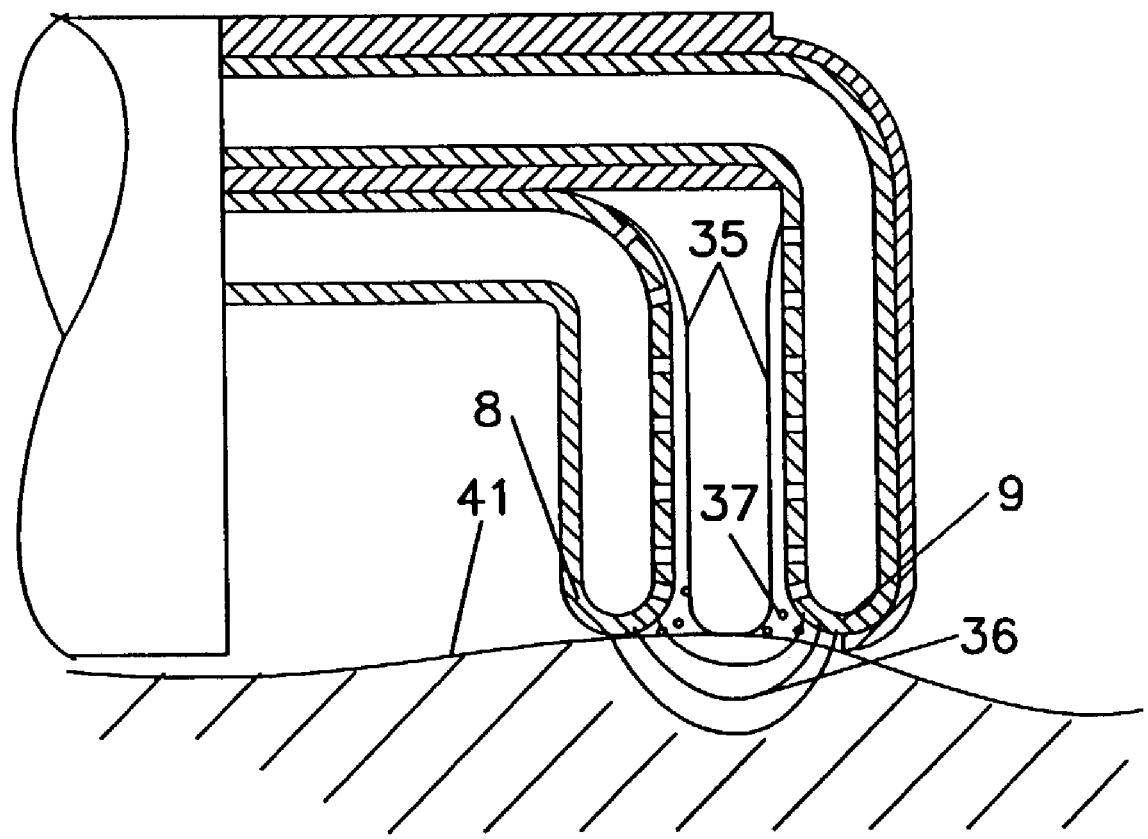
FIG. 28 shows one embodiment of the device involving coagulative surface "painting" with no tissue between the electrodes.

FIG. 28 shows an alternative way that the device can be used to treat tissue that is not grasped between the two electrodes, but rather is located in a noncoaptive manner adjacent to the distal end surface of the tips of the two electrode loops which, as shown in FIG. 28, along with other drawings, each comprise a spherical distal end surface. This type of operation is sometimes referred to as "coagulative surface painting." With the first arm advanced distally, but not all the way forward (i.e., toward the second electrode), and both RF energy delivery and conductive solution flow turned on, the electrical field lines 36 are schematically shown, extending from the tip of first electrode 8 of the first arm, through tissue and conductive solution, to second electrode 9 of the second arm. The surface of the conductive solution 35 that has exited from the small holes extends downward in the direction of gravity to wet the surface 41 of the tissue. Vapor bubbles 37 may or may not be present in the conductive solution as a result of heat generated by the RF energy. The device need not be oriented as indicated in the figure for this mode of tissue treatment to occur; that is, the device can be used to treat tissue that is positioned above the device, since conductive solution will wet both the metal electrode and tissue surfaces, even in opposition to the force of gravity. The sides of the device could also be used to perform coagulative painting. In such an embodiment, the sides of the electrodes are provided with sufficient surface area to achieve the desired coagulative effect.

In a preferred embodiment, the device includes a locking mechanism. Once the optimum separation distance is achieved between the first and second electrodes, further movement of the first electrode is prevented by engaging an electrode locking mechanism that locks the position of the electrode. In one embodiment, this locking mechanism is located on the housing near the actuation member 2 (shown in FIGS. 1 and 2) that moves the first arm translationally. The locking mechanism is used to selectively lock and unlock the first arm in a desired position. In use, the physician determines the optimum distance between the arms, based upon visual feedback relating to how the end effector region of the device is interacting with tissue as the separation distance of the first and second arms is changed. For example, once the arm is locked in position it would be easier for the physician to "paint" the surface of a heavily bleeding organ, such as liver, without being concerned about the electrode moving and losing the desired effect. The locking mechanism also prevents the first electrode from inadvertently contacting the second electrode during use (e.g., during application of RF energy). Alternatively, the locking mechanism is provided in the activation member 2.

The locking mechanism is provided to lock one, or both of the arms. When the device includes a first arm that is translationally movable, and a second, stationary arm, the locking mechanism is provided to selectively lock the first arm in a desired position. In turn, when the device includes a second arm that is translationally movable, the locking mechanism is provided to selectively lock the second arm in a desired position. Alternatively, when both arms are translationally movable, the locking mechanism can selectively lock or unlock one or both of the movable arms.

Generally, as the first and second electrodes are moved closer together, a larger fraction of the conductive solution flow may boil, leading to a "hotter" tissue surface temperature. Conversely, as the electrodes are positioned further away from each other, a smaller fraction of the conductive solution will boil, leading to a lower surface temperature effect.

In another embodiment, the device is capable of treating areas of the body that are difficult to reach anatomical sites. In this embodiment, the device is provided with the ability to articulate or flex, to allow the end effector region of the device to access areas of the body requiring treatment that may be difficult to reach using minimally invasive or noninvasive techniques. As used herein, "articulate" means the tubular member is capable of moving about a joint or a jointed area as described herein. In one preferred embodiment, the tubular member 6 is provided with the ability to articulate, to allow the operator to maneuver the device within the patient's body to reach the treatment site. Alternatively, the tubular member 6 can be angled or flexible, to facilitate engaging a tissue from a selected approach position.

FIGS. 29 and 30 show one preferred embodiment of this device. As shown in FIG. 29, tubular member 6 includes an articulation zone 53 that is located a predetermined distance from the distal end of the device. In one embodiment shown in the figures, the area of the tubular member 54 that is located between articulation zone 53 and the first arm of the device is rigid, and the area of the tubular member 55 that is located on the proximal side of the articulation zone is also rigid. Within the articulation zone 53 is a rib construction of polymer ribs 56 separated by air gaps 57. Other suitable constructions of the articulation zone 53 are possible to achieve articulating movement of the tubular member. Alternatively, in an embodiment not shown, the areas of the tubular member 54 and 55 are flexible. Additionally, the device includes at least one articulation zone 53 and can include multiple articulation zones, as desired.

In one embodiment, rotatable knob 58 is located on the housing to control movement of the articulation zone 53, and thereby control articulation of the device. As rotatable knob 53 is rotated by small incremental amount, the articulation zone 53 bends a correspondingly small incremental amount. This bending or articulating is shown in FIG. 30. When the rotatable knob 58 is rotated through a series of detents, the articulation zone 53 goes through a series of small incremental bends, for example, of perhaps 5 degrees of arc per increment. The first offset view of the angled end effector 59 is at an angle of 30 degrees, and the second offset view of the end effector 60 is at an angle of 60 degrees. The enlarged top view of the articulation zone 53 shows the ribs 57 and gaps 56 during such articulating movement. When the articulation zone bends, the diameter of gaps 56 decreases on one side of the tubular member, and increases on the opposite side of the tubular member.

The invention has been described as a bipolar surgical device, whereby RF energy is supplied to the first and second electrodes, or to one of the electrodes and the cutting mechanism. Alternatively, the device can be provided as a monopolar surgical instrument. In this embodiment, only one of the first or second electrode is provided with RF energy and a flow of conductive solution. In one preferred embodiment, the first, translationally movable arm containing the first electrode is provided with conductive solution and RF as previously described. According to this embodiment, the second arm is provided as a structural component only and is not provided with solution or electrical energy. In an alternative preferred embodiment, the second electrode is provided with conductive solution and RF energy, as previously described. According to this embodiment, the first arm is provided as a structural component only and is not provided with conductive solution or electrical energy. When the device is used as a monopolar device, the second electrode is provided as a pad placed under the patient, as a ground, or a dispersive electrode.

Figure 31:
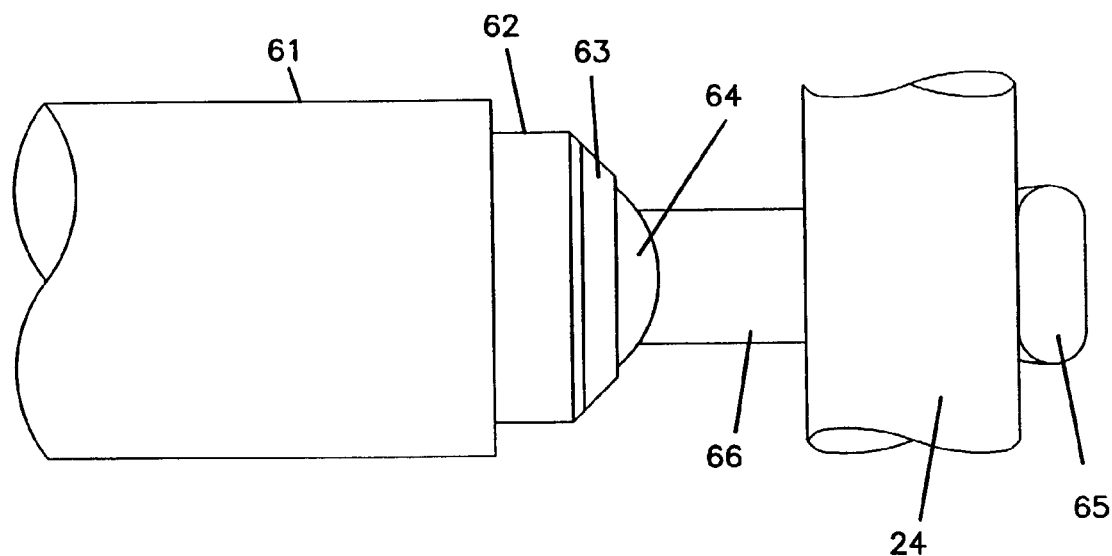
FIG. 31 is a top view of an alternative embodiment of the device, including a second electrode as a ball tip.

The invention contemplates alternative configurations for the first and second arms, and the first and second electrodes. In one embodiment, the first arm of the device is provided in the form of a spring-loaded ball tip. As shown in FIG. 31, one configuration of the device includes a first arm in the form of a ball tip and a second arm configured in a paddle-like form. The tubular member 61, which corresponds to tubular member 6 of FIG. 1, comprises a non-conductive polymer and contains the outer sheath 62 of the ball shaft, also fabricated from a non-conductive polymer. According to this embodiment, the first arm of the device is provided in the form of outer sheath 62 of the ball shaft, and the first electrode is provided in the form of a ball 64. A spherical ball 64 is positioned within outer sheath 62 and is partially held in place by a rim 63 of the sheath 62. The second electrode is positioned within the second arm provided in the form of insulated spatula 65, that is attached to the tubular member 61 by a support member 66, also preferably insulated. In a preferred embodiment, the electrodes are configured such that the inner opposing surface area of each is substantially the same size, such that the surface area of the ball that contacts tissue is substantially the same as the surface area of the second electrode (e.g., spatula). Preferably, the electrode surface areas that contact and treat tissue are provided in a 1:1 ratio. Preferably, ball 64 is fabricated from a suitable metal, such as stainless steel and the like.

Figure 32:
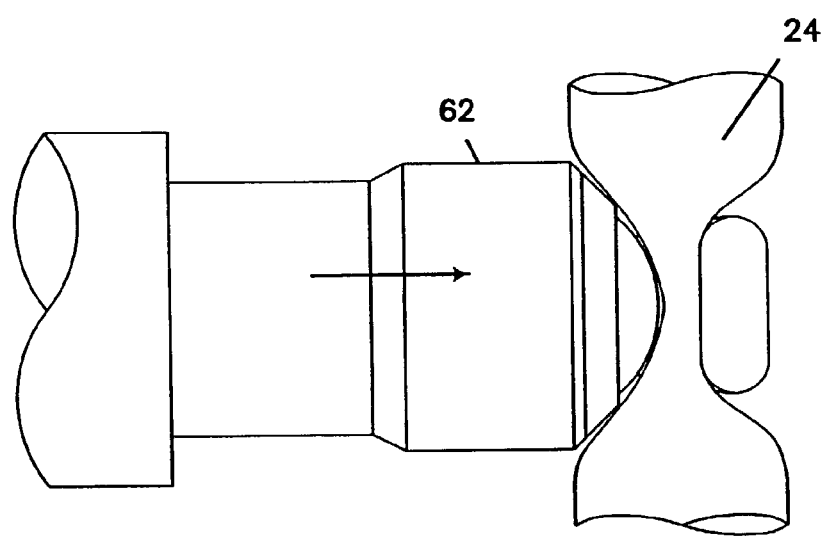
FIG. 32 is a top view of the device shown in FIG. 31, demonstrating operation of the device.

FIG. 32 shows a top view of the embodiment of FIG. 31 with the ball advanced distally to compress the vessel 24 against the second electrode.

Figure 33:
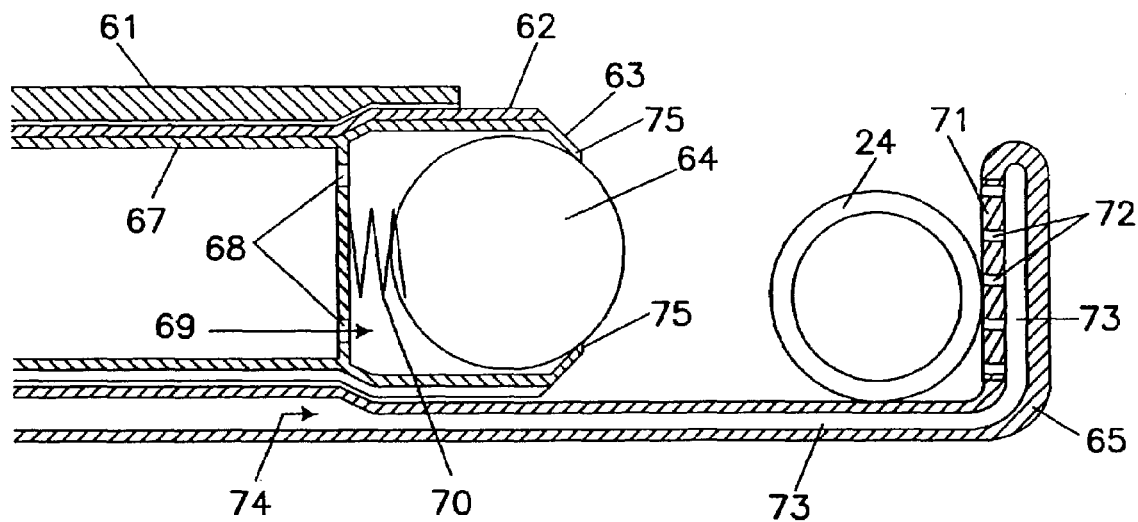
FIG. 33 is a side cross-sectional view of the embodiment shown in FIG. 31

FIG. 33 shows a cross-sectional view of the embodiment shown in FIG. 31. The tubular member 61 contains the outer insulating sheath 62 of the ball shaft, the rim 63 and the ball 64. The rim 63 is part of a tubular structure 67 that conveys both electrical energy and a flow of conductive solution, such as saline, to the tip of the ball. In a preferred embodiment, the rim and tubular structure 67 are fabricated of a suitable metal, such as stainless steel and the like. Conductive solution, such as saline, flows from the housing in the tube 67, through a number of holes 68, past spring 70 which pushes the ball 64 against the rim 63, and out to the outer surface of the ball through gouges 75. The saline flow clings to the surface of the ball 64 and the rim 63 through the action of surface tension. Saline flowing to the ball is shown as 69 as it passes through the holes in the tubular structure that holds the spring in place. Spring 70 biases the ball 64 in a distal direction, thereby urging the ball 64 against rim 63.

In one embodiment, the second electrode is comprised of a plate 71 with a plurality of holes 72 in it, that convey a flow of conductive solution 74 down a lumen 73. The distal end portion 65 of the second arm comprises insulation covering the second electrode. Preferably, the plate 71 is metal.

Figure 34:
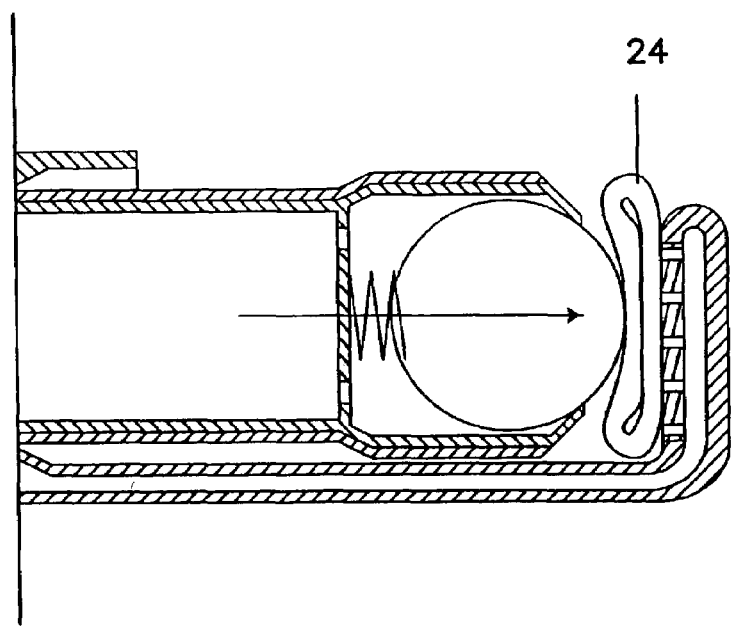
FIG. 34 is a side cross-sectional view of the embodiment shown in FIG. 32.

FIG. 34 shows a cross-sectional view of the embodiment shown in FIG. 32. In this figure, the ball shaft is advanced proximally to compress the blood vessel 24 against the second electrode.

Figure 35:
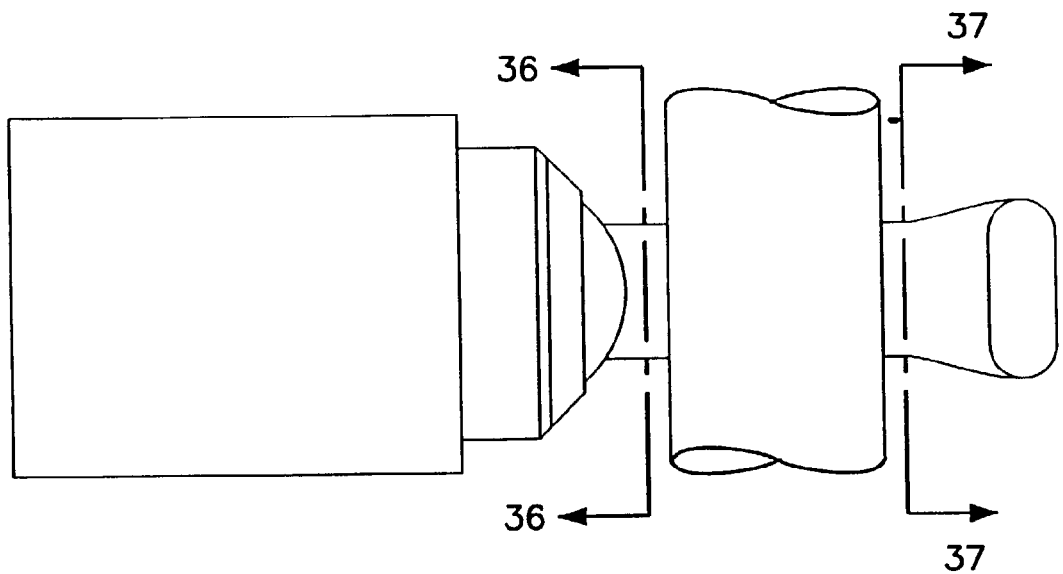
FIG. 35 is a top view of one embodiment of the invention.
Figure 36:
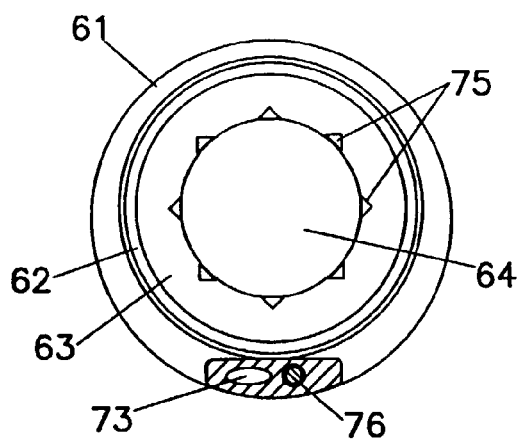
FIG. 36 is a cross-sectional view along line 36-36 of FIG. 35.

FIG. 35 is a top view of another embodiment of the invention. FIG. 36 shows a view along line 36-36 of FIG. 35, looking proximally at the spherical surface of the ball 64. A radial series of small gouges 75 in the rim 63 allows conductive solution to flow freely around the rim of the ball even when the spring is pressing the ball firmly against the rim. Also shown are the tubular member 61, the outer sheath 62 of the ball shaft, the lumen 73 in the second arm that conveys conductive solution to the second electrode, and insulated conductor 76 that conveys electrical energy to the second electrode 71.

Figure 37:
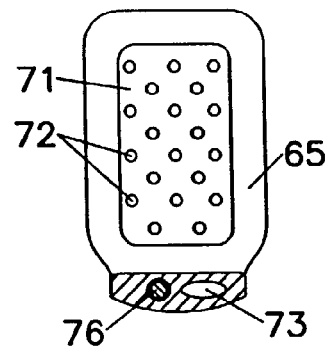
FIG. 37 is a cross-sectional view along line 37-37 of FIG. 35.

FIG. 37 shows a view along line 37-37 of FIG. 35, looking in a distal direction at the second arm of the device. According to this embodiment, the second arm includes second electrode 71 with holes 72, lumen 73, and conductor 76. The connection of conductor 76 to the distal electrode 71 is not shown, but can be accomplished with a crimp of a tab of the electrode 71 that would at least partially wrap around the conductor before crimping.

Figure 38:
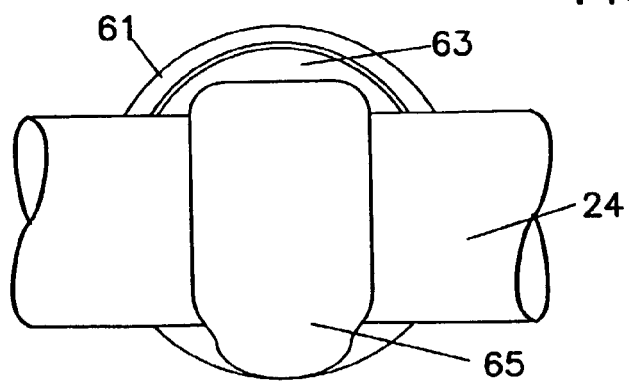
FIG. 38 is an end view of the embodiment shown in FIG. 35.

FIG. 38 is an end view of the distal end of the device, showing the blood vessel 24, the insulated covering 65 of the second arm, the tubular member 61 and the metal rim 63.

The ball embodiment of the invention provides a combination of advantages. For example, if the ball becomes clogged with char it can easily be unclogged by pressing the ball distally against the second arm. As the ball is pushed against any solid object, the spring 70 compresses and the ball moves proximally to a position behind the rim 63, thus breaking off any adherent char. This unclogging feature is not intended to be routinely used, since the presence of saline normally prevents the creation of any char. However, there may be circumstances when the physician may inadvertently misuse the device by excessively turning up the power or turning down the flow rate, which might result in boiling off all the flow off saline, drying out the "wetness" of the device and causing char formation as the tissue temperature rises significantly above 100° C.

Figure 39:
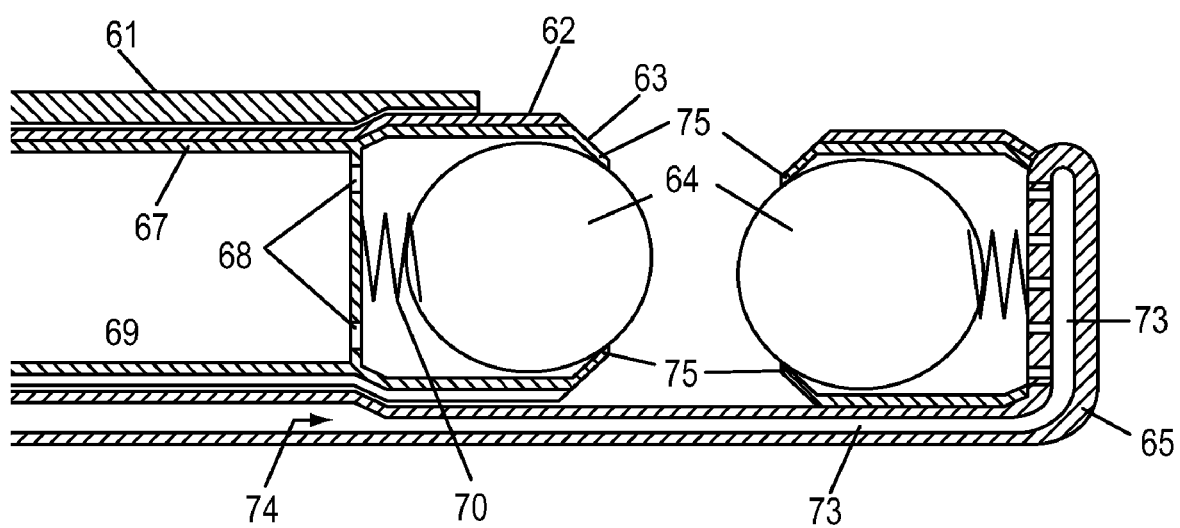
FIG. 39 is a side cross-sectional view of an alternative embodiment of the device.

Preferably, when the first electrode of the device is provided in the form of a ball 64, the second arm is shaped with a concave surface facing the convex shape of the first electrode. This "matching" of electrode shapes provides improved electrode-tissue contact and hence faster and more uniform tissue coagulation. Alternatively, the second electrode of the device is provided in the form of a ball 64 (FIG. 39), in which embodiment, the first arm can be shaped with a concave surface.

The invention provides a combination of advantages over electrosurgical devices in the art. The device provides tissue coagulation and cutting without tissue desiccation, sticking, perforation, smoke formation, char formation, or thermal spread of high temperatures. Further, the invention provides electrodes of a variety of shapes and orientations that are supplied with a flow of saline in order to maintain the electrode-tissue interface continuously wetted during the application of RF energy. This "wet" electrode design will limit the peak tissue temperature to 100° C. or less and prevent tissue sticking, tissue perforation, smoke formation, char formation, and high temperature thermal spread. These advantages lead to faster, easier and safer surgical procedures.

Further, the device of the invention provides the ability to treat tissue and vessels in hard-to-reach places. One preferred configuration of the device as a tubular, angled coagulator with a movable first electrode and an optional movable cutting mechanism leads to the advantage of a low profile both during insertion and during actuation, compared to scissors-type devices. The articulating end effector region of the device also confers a significant advantage of being able to reach difficult anatomical sites. This ultimately leads to faster surgical procedures, reduced cost and increased safety. Moreover, the ability to access hard-to-reach areas of the body for treatment using the device may allow surgeons to perform noninvasive or at least minimally invasive procedures. This in turn avoids risks associated with open surgical procedures, such as risk of infection, longer healing time, and the like.

The invention thus provides a multi-purpose instrument that can be used to provide both vessel or tissue coagulation and cutting, plus surface coagulation for stopping surface bleeding without having to remove the device from the trocar.

The design of the device enables bipolar coagulation and cutting without having to remove the device from its location at the target tissue. The device can also optionally be used in the bipolar mode to perform surface coagulation or coagulative "painting" with the space between the bipolar electrodes empty of tissue. The flow of saline is effective in achieving good coupling of RF energy to tissue even when used in this painting mode.

Additionally, the invention provides a device that can be used as a monopolar or bipolar device, and is switchable between the two modes.

The invention has been described with reference to various specific and preferred embodiments and techniques. However, it will be apparent to one of ordinary skill in the art that many variations and modifications may be made while remaining within the spirit and scope of the invention.

All publications and patent applications in this specification are herein incorporated by reference to the same extent as if each individual publication or patent application was specifically and individually incorporated by reference.

We claim:

1. A bipolar electrosurgical device to treat tissue by moving along a tissue surface in a presence of radio frequency energy and a fluid provided simultaneously from the device, the device comprising:
   an end effector comprising a first stationary electrode tip and a second stationary electrode tip which are not movable relative to one another;
   the first electrode tip comprising a spherical tissue treating surface;
   the second electrode tip comprising a spherical tissue treating surface;
   at least one fluid exit to provide fluid to the first electrode tip;
   at least one fluid exit to provide fluid to the second electrode tip;
   a first fluid delivery lumen in fluid communication with the at least one fluid exit to provide fluid to the first electrode tip; and
   a second fluid delivery lumen in fluid communication with the at least one fluid exit to provide fluid to the second electrode tip.

2. The device of claim 1 wherein:
the first electrode tip and the second electrode tip are parallel.

3. The device of claim 1 wherein:
the first electrode tip and the second electrode tip are in a side-by-side arrangement.

4. The device of claim 1 further comprising:
a cutting mechanism.

5. The device of claim 4 wherein:
the cutting mechanism comprises a sharp edge.

6. The device of claim 1 wherein:
the first electrode tip and the second electrode tip are of substantially a same size.

7. The device of claim 1 wherein:
the first electrode tip and the second electrode tip are of substantially a same shape.

8. The device of claim 1 wherein:
the first electrode tip comprises an exposed surface area for treating tissue;
the second electrode tip comprises an exposed surface area for treating tissue; and
the first electrode tip exposed surface area and the second electrode tip exposed surface area are of substantially a same size.

9. The device of claim 1 wherein:
the at least one first fluid exit is located proximal to the spherical tissue treating surface of the first electrode tip; and
the at least one second fluid exit is located proximal to the spherical tissue treating surface of the second electrode tip.

10. The device of claim 1 wherein:
at least one of the at least one first and second fluid exits is at least partially defined by the first and second electrode tips, respectively.

11. The device of claim 1 wherein:
the at least one fluid exit to provide fluid to the first electrode tip further comprises a plurality of fluid exits to provide fluid to the first electrode tip; and
the at least one fluid exit to provide fluid to the second electrode tip further comprises a plurality of fluid exits to provide fluid to the second electrode tip.

12. The device of claim 1 further comprising:
a proximal fluid delivery lumen in fluid communication with the first fluid delivery lumen and the second fluid delivery lumen.

13. The device of claim 1 further comprises:
the first fluid delivery lumen in fluid communication with the at least one fluid exit to provide fluid to the first electrode tip passing through a first arm; and
the second fluid delivery lumen in fluid communication with the at least one fluid exit to provide fluid to the second electrode tip passing though a second arm.

14. The device of claim 1 wherein:
the end effector comprises a noncoaptive end effector to treat the tissue other than by grasping the tissue.

15. The device of claim 1 wherein:
the fluid comprises an electrically conductive fluid.

16. The device of claim 1 wherein:
the at least one fluid exit to provide fluid to the first electrode tip has a diameter less than a diameter of the first fluid delivery lumen, and
the at least one fluid exit to provide fluid to the second electrode tip has a diameter less than a diameter of the second fluid delivery lumen.

17. The device of claim 1 wherein:
the at least one fluid exit to provide fluid to the first electrode tip has a smaller opening area than an opening area of the first fluid delivery lumen, and
the at least one fluid exit to provide fluid to the second electrode tip has a smaller opening area than an opening area of the second fluid delivery lumen.

* * * * *